(12) United States Patent
Miller et al.

(10) Patent No.: US 9,651,494 B2
(45) Date of Patent: May 16, 2017

(54) FLUORESCENT PROBES FOR MONITORING VOLTAGE BY PHOTO-INDUCED ELECTRON TRANSFER

(75) Inventors: Evan Walker Miller, La Jolla, CA (US); Roger Y. Tsien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 147 days.

(21) Appl. No.: 14/118,836

(22) PCT Filed: May 21, 2012

(86) PCT No.: PCT/US2012/038876
§ 371 (c)(1),
(2), (4) Date: Nov. 19, 2013

(87) PCT Pub. No.: WO2012/159116
PCT Pub. Date: Nov. 22, 2012

(65) Prior Publication Data
US 2014/0093907 A1    Apr. 3, 2014

Related U.S. Application Data

(60) Provisional application No. 61/488,075, filed on May 19, 2011.

(51) Int. Cl.
*G01N 21/64* (2006.01)
*G01N 33/50* (2006.01)
(Continued)

(52) U.S. Cl.
CPC .......... *G01N 21/6486* (2013.01); *C09K 11/06* (2013.01); *G01N 33/5008* (2013.01);
(Continued)

(58) Field of Classification Search
CPC ............ C09K 11/06; C09K 2211/1007; C09K 2211/1011; C09K 2211/1088;
(Continued)

(56) References Cited

U.S. PATENT DOCUMENTS

| 734,701 A | 7/1903 | Hale |
|---|---|---|
| 4,769,292 A | 9/1988 | Tang et al. |

(Continued)

OTHER PUBLICATIONS

Pinheiro et al. (2011) Nature Nanotechnology 6: 763-772.*
(Continued)

*Primary Examiner* — Lisa J Hobbs
(74) *Attorney, Agent, or Firm* — Morgan, Lewis & Bockius LLP

(57) ABSTRACT

Compounds and methods for determining transmembrane potential, monitoring changes in transmembrane potential, and/or drug screening are provided. In one aspect, compounds of the invention have a structure according to the formula: E-M-A, wherein A is a fluorophore, selected from xanthenes, coumarins, cyanines, bimanes, and difluoroboradizaindacenes, charged at physiological pH; M is a molecular wire; and E is a hydrophobic moiety, wherein A and E are capable of being involved in a photo-induced, intramolecular electron transfer that quenches the fluorescence of A in response to a voltage condition. When in use, compounds of the invention are membrane-impermeant and oriented within the cell membrane such that the charged moiety localizes at the outer leaflet of the lipid bilayer and the hydrophobic moiety and molecular wire associate with the hydrophobic portion of the lipid bilayer. The rate of electron transfer, fluorescence intensity, and quenching are altered in response to changes in transmembrane potential.

82 Claims, 14 Drawing Sheets

(51) Int. Cl.
    G01N 33/542    (2006.01)
    C09K 11/06     (2006.01)
(52) U.S. Cl.
    CPC .... G01N 33/542 (2013.01); *C09K 2211/1007* (2013.01); *C09K 2211/1011* (2013.01); *C09K 2211/1088* (2013.01); *G01N 2500/10* (2013.01)
(58) Field of Classification Search
    CPC ........... G01N 21/6486; G01N 2500/10; G01N 33/5008; G01N 33/542
    See application file for complete search history.

(56)             References Cited

U.S. PATENT DOCUMENTS

| | | | |
|---|---|---|---|
| 6,468,763 B1* | 10/2002 | Farinas | G01N 33/5005 435/173.4 |
| 7,491,830 B2 | 2/2009 | Lam et al. | |
| 9,057,734 B2* | 6/2015 | Cohen | C07K 14/195 |
| 2007/0026384 A1* | 2/2007 | Tsien | C07D 209/08 435/4 |
| 2009/0093612 A1 | 4/2009 | Lukhtanov | |
| 2010/0255525 A1* | 10/2010 | Koide | G01N 33/582 435/29 |

OTHER PUBLICATIONS

Spillmann et al. (2014) Chem. Commun. 50: 7246-7249.*
Grozema et al. (2000) J. Am. Chem. Soc 122: 10903-10909.*
Aich et al. (1999) J. Mol. Biol. 294: 477-485.*
Robertson et al. (2002) Chem. Soc. Rev. 32: 96-103.*
Wang et al. (2008) Anal. Chem. 80: 6443-6448.*
Taniguchi et al. (2006) 33(1): 1-12.*
Hubener et al. (2003) J. Phys. Chem. B 107: 7896-7902.*
Andersen, O.S. et al., "Bilayer Thickness and Membrane Protein Function: An Energetic Perspective," *Annu. Rev. Biophys. Biomol. Struct.*, 2007, vol. 36, pp. 107-130.
Ataka, K. et al., "A Genetically Targetable Fluorescent Probe of Channel Gating with Rapid Kinetics," *Biophysical Journal*, Jan. 2002, vol. 82, pp. 509-516.
Baca, S.M. et al., "Widespread Inhibition Proportional to Excitation Controls the Gain of a Leech Behavioral Circuit," *Neuron*, Jan. 24, 2008, vol. 57, pp. 276-289.
Bradley, J. et al., "Submillisecond Optical Reporting of Membrane Potential In Situ Using a Neuronal Trace Dye," *The Journal of Neuroscience*, Jul. 22, 2009, vol. 29, No. 29, pp. 9197-9209.
Briggman, K.L. et al., "Optical Imaging of Neuronal Populations During Decision-Making," *Science*, Feb. 11, 2005, vol. 307, pp. 896-901.
Briggman, K.L. et al., "Imaging Dedicated and Multifunctional Neural Circuits Generating Distinct Behaviors," *The Journal of Neuroscience*, Oct. 18, 2006, vol. 26, No. 42, pp. 10925-10933.
Briggmann, K.L. et al., "Monitoring Integrated Activity of Individual Neurons Using FRETT-Based Voltages-Sensitive Dyes," *Membrane Potential Imaging in the Nervous System: Methods and Applications*, Canepari, M. et al., (eds.), 2010, Springer Science+Business Media, LLC, pp. 61-70.
Cacciatore, T.W. et al., "Identification of Neural Circuits by Imaging Coherent Electrical Activity with FRET-Based Dyes," *Neuron*, Jul. 1999, vol. 23, pp. 449-459.
Chanda, B. et al., "A hybrid approach to measuring electrical activity in genetically specified neurons," *Nature Neuroscience*, Nov. 2005, vol. 8, No. 11, pp. 1619-1626.
Davis, W.B. et al., "Molecular-wire behaviour in *p*-phenylenevinylene oligomers," *Nature*, Nov. 5, 1998, vol. 396, pp. 60-63.
De La Torre, G. et al., "Electronic Communication through π-Conjugated Wires in Covalently Linked Porphyrin/$C_{60}$ Ensembles," *Chem. Eur. J.*, 2005, vol. 11, pp. 1267-1280.

De Silva, A.P. et al., "New Fluorescent Model Compounds for the Study of Photoinduced Electron Transfer: The Influence of a Molecular Electric Field in the Excited State," *Angew. Chem. Int. Ed. Engl.*, 1995, vol. 35, No. 16, pp. 1728-1731.
Fernández, J.M. et al., "Induced Capacitance in the Squid Giant Axon," *J. Gen. Physiol.*, Sep. 1983, vol. 82, pp. 331-346.
Fluhler, E. et al., "Spectra, Membrane Binding, and Potentiometric Response of New Charge Shift Probes," *Biochemistry*, 1985, vol. 24, pp. 5749-5755.
Garner, L.E. et al., "Modification of the Optoelectronic Properties of Membranes via Insertion of Amphiphilic Phenylenevinylene Oligoelectrolytes," *J. Am. Chem. Soc.*, 2010, vol. 132, pp. 10042-10052.
González, J.E. et al., "Voltage Sensing by Fluorescence Resonance Energy Transfer in Single Cells," *Biophysical Journal*, Oct. 1995, vol. 69, pp. 1272-1280.
González, J.E. et al., "Improved indicators of cell membrane potential that us fluorescence resonance energy transfer," *Chemistry & Biology*, Apr. 1997, vol. 4, pp. 269-277.
Grinvald, A. et al., "Fluorescence Monitoring of Electrical Responses From Small Neurons and Their Processes," *Biophys. J.*, May 1983, vol. 42, pp. 195-198.
Grynkiewicz, G. et al., "A New Generation of $Ca^{2+}$ Indicators with Greatly Improved Fluorescence Properties," *The Journal of Biological Chemistry*, Mar. 25, 1985, vol. 260, No. 6, pp. 3440-3450.
Horikawa, K. et al., "Spontaneous network activity visualized by ultrasensitive $Ca^{2+}$ indicators, yellow Cameleon-Nano," *Nature Methods*, Sep. 2010, vol. 7, No. 9, pp. 729-732.
Hübener, G. et al., "Anellated Hemicyanine Dyes with Large Symmetrical Solvatochromism of Absorption and Fluorescence," *J. Phys. Chem. B.*, 2003, vol. 107, pp. 7896-7902.
International Search Report for International Patent Application No. PCT/US2012/038876 mailed Nov. 30, 2012, 4 pages.
Jiao, G.-S. et al., "Synthesis of Regioisomerically Pure 5- or 6-Halogenated Fluoresceins," *J. Org. Chem.*, 2003, vol. 68, pp. 8264-8267.
Krajl. J.M. et al., "Electrical Spiking in *Escherichia coli* Probed with a Fluorescent Voltage-Indicating Protein," *Science*, Jul. 15, 2011, vol. 333, pp. 345-348.
Kuhn, B. et al., "Anellated Hemicyanine Dyes in a Neuron Membrane: Molecular Stark Effect and Optical Voltage Recording," *J. Phys. Chem. B*, 2003, vol. 107, pp. 7903-7913.
Kuhn, B. et al., "High Sensitivity of Stark-Shift Voltage-Sensing Dyes by One- or Two-Photon Excitation Near the Red Spectral Edge," *Biophysical Journal*, Jul. 2004, vol. 87, pp. 631-639.
Li, L.-S., "Fluorescence Probes for Membrane Potentials Based on Mesoscopic Electron Transfer," *Nano Letters*, 2007, vol. 7, No. 10, pp. 2981-2986.
Miller, E.W. et al., "Optically monitoring voltage in neurons by photo-induced electron transfer through molecular wires," *PNAS*, Feb. 7, 2012, vol. 109, No. 6, pp. 2114-2119.
Minta, A. et al., "Fluorescent Indicators for Cytosolic Calcium Based on Rhodamine and Fluorescein Chromophores," *The Journal of Biological Chemistry*, May 15, 1989, vol. 264, No. 14, pp. 8171-8178.
Miyawaki, A. et al., "Fluorescent indicators for Ca2+ based on green fluorescent proteins and calmodulin," Nature, Aug. 28, 1997, vol. 388, pp. 882-887.
Nagai, T. et al., "Circularly permuted green fluorescent proteins engineered to sense $CA^{2+}$," *PNAS*, Mar. 13, 2001, vol. 98, No. 6, pp. 3197-3202.
Palmer, A.E. et al., "$Ca^{2+}$ Indicators Based on Computationally Redesigned Calmodulin-Peptide Pairs," *Chemistry & Biology*, May 2006, vol. 13, pp. 521-530.
Perron, A. et al., "Second and third generation voltage-sensitive fluorescent proteins for monitoring membrane potential," *Frontiers in Molecular Neuroscience*, Jun. 2009, vol. 2, Article 5, pp. 1-8.
Sjulson, L. et al., "Rational Optimization and Imaging In Vivo of a Genetically Encoded Optical Voltage Reporter," *The Journal of Neuroscience*, May 21, 2008, vol. 28, No. 21, pp. 5582-5593.
Tian, L. et al., "Imaging neural activity in worms, flies and mice with improved GCaMP calcium indicators," *Nature Methods*, Dec. 2009, vol. 6, No. 12, pp. 875-881.

(56) References Cited

OTHER PUBLICATIONS

Ueno, T. et al., "Rational Principles for Modulating Fluorescence Properties of Fluorescein," *J. Am. Chem. Soc.*, 20014, vol. 126, pp. 14079-14085.
Wang, D. et al., "Improved Probes for Hybrid Voltage Sensor Imaging," *Biophysical Journal*, Oct. 2010, vol. 99, pp. 2355-2365.

* cited by examiner

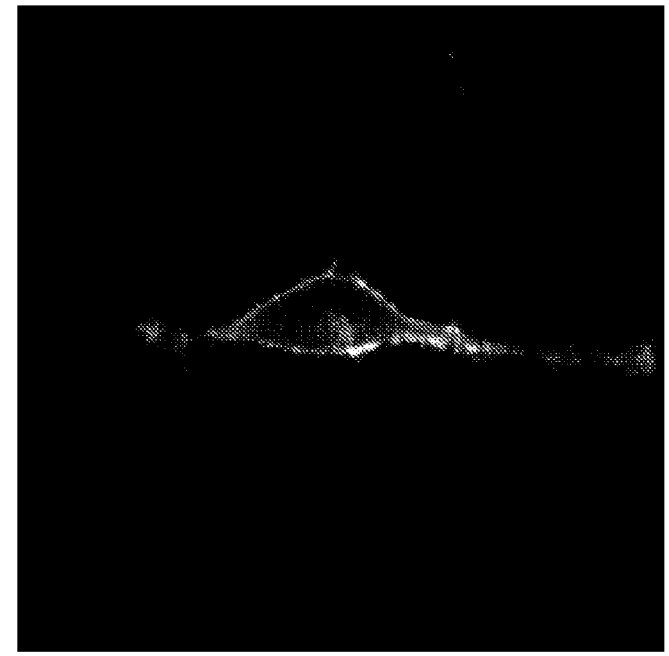
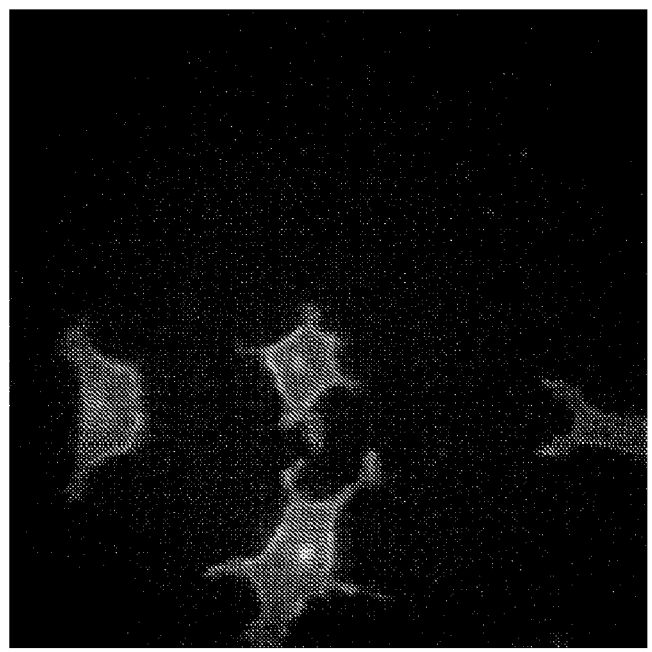
FIG. 4

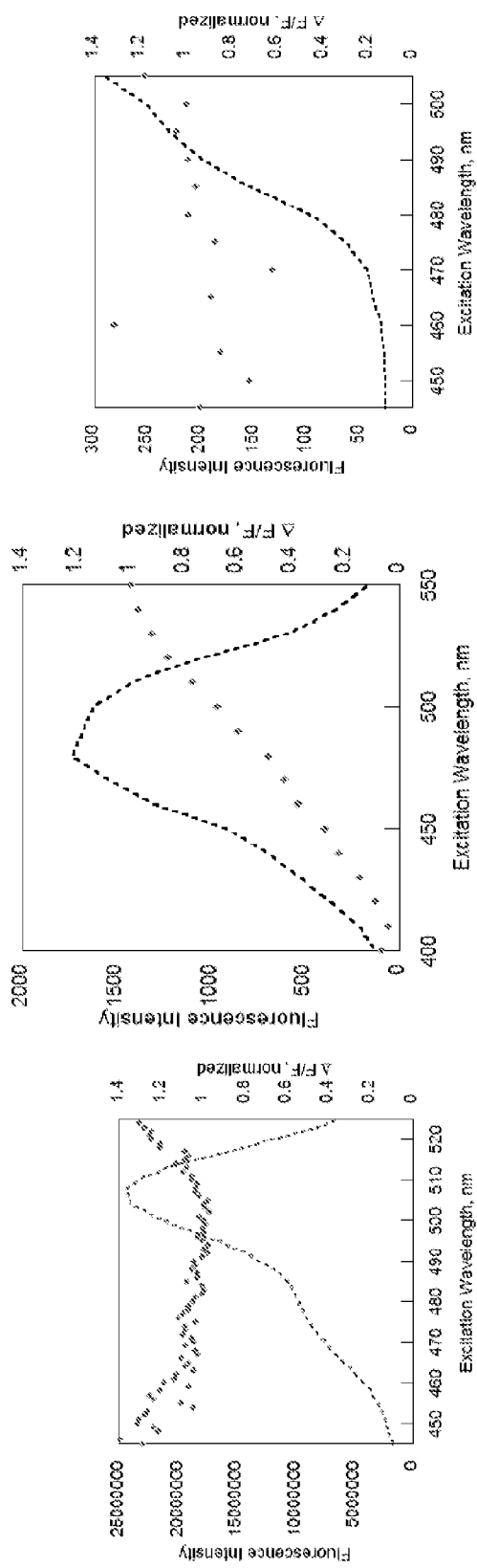

FLUORESCENT PROBES FOR MONITORING VOLTAGE BY PHOTO-INDUCED ELECTRON TRANSFER

CROSS REFERENCES TO APPLICATIONS

This application is a 371 of International Patent Application No. PCT/US2012/038876, filed May 21, 2012, which claims priority to U.S. Provisional Patent Application Ser. No. 61/488,075, filed May 19, 2011, the disclosures of which are hereby incorporated herein by reference in its entireties for all purposes.

STATEMENT OF GOVERNMENT SUPPORT

This invention was made with government support under grants NS027177 and EB012423 awarded by NIH. The government has certain rights in the invention.

BACKGROUND OF THE INVENTION

Fluorescence imaging can map the electrical activity and communication of multiple spatially resolved neurons and thus complement traditional electrophysiological measurements (1, 2). $Ca^{2+}$ imaging is the most popular of such techniques, because the indicators are well-developed (3-6), highly sensitive (5, 6), and genetically encodable (7-13), enabling investigation of the spatial distribution of $Ca^{2+}$ dynamics in structures as small as dendritic spines and as large as functional circuits. However, because neurons translate depolarizations into $Ca^{2+}$ signals via a complex series of pumps, channels, and buffers, fluorescence imaging of $Ca^{2+}$ transients cannot provide a complete picture of electrical activity in neurons. Observed $Ca^{2+}$ spikes are temporally low-pass filtered from the initial depolarization and provide limited information regarding hyperpolarizations and sub-threshold events. Therefore, while fluorescence imaging of $Ca^{2+}$ can provide spatial resolution at the sub- and supra-cellular level, the signals are downstream of the action potential, difficult to resolve in fast spiking neurons, buffered by the indicators themselves, and biased toward post-threshold events.

Direct measurement of transmembrane potential with fluorescent indicators would provide a more accurate account of the timing and location of neuronal activity. Despite the promise of fluorescent voltage-sensitive dyes (VSDs), previous classes of VSDs have been hampered by some combination of insensitivity, slow kinetics (14-16), heavy capacitative loading (17-21), lack of genetic targetability, or phototoxicity. Two of the more widely used classes of VSDs, electrochromic and FRET dyes, illustrate the problems associated with developing fast and sensitive fluorescent VSDs.

Electrochromic dyes respond to voltage through a direct interaction between the chromophore and the electric field (FIG. 1A). This Stark effect leads to small wavelength shifts in the absorption and emission spectrum. Because the electric field directly modulates the energy levels of the chromophore, the kinetics of voltage sensing occur on a timescale commensurate with absorption and emission, resulting in ultrafast (fs to ps) hypso- or bathochromic shifts many orders-of-magnitude faster than needed to resolve fast spiking events and action potentials in neurons. The small wavelength shift dictates that the fluorescence signal can be best recorded at the edges of the spectrum, where intensity varies most steeply as a function of wavelength. The largest linear responses are −28% ΔF/F per 100 mV (22), although more typical values are ~10% per 100 mV (23, 24). Photo-induced electron transfer (PeT)-based $Ca^{2+}$ probes, such as fluo-3, give ΔF/F values of up to 150% for action potentials in cultured hippocampal neurons (25). Therefore, although electrochromic dyes can keep pace with fast voltage oscillations in neurons, their insensitivity limits the systems in which these dyes can successfully report on voltage changes.

FRET-based voltage sensors use lipophilic anions that intercalate into the cellular membrane and redistribute between the inner and outer leaflets depending upon the transmembrane potential (FIG. 1B). The Nernstian distribution is monitored by a second fluorophore immobilized on one side of the membrane, which undergoes FRET preferentially with the mobile anions on the same side of the membrane. Translocation of the lipophilic anion through the lipid bilayer governs the kinetics of voltage sensing, which can be in the millisecond range. Although these two-component systems can give large changes in intensity (5-34%) (21) or ratio (80% per 100 mV) (15), the operative mechanism relies on translocation of mobile charges in the plasma membrane, thus introducing a capacitative loading problem and resulting in slow response times.

In view of the above drawbacks, methods and compositions are needed which are sensitive to small variations in transmembrane potentials and can respond both to rapid, preferably on a millisecond timescale, and sustained membrane potential changes. Also needed are methods and compositions less susceptible to capacitative loading issues and capable of providing a ratiometric fluorescence signal. The present invention fulfills these and other needs.

SUMMARY OF THE INVENTION

Compounds and methods of the present invention employ a unique mechanism for voltage sensing, i.e. photo-induced electron transfer through molecular wires. The present invention circumvents art-recognized constraints set by the principle of exponential distance dependence of electron transfer to permit intramolecular, photo-inducible electron transfer (PeT) to occur at greater distances, thereby allowing voltage detection to take place across a larger fraction of a cellular membrane. The design of the compound, i.e. a molecular wire joining the fluorophore and inducible quencher moieties described herein, changes the mechanism of electron transfer from superexchange at close distances to electron hopping at larger distances. Efficiency of PeT between the fluorophore and inducible quencher moieties is altered in response to different voltage conditions, e.g. ranging from the potential at hyperpolarized state to depolarized state in the context of a cellular membrane. Quenching of the fluorescent moiety by the quencher moiety modulates the fluorescence quantum yield independent of wavelength, thereby permitting more efficient use of photons for excitation and emission, and lowering the operative parameters for light levels and dye concentrations.

Unlike conventional detection methods involving FRET dyes, compounds of the present invention place little to no capacitative load on the membrane and do not affect neuronal excitability. Other features exhibited by the compounds described herein include wavelength-independent sensitivity, fast response to changes in voltage in pace with biological fluctuations, slowed photobleaching, reduced phototoxicity, genetic targetability, and synthetic tractability for chemical modification. See Table 1 below outlining the various advantages of PeT-based dyes over electrochromic or FRET-based methods for voltage sensing. Since the quenching mechanism used by these compounds alters the $\Phi_{Fl}$, decreases the brightness of the fluorophore, and does not shift the wavelength as do electrochromic methods, lower intensity light can be used, thereby reducing phototoxicity and permitting longer experimental duration. Those familiar with the art will know that electrochromic dyes require the entire voltage-sensing chromophores to be rigid in order to enable π orbital overlap, quantum yield, efficient charge transfer, and maximization of voltage sensitivity. Such rigidity in turn hinders synthesis and water solubility. The presently described PeT compounds are not subject to these constraints as the molecular wire need not be rigidly coplanar to function and synthesis of longer wires is feasible and sensitivity-enhancing, a phenomenon not observed with electrochromic dyes. Furthermore, the efficiency of PeT can be tuned via rational selection of the electron affinities of the donor, wire, and acceptor to maximize fluorescence turn-on in response to depolarizations.

TABLE 1

Summary of attributes

| Attribute | Electrochromic | FRET | PeT |
| --- | --- | --- | --- |
| Nature of translocating charge | Electron | Lipid soluble anion | Electron |
| Forward charge shift occurs when | Photon absorption | Membrane depolarization | Quenching |
| Reverse charge shift occurs when | Photon emission or radiation-less decay | Membrane repolarization | Electron-hole recombination |
| Fractional charge × Fraction of total voltage | ~0.1 | 0.4-0.6 | ~0.5 |
| Δ energy for 100 mV ΔV | 0.003-0.02 eV | 0.06 eV | 0.05 eV |
| Comparison energy | Photon energy 1.5-2 eV | kT 0.026 eV | kT 0.026 eV |
| Extended rigid fluorophore needed? | Yes | No | No |
| Use full ex/em band | No | Yes | Yes |
| Sensitivity Δ F/F per mV | Low | High | High |
| Speed | fs | ms-s | ns-μs |
| Capacitative loading | None | Significant | None |

One aspect of the invention provides a compound having a structure according to the formula:

E-M-A wherein A is a fluorophore selected from the group consisting of xanthenes, coumarins, cyanines, and bimanes. A is charged at physiological pH. M is a molecular wire. E is a hydrophobic moiety. A and E are capable of being involved in a photo-induced electron transfer that quenches the fluorescence of A in response to a voltage condition.

In some embodiments, the compound is not:

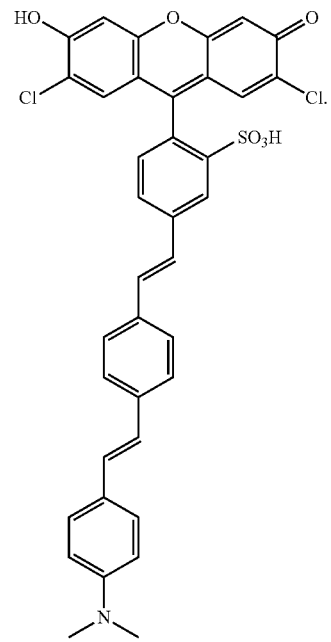 [SMILES: CN(C)c1ccc(/C=C/c2ccc(/C=C/c3ccc(-c4c5cc(Cl)c(=O)cc-5oc5cc(O)c(Cl)cc45)c(S(=O)(=O)O)c3)cc2)cc1]

In some embodiments, A is an electron acceptor and E is an electron donor in said photo-induced electron transfer.

In some embodiments, A is an electron donor and E is an electron acceptor in said photo-induced electron transfer.

In some embodiments, A is negatively charged at physiological pH.

In some embodiments, A is selected from xanthenes.

In some embodiments, A has a structure according to the formula:

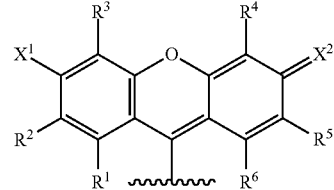

wherein $R^1$, $R^2$, $R^3$, $R^4$, $R^5$, and $R^6$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $X^1$ is selected from $Z^2R^{12}$ and $NR^{11}R^{12}$. $X^2$ is selected from $NR^{13}R^{14}$ and O. $R^{12}$ is selected from H, alkyl, substituted alkyl, heteroalkyl, substituted heteroalkyl, and $C(Z^3)R^{15}$. $R^{13}$ and $R^{15}$ are independently selected from alkyl, substituted alkyl, heteroalkyl, substituted heteroalkyl, $OR^{16}$ and $NR^{17}R^{18}$. $R^{16}$ is selected from H, alkyl, substituted alkyl, heteroalkyl, substituted heteroalkyl, aryl, substituted aryl, heteroaryl, substituted heteroaryl and $C(O)R^{19}$. $R^{19}$ is selected from alkyl, substituted alkyl, heteroalkyl and substituted heteroalkyl. $R^{11}$, $R^{13}$, $R^{14}$, $R^{17}$ and $R^{18}$ are independently selected from H, alkyl, substituted alkyl, heteroalkyl and substituted heteroalkyl. $Z^1$ and $Z^3$ are independently selected from O, S and NH. $Z^2$ is selected from O and S.

In some embodiments, A has a structure according to the formula:

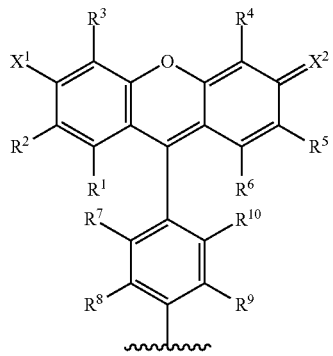

wherein $R^7$, $R^8$, $R^9$, and $R^{10}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $R^{11}$, $R^{12}$, $R^{13}$, $Z^1$, and $Z^2$ are as defined herein.

In some embodiments, $X^1$ is OH, $X^2$ is O, $R^2$ is Cl, $R^5$ is Cl and $R^{10}$ is $SO_3H$.

In some embodiments, $R^1$, $R^3$, $R^4$, and $R^6$ are H.

In some embodiments, $R^7$, $R^8$ and $R^9$ are H.

In some embodiments, E is selected from a substituted aryl and substituted heteroaryl.

In some embodiments, E is phenyl substituted with an amine.

In some embodiments, E has the structure according to the formula:

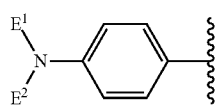

wherein $E^1$ and $E^2$ are independently alkyl. In some embodiments, $E^1$ and $E^2$ are independently selected from unsubstituted $C_1$-$C_6$ alkyl. In some embodiments, $E^1$ and $E^2$ are independently selected from methyl and butyl. In some embodiments, $E_1$ and $E_2$ are butyl. In some embodiments, the butyl is n-butyl.

In some embodiments, M is selected from alkylene, substituted alkylene, heteroalkylene, substituted heteroalkylene, arylene, substituted arylene, heteroarylene and substituted heteroarylene.

In some embodiments, M has a structure according to the formula:

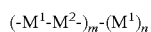

wherein $M^1$ is alkylene; $M^2$ is arylene; m is an integer selected from 0, 1, 2, 3, 4, 5, 6, 7, 8, 9, 10, 11, 12, 13, 14, 15, 16, 17, 18, 19 and 20; n is an integer selected from 0 and 1; and at least one of m and n is greater than 0.

In some embodiments, M has a structure according to the formula:

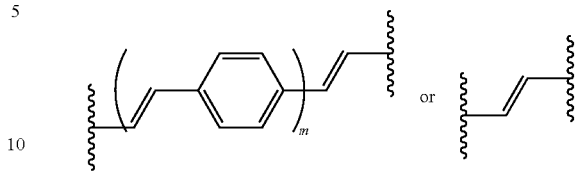

wherein m is an integer selected from 0, 1, 2, 3, 4, 5, 6, 7, 8, 9, 10, 11, 12, 13, 14, 15, 16, 17, 18, 19 and 20.

In some embodiments, M is a conjugated system.

In some embodiments, M is hydrophobic.

In some embodiments, the compound has a structure selected from:

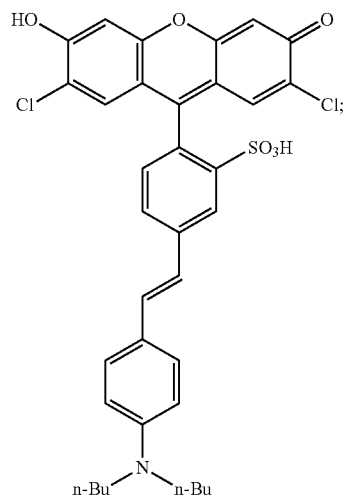

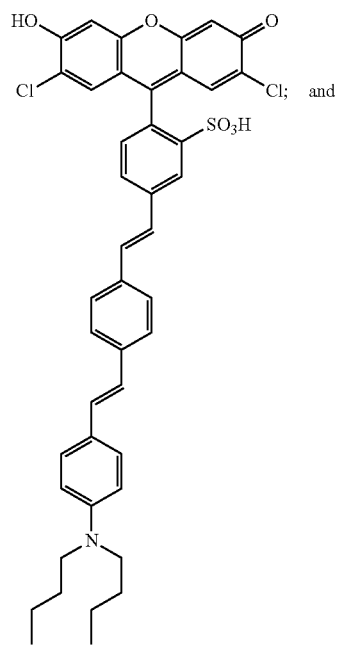

and

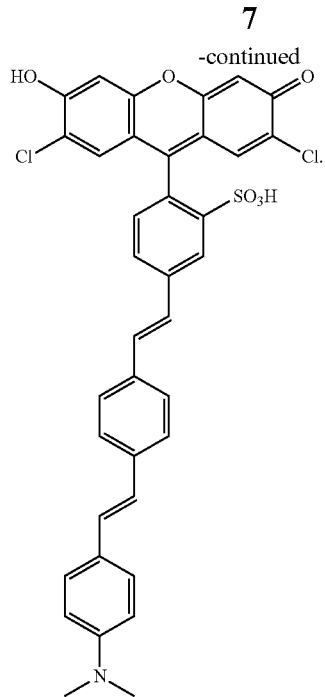

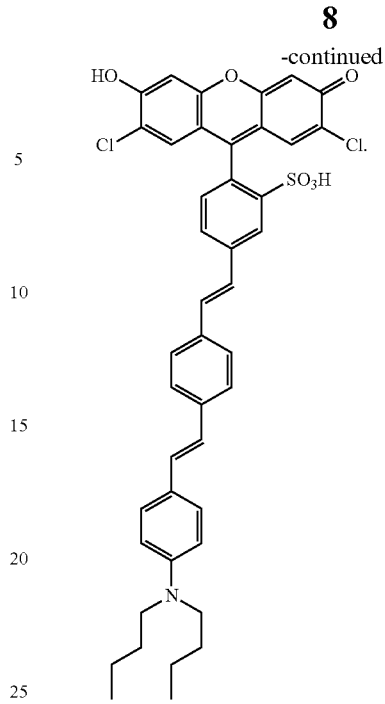

In some embodiments, the compound has a structure selected from:

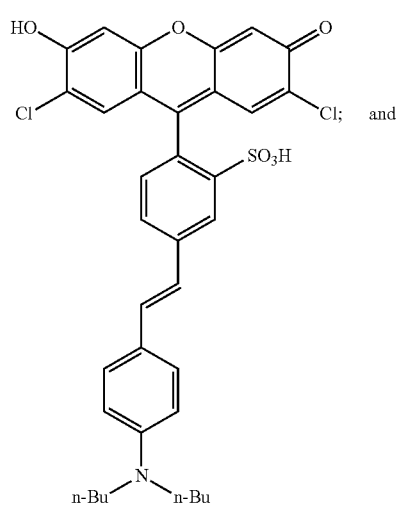

and

In some embodiments, the compound is substituted with a targeting moiety. In some embodiments, the targeting moiety is selected from a nucleic acid, a peptide, a saccharide, a lipid and a combination thereof. In some embodiments, the targeting moiety is specific for an excitable cell type. In some embodiments, the excitable cell type is selected from a neuron, a nerve cell, a lymphocyte, an endocrine secretory cell, a neuroendocrine secretory cell, a cardiac muscle cell, a smooth muscle cell, a skeletal muscle cell, and a mast cell.

In another aspect, the invention provides an amphipathic compound having the structure:

E-M-A wherein A is a charged fluorophore selected from the group consisting of xanthenes, coumarins, cyanines, and bimanes. M is a molecular wire. E is an electron-rich, hydrophobic moiety capable of a photo-induced electron transfer to A through the molecular wire, which quenches the fluorescence of A in response to a voltage condition.

In some embodiments, the compound is not:

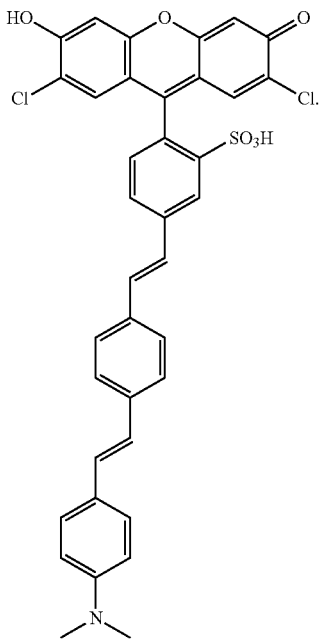

In some embodiments, A is a positively charged fluorophore.

In some embodiments, A is a negatively charged fluorophore.

In some embodiments, A is selected from xanthenes.

In some embodiments, A has a structure according to the formula:

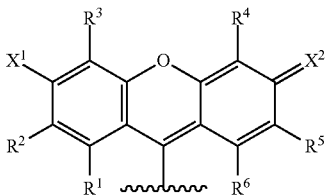

wherein $R^1$, $R^2$, $R^3$, $R^4$, $R^5$, and $R^6$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $X^1$ is selected from $Z^2R^{12}$ and $NR^{11}R^{12}$. $X^2$ is selected from $NR^{13}R^{14}$ and O. $R^{12}$ is selected from H, alkyl, substituted alkyl, heteroalkyl, substituted heteroalkyl, and $C(Z^3)R^{15}$. $R^{13}$ and $R^{15}$ are independently selected from alkyl, substituted alkyl, heteroalkyl, substituted heteroalkyl, $OR^{16}$ and $NR^{17}R^{18}$. $R^{16}$ is selected from H, alkyl, substituted alkyl, heteroalkyl, substituted heteroalkyl, aryl, substituted aryl, heteroaryl, substituted heteroaryl and $C(O)R^{19}$. $R^{19}$ is selected from alkyl, substituted alkyl, heteroalkyl and substituted heteroalkyl. $R^{11}$, $R^{13}$, $R^{14}$, $R^{17}$ and $R^{18}$ are independently selected from H, alkyl, substituted alkyl, heteroalkyl and substituted heteroalkyl. $Z^1$ and $Z^3$ are independently selected from O, S and NH. $Z^2$ is selected from O and S.

In some embodiments, A has a structure according to the formula:

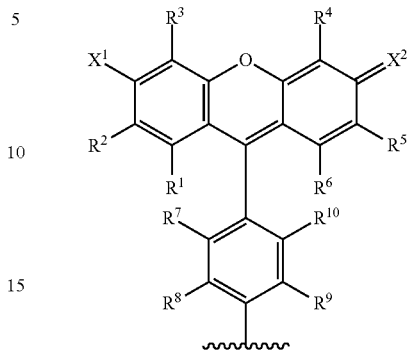

wherein $R^7$, $R^8$, $R^9$, and $R^{10}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $R^{11}$, $R^{12}$, $R^{13}$, $Z^1$, and $Z^2$ are as defined herein.

In some embodiments, $X^1$ is OH, $X^2$ is O, $R^2$ is Cl, $R^5$ is Cl and $R^{10}$ is $SO_3H$.

In some embodiments, $R^1$, $R^3$, $R^4$, and $R^6$ are H.

In some embodiments, $R^7$, $R^8$ and $R^9$ are H.

In some embodiments, E is selected from a substituted aryl and substituted heteroaryl.

In some embodiments, E is phenyl substituted with an amine.

In some embodiments, E has the structure according to the formula:

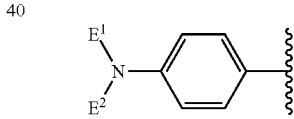

wherein $E^1$ and $E^2$ are independently alkyl. In some embodiments, $E^1$ and $E^2$ are independently selected from unsubstituted $C_1$-$C_6$ alkyl. In some embodiments, $E^1$ and $E^2$ are independently selected from methyl and butyl. In some embodiments, $E_1$ and $E_2$ are butyl. In some embodiments, butyl is n-butyl.

In some embodiments, M is selected from alkylene, substituted alkylene, heteroalkylene, substituted heteroalkylene, arylene, substituted arylene, heteroarylene and substituted heteroarylene.

In some embodiments, M has a structure according to the formula:

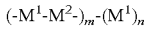

wherein $M^1$ is alkylene; $M^2$ is arylene; m is an integer selected from 0, 1, 2, 3, 4, 5, 6, 7, 8, 9, 10, 11, 12, 13, 14, 15, 16, 17, 18, 19 and 20; n is an integer selected from 0 and 1; and at least one of m and n is greater than 0.

In some embodiments, M has a structure according to the formula:

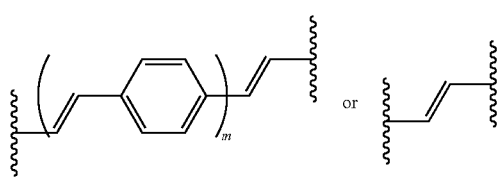
wherein m is an integer selected from 0, 1, 2, 3, 4, 5, 6, 7, 8, 9, 10, 11, 12, 13, 14, 15, 16, 17, 18, 19 and 20.
In some embodiments, M is a conjugated system.
In some embodiments, M is hydrophobic.
In some embodiments, the amphipathic compound has a structure selected from:
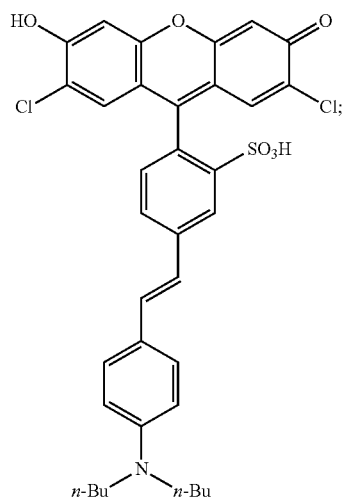
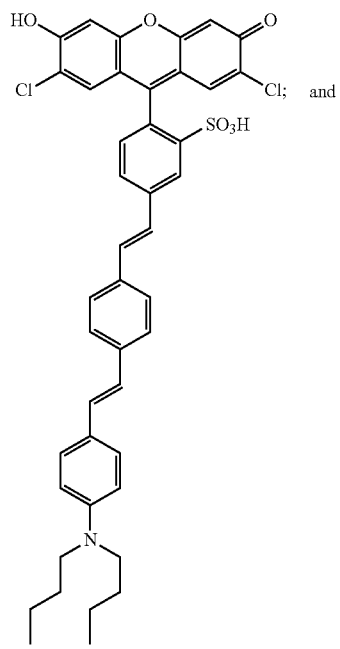
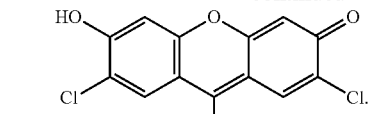
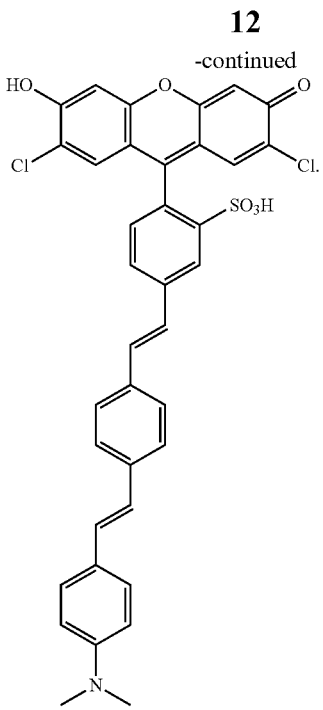
In some embodiments, the amphipathic compound has a structure selected from:

-continued

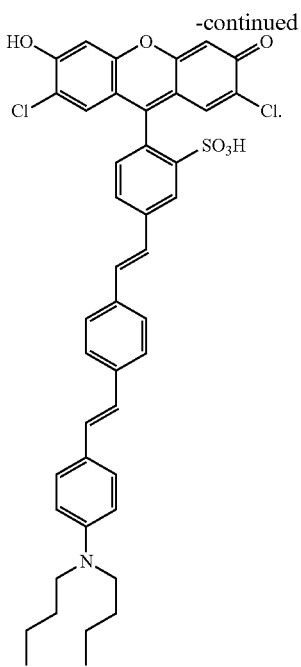

In some embodiments, the amphipathic compound is substituted with a targeting moiety.

In some embodiments, the targeting moiety is selected from a nucleic acid, a peptide, a saccharide, a lipid and a combination thereof. In some embodiments, the targeting moiety is specific for an excitable cell type. In some embodiments, the excitable cell type is selected from a neuron, a nerve cell, an endocrine secretory cell, a neuroendocrine secretory cell, a cardiac muscle cell, a smooth muscle cell, a skeletal muscle cell.

In another aspect, the invention provides a composition comprising a living cell, wherein the cell has a membrane comprising a compound disclosed herein.

In some embodiments, the living cell is a mammalian cell. In some embodiments, the living cell is an excitable cell type. In some embodiments, the excitable cell type is selected from a neuron, a nerve cell, an endocrine secretory cell, a neuroendocrine secretory cell, a cardiac muscle cell, a smooth muscle cell, a skeletal muscle cell. In some embodiments, the cell is selected from a HEK293 cell and a neuron.

In some embodiments, the membrane is the plasma membrane of the cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

In another aspect, the invention provides a method for monitoring transmembrane potential of a living cell, comprising:
   a. introducing a plurality of a compound disclosed herein into a sample comprising a living cell under conditions that permit the interaction of said plurality of compound with a plasma membrane of said cell;
   b. exciting the compound with light of a wavelength sufficient to excite the fluorophore portion of the compound described herein;
   c. detecting fluorescence emission from the plurality of the compound; and
   d. correlating said fluorescence emission to the transmembrane potential of the living cell,
   e. wherein the quenching of fluorescence emitted by the plurality of the compound is altered in response to a change in the membrane potential.

In some embodiments, the living cell is a mammalian cell.

In some embodiments, the living cell is an excitable cell type.

In some embodiments, the excitable cell type is selected from a neuron, a nerve cell, an endocrine secretory cell, a neuroendocrine secretory cell, a cardiac muscle cell, a smooth muscle cell, a skeletal muscle cell.

In some embodiments, the cell is selected from a HEK293 cell and a neuron.

In some embodiments, the membrane is the plasma membrane of said cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

In another aspect, the invention provides a method of identifying a test chemical that modulates transmembrane potential in at least one cell, said method comprising the steps:
   a. contacting said at least one cell with a plurality of a compound disclosed herein, wherein said cell has a membrane;
   b. exposing the membrane to said test chemical;
   c. exciting the compound with light of a wavelength sufficient to excite the fluorophore portion of the compound disclosed herein;
   d. detecting fluorescence emission of said plurality of the compound;
   e. correlating said fluorescence emission to transmembrane potential of the cell; and
   f. comparing said transmembrane potential to a control value, wherein a difference between said transmembrane potential and the control value is indicative of the test chemical's ability to modulate transmembrane potential of said cell.

In some embodiments, the cell is a living cell.

In some embodiments, the living cell is a mammalian cell.

In some embodiments, the living cell is an excitable cell type.

In some embodiments, the excitable cell type is selected from a neuron, a nerve cell, an endocrine secretory cell, a neuroendocrine secretory cell, a cardiac muscle cell, a smooth muscle cell, a skeletal muscle cell.

In some embodiments, the cell is selected from a HEK293 cell and a neuron.

In some embodiments, the membrane is the plasma membrane of said cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

DESCRIPTION OF THE DRAWINGS

More particular descriptions of the invention are made by reference to certain exemplary embodiments thereof which are illustrated in the appended Figures. These Figures form a part of the specification. It is to be noted, however, that the appended Figures illustrate exemplary embodiments of the invention and therefore are not to be considered limiting in their scope.

FIG. 4 provides epifluorescence (left) and confocal (right) images of HEK cells loaded with 2 μM of VF2.4.Cl.

FIG. 6 shows the normalized Δ F/F vs. excitation wavelength for Calcium Green 1 (FIG. 6A), di-4-ANEPPS (FIG. 6B), and VF2.4.Cl (FIG. 6C).

DESCRIPTION OF THE INVENTION

Figure 1:
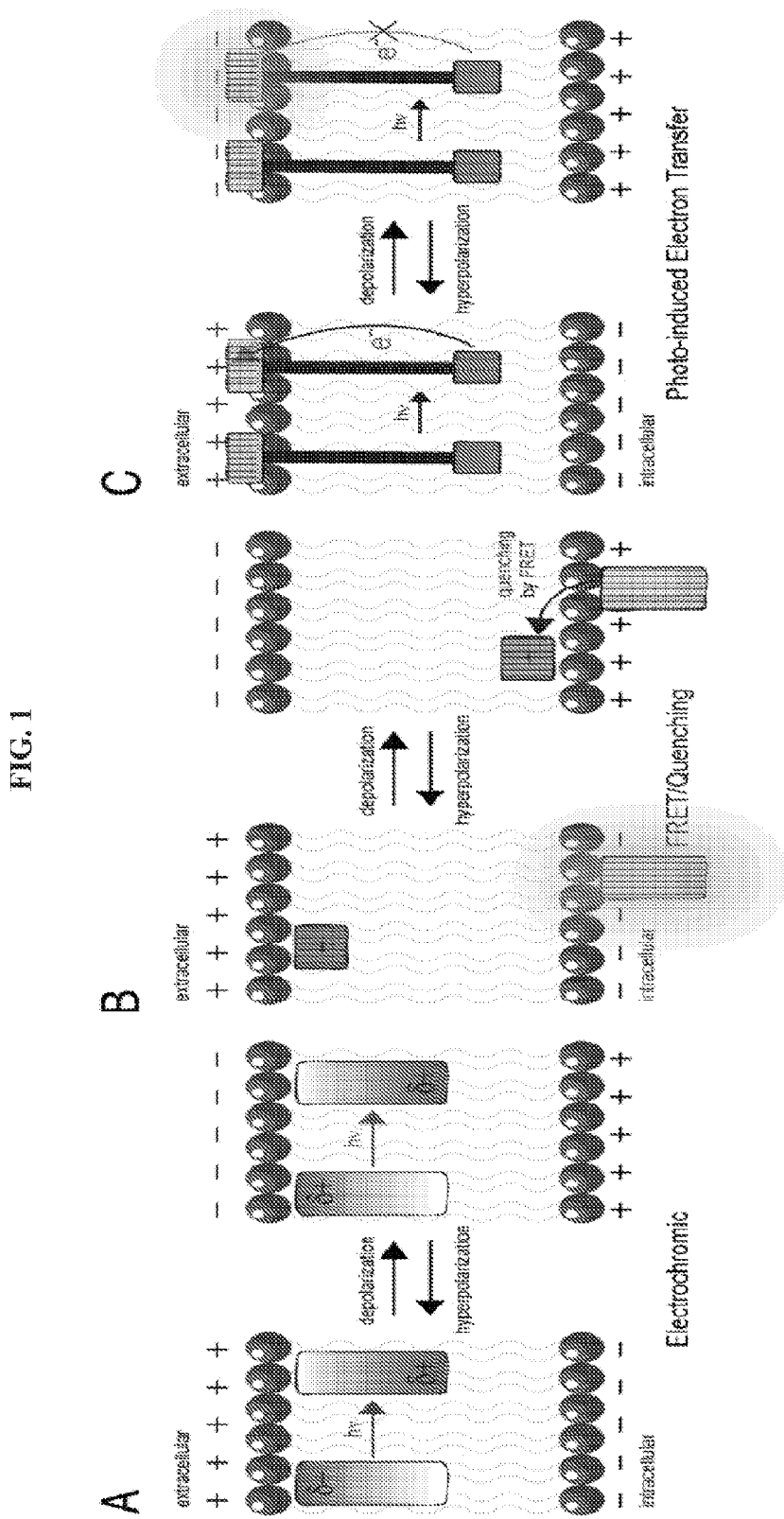
FIG. 1 illustrates various mechanisms of fluorescent voltage sensing. (A) Electrochromic VSDs sense voltage through the Stark effect, whereby the chromophore interacts directly with the electric field. Absorption of a photon significantly alters the excited state molecular dipole, which at hyperpolarizing potentials is stabilized (Left). At depolarizing potentials the charge shift inverted state is destabilized (Right). Changes in the energy levels of the chromophore result in small spectral shifts in the emission of the dye. (B) FRET-pair voltage sensors use lipophilic anions (striped), which partition in a voltage-dependent fashion on the inner or outer leaflet of the membrane. Depolarization causes translocation of the anion, which can now quench the fluorescence of an immobilized fluorophore (green). (C) Molecular wire PeT VSDs depend upon the voltage-sensitive electron transfer from an electron-rich donor (gray) through a membrane-spanning molecular wire (black) to a fluorescent reporter (striped). At hyperpolarizing potentials, the electric field is aligned antiparallel to the direction of electron transfer, resulting in efficient PeT and quenched fluorescence (Left). Depolarization aligns the electric field in the direction of PeT, decreasing the rate of electron transfer and increasing fluorescence (Right).
Figure 2:
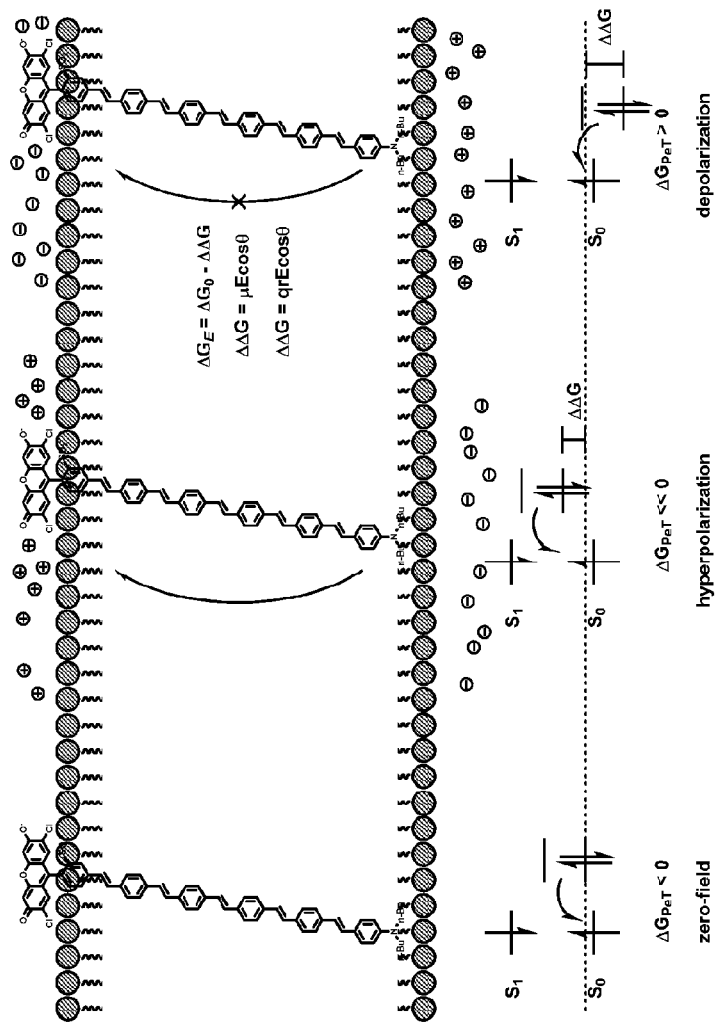
FIG. 2 provides a schematic representation of eT VSD in a membrane at zerofield, hyper-, and de-polarizing potentials. In the absence of an electric field, the probe is quenched by directional eT from the aniline donor to fluorescent acceptor. Application of a hyperpolarizing field increases eT and decreases fluorescence. Depolarizing potentials decrease eT and increase fluorescence by stabilizing the electron-rich donor.

The present invention operates based on a unique mechanism for voltage sensing, i.e. PeT through molecular wires. In these PeT sensors, a fluorescent reporter connects to a quencher via a molecular wire, which minimizes the exponential distance dependence of intramolecular electron transfer (26) and allows efficient electron transfer over a major fraction of the thickness of the plasma membrane. At resting or hyperpolarized potentials, the transmembrane electric field promotes electron transfer from the quencher to the excited-state fluorophore through the molecular wire, quenching fluorescence (See FIG. 1C). Depolarization reverses the electric field, hinders electron transfer, and brightens fluorescence (27), just as $Ca^{2+}$ binding dequenches indicators like fluo-3 (28). Electron transfer occurs within picoto nanoseconds after photon absorption and returns to its initial state within a microsecond (26, 29), slower than the electrochromic mechanism but essentially instantaneous on a biological timescale. Because electron transfer reverses quickly and is driven by photon absorption rather than membrane potential changes, capacitative loading should be negligible, as calculated in the SI Appendix. A full electronic charge traverses a Marcus-type thermal activation barrier to sense a large fraction of the membrane voltage, making voltage sensitivity high (30). Quenching of the fluorescent reporter by the electron-rich donor modulates the fluorescence quantum yield independent of wavelength, permitting efficient use of photons for excitation and emission, allowing lower light levels or dye concentrations to be used.

I. DEFINITIONS

The term "membrane potential" or "transmembrane potential" refers to the electric potential difference across the membrane of a cell. The membrane may be selected from a plasma membrane, mitochondrial membrane, and a chloroplast membrane. In preferred embodiments, the membrane is a plasma membrane.

A "fluorophore" refers to a molecule or molecular moiety that emits fluorescence.

A "moiety" refers to a radical of a molecule that is attached to the remainder of the molecule.

The term "molecular wire," in the context of the present invention, refers to a molecular moiety that permits the flow of electrons from one end to the other end of the moiety. In some embodiments of the invention, the molecular wire employed is not an electroactive polymers, which themselves may donate or accept electrons. In various embodiments of the invention, the molecular wire is not a nucleic acid. In still other embodiments, the molecular wire is neither an electroactive polymer nor a nucleic acid. In exemplary embodiments, the molecular wire has substantially overlapping π-orbitals, i.e. conjugated π-orbitals, as between the monomeric units of the molecular wire, although the molecular wire may also contain other types of molecular orbitals. In some embodiments, the molecular wire of the invention is capable of transferring electrons at 100 Hz.

In a preferred embodiment, the molecular wire of the present invention has a conductivity, S, of from between about $10^{-6}$ to about $10^{4}$ $\Omega^{-1}cm^{-1}$, with from about $10^{-5}$ to about $10^{3}$ $\Omega^{-1}cm^{-1}$ being preferred, with these S values being calculated for molecules ranging from about 20Å to about 200 Å. As described below insulators have a conductivity S of about $10^{-7}$ $\Omega^{-1}cm^{-1}$ or lower, with less than about $10^{-8}$ $\Omega^{-1}cm^{-1}$ being preferred. See generally Gardner et al., Sensors and Actuators A 51 (1995) 57-66, incorporated herein by reference.

As used herein, a "quencher" or "quenching group" refers to a molecular entity or group within a molecular entity, respectively, that can attenuate at least partly the light emitted by a fluorophore or fluorescent group. This attenuation is referred to herein as "quenching". Hence, illumination of the fluorescent group in the presence of the quenching group leads to an emission signal of lower intensity than would otherwise occur in the absence of the quenching group, or the absence of an emission signal. Quenching can occur by mechanism of energy transfer, charge transfer, intersystem crossing, electron exchange, photo-induced electron transfer, or chemical reaction.

In quenching by photo-induced electron transfer (PeT), there is an electron donor and an electron acceptor and the excited fluorophore can be either the electron donor or electron acceptor. Where the excited state of a fluorophore acts as an electron acceptor, an electron-rich species can donate electron(s) to the photo-induced electron acceptor and thereby quench the fluorescence of the fluorophore. Alternatively, PeT quenching can also occur by electron transfer from the excited fluorophore to the quencher, e.g. an electron-deficient species, an electronegative halocarbon, etc. See *Principles of Fluorescence Spectroscopy*, 3ed. (2006) by Joseph Lakowicz, Springer Science+Business Media, LLC: New York. In both forms of PeT, the extra electron on the acceptor is returned to the electron donor.

The term "voltage condition," in the context of the present invention, is used in reference to the voltage condition of a cell membrane. Examples of membrane voltage conditions may range from the resting potential characteristic of a given cell in some embodiments to a transmembrane potential falling within an action potential of a given cell, e.g. between hypolarized state to depolarized state.

An "excitable cell type," as used herein, refers to a cell type capable of generating action potentials. Exemplary excitable cell types include, without limitation, nerve cells, endocrine secretory cells, neuroendocrine secretory cells, and muscle cells. The cells may be primary cultures that are set up for short term growth. Such primary cultures can provide highly reproducible results from one culture to another. Alternatively, cell lines are used. Cell lines are generally able to be passaged in culture for extended periods of time. They include, without limit, immortalized cells, stem cells, etc., where the stem cells are able to differentiate into excitable cells suitable for the subject methods. Examples of cultured excitable cells include, but are not limited to, suprachiasmatic neurons (Walsh et al. (1995)

Neuroscience 69(3):915-29); motoneuronal cultures (Zoran et al. (1996) Dev Biol 179(1):212-22); cardiac tissue (Fast and Kleber (1995) Cardiovasc Res 29(5):697-707); cardiac ventricular myocytes; Schackow et al. (1995) Am J Physiol 268(4 Pt 1):C1002-17; electrogenic myocardiac cells (Connolly et al. (1990) Biosens Bioelectron 5(3):223-34).

A "control" sample or value refers to a sample or value that serves as a reference, usually a known reference, for comparison to a test sample or value. For example, in the context of the present invention, a control value for the transmembrane potential of a given cell type can be an average value gathered from a population of cells of that specific cell type, e.g., HEK, neuronal cell. One of skill in the art will understand which controls are valuable in a given situation and be able to analyze data based on comparisons to control values. Controls are also valuable for determining the significance of data. For example, if values for a given parameter vary widely in controls, variation in test samples will not be considered as significant.

The term "voltage clamp" or "voltage-clamped," refers to a biophysical technique which allows one to control the potential across a cell membrane with a feedback amplifier. For a review of commonly known voltage clamp methods, see *Microelectrode Techniques*, Ogden D (ed.) Cambridge (1987): Chapter 2—Voltage clamp techniques, by Halliwell et al.

A "cell membrane" or "cellular membrane," in the context of the present invention, refers to a plasma membrane or the membrane of any cellular organelle, such as the Golgi, mitochondria, chloroplast, and endoplasmic reticulum. In preferred embodiments, the cell membrane refers to the plasma membrane.

The "inner layer" of a cell membrane, as used herein, refers to the one of two leaflets in a cellular membrane which has a hydrophilic surface directed away from the extracellular environment. To illustrate, the inner layer of a plasma membrane refers to the cytosolic leaflet.

The "outer layer" of a cell membrane, as used herein, refers to the one of two leaflets in a cellular membrane which has a hydrophilic surface directed towards the extracellular environment. To illustrate, the outer layer of a plasma membrane refers to the exoplasmic leaflet.

In some embodiments, the compounds herein additionally include a "localization sequence," "targeting sequence," or "targeting moiety" to direct the compound to a particular organelle or cellular membrane of the cell. Targeting moieties and other molecular moieties useful in the present invention can include those known in the art, such as in WO/2001/04221.

The term "agent" as used herein, describes any molecule. Candidate agents that can be employed with the screening methods described herein can encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including nucleic acids, e.g. ribozymes, deoxyribozymes, peptides, saccharides, fatty acids, steroids, purines, pyrimidines, derivatives, structural analogs or any combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The symbol ⌇, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain hydrocarbon radical, which may be fully saturated, mono- or polyunsaturated and includes mono-, di- (i.e., alkylene) and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups that are limited to hydrocarbon groups are termed "homoalkyl".

Typically, an alkyl group will have from 1 to 24 carbon atoms, with those groups having 10 or fewer carbon atoms being preferred in the present invention. A "lower alkyl" is a shorter chain alkyl, generally having eight or fewer carbon atoms. In some embodiments, alkyl refers to an alkyl selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{25}$ alkyl. In some embodiments, alkyl refers to $C_1$-$C_{20}$ alkyl. In some embodiments, alkyl refers to $C_1$-$C_{15}$ alkyl. In some embodiments, alkyl refers to $C_1$-$C_{10}$ alkyl. In some embodiments, alkyl refers to $C_1$-$C_6$ alkyl.

The term "heteroalkyl," by itself or in combination with another term, means, unless otherwise stated, a stable straight or branched chain, mono-, di- (i.e., heteroalkylene) and multivalent radicals consisting of carbon and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "acyl" refers to a species that includes the moiety —C(O)R, where R has the meaning defined herein.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" includes trifluoromethyl, 2,2,2-trifluoroethyl, 4-chlorobutyl, 3-bromopropyl, and the like.

The term "aryl" means, unless otherwise stated, a polyunsaturated, aromatic, mono-, di- (i.e., arylene) and multivalent radicals that can be a single ring or multiple rings (preferably from 1 to 3 rings), which are fused together or linked covalently. The term "heteroaryl" refers to an aryl group (or ring) that contains from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

In some embodiments, any of alkyl, heteroalkyl, cycloalkyl, heterocycloalkyl, aryl and heteroaryl is optionally substituted. That is, in some embodiments, any of these groups is substituted or unsubstituted. In some embodiments, substituents for each type of radical are selected from those provided below.

Substituents for the alkyl and heteroalkyl radicals are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted heterocycloalkyl, substituted or unsubstituted aryl, substituted or unsubstituted heteroaryl, halogen, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

The term "heteroatom" includes oxygen (O), nitrogen (N), sulfur (S) and silicon (Si).

The symbol "R" is a general abbreviation that represents a substituent group that is selected from acyl, alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl and substituted heteroaryl.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. In some embodiments, the definition of terms used herein is according to IUPAC.

Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

One aspect of the invention provides a compound having a structure according to the formula:

E-M-A wherein A is a fluorophore selected from the group consisting of xanthenes, coumarins, cyanines, and bimanes. A is charged at physiological pH. M is a molecular wire. E is a hydrophobic moiety. A and E are capable of being involved in a photo-induced electron transfer that quenches the fluorescence of A in response to a voltage condition.

In some embodiments, the compound is not:

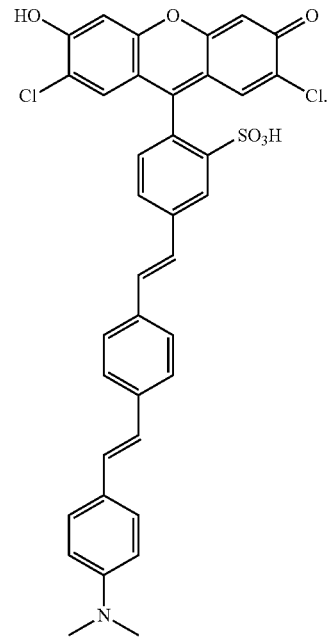 [SMILES: CN(C)c1ccc(/C=C/c2ccc(/C=C/c3ccc(-c4c5cc(Cl)c(=O)cc-5oc5cc(O)c(Cl)cc45)c(S(=O)(=O)O)c3)cc2)cc1]

Xanthenes useful in the present invention may be selected from any known to those of skill in the art, including fluoresceins, rhodamines, and rhodols, according to the guidance provided herein. Exemplary xanthenes known in the art include those described in US2009/0093612, U.S. Pat. No. 7,491,830, and U.S. Pat. No. 734,701.

Coumarins useful in the present invention may be selected from any known to those of skill in the art, according to the guidance provided herein.

Cyanines useful in the present invention may be selected from any known to those of skill in the art, according to the guidance provided herein.

Bimanes, useful in the present invention may be selected from any known to those of skill in the art, according to the guidance provided herein.

In some embodiments, A is an electron acceptor and E is an electron donor in said photo-induced electron transfer.

In some embodiments, A is an electron donor and E is an electron acceptor in said photo-induced electron transfer.

In some embodiments, A is negatively charged at physiological pH.

In some embodiments, A is selected from xanthenes.

In some embodiments, A has a structure according to the formula:

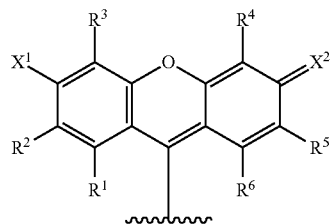

wherein $R^1$, $R^2$, $R^3$, $R^4$, $R^5$, and $R^6$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $X^1$ is selected from $Z^2R^{12}$ and $NR^{11}R^{12}$. $X^2$ is selected from $NR^{13}R^{14}$ and O. $R^{12}$ is selected from H, alkyl, substituted alkyl, heteroalkyl, substituted heteroalkyl, and $C(Z^3)R^{15}$. $R^{13}$ and $R^{15}$ are independently selected from alkyl, substituted alkyl, heteroalkyl, substituted heteroalkyl, $OR^{16}$ and $NR^{17}R^{18}$. $R^{16}$ is selected from H, alkyl, substituted alkyl, heteroalkyl, substituted heteroalkyl, aryl, substituted aryl, heteroaryl, substituted heteroaryl and $C(O)R^{19}$. $R^{19}$ is selected from alkyl, substituted alkyl, heteroalkyl and substituted heteroalkyl. $R^{11}$, $R^{13}$, $R^{14}$, $R^{17}$ and $R^{18}$ are independently selected from H, alkyl, substituted alkyl, heteroalkyl and substituted heteroalkyl. $Z^1$ and $Z^3$ are independently selected from O, S and NH. $Z^2$ is selected from O and S.

In some embodiments, A has a structure according to the formula:

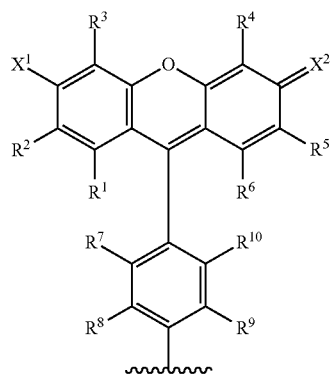

wherein $R^7$, $R^8$, $R^9$, and $R^{10}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $R^{11}$, $R^{12}$, $R^{13}$, $Z^1$, and $Z^2$ are as defined herein.

In some embodiments, $X^1$ is OH, $X^2$ is O, $R^2$ is Cl, $R^5$ is Cl and $R^{10}$ is $SO_3H$.

In some embodiments, $R^1$, $R^3$, $R^4$, and $R^6$ are H.

In some embodiments, $R^7$, $R^8$ and $R^9$ are H.

In some embodiments, E is selected from a substituted aryl and substituted heteroaryl.

In some embodiments, E is phenyl substituted with an amine.

In some embodiments, E has the structure according to the formula:

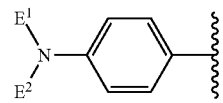

wherein $E^1$ and $E^2$ are independently alkyl. In some embodiments, $E^1$ and $E^2$ are independently selected from unsubstituted $C_1$-$C_6$ alkyl. In some embodiments, $E^1$ and $E^2$ are independently selected from methyl and butyl. In some embodiments, $E_1$ and $E_2$ are butyl. In some embodiments, the butyl is n-butyl.

In some embodiments, M is selected from alkylene, substituted alkylene, heteroalkylene, substituted heteroalkylene, arylene, substituted arylene, heteroarylene and substituted heteroarylene.

In some embodiments, M has a structure according to the formula:

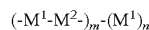

wherein $M^1$ is alkylene; $M^2$ is arylene; m is an integer selected from 0, 1, 2, 3, 4, 5, 6, 7, 8, 9, 10, 11, 12, 13, 14, 15, 16, 17, 18, 19 and 20; n is an integer selected from 0 and 1; and at least one of m and n is greater than 0.

In some embodiments, M has a structure according to the formula:

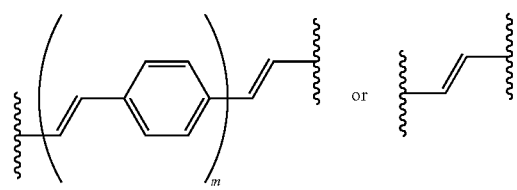

wherein m is an integer selected from 0, 1, 2, 3, 4, 5, 6, 7, 8, 9, 10, 11, 12, 13, 14, 15, 16, 17, 18, 19 and 20.

In some embodiments, M is a conjugated system.

In some embodiments, M is hydrophobic.

In some embodiments, the compound has a structure selected from:

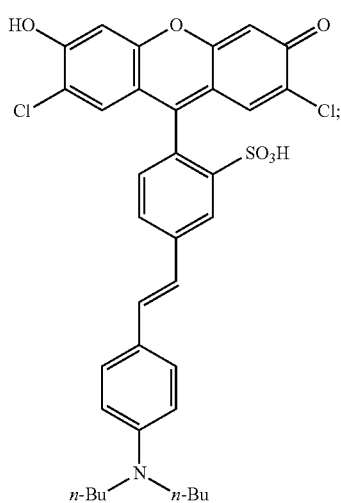
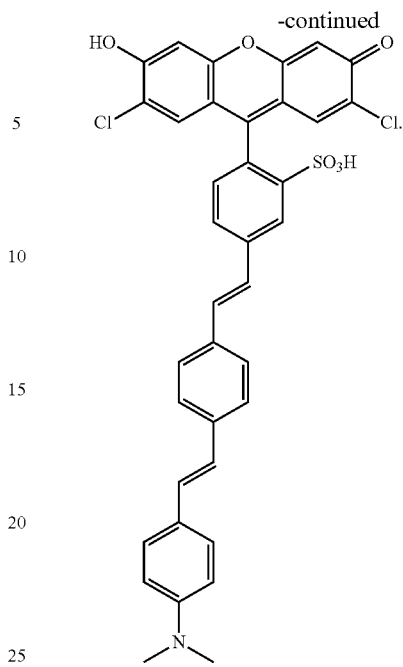
In some embodiments, the compound has a structure selected from:
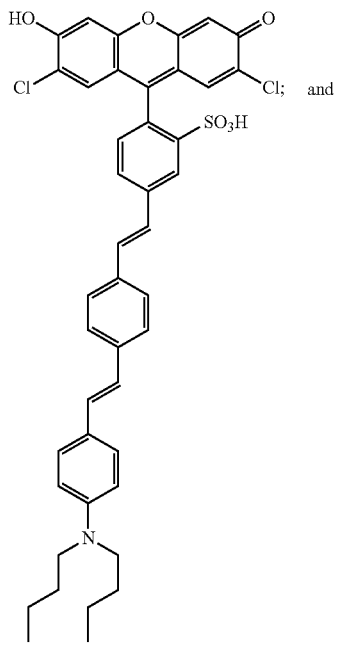
and
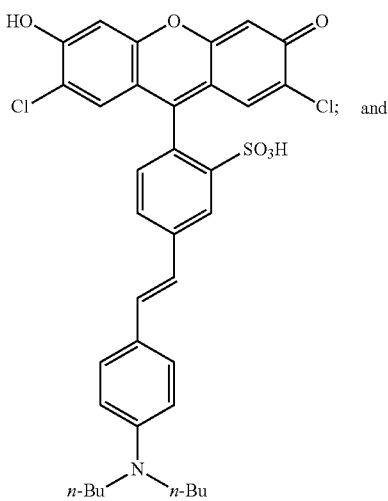
and -continued

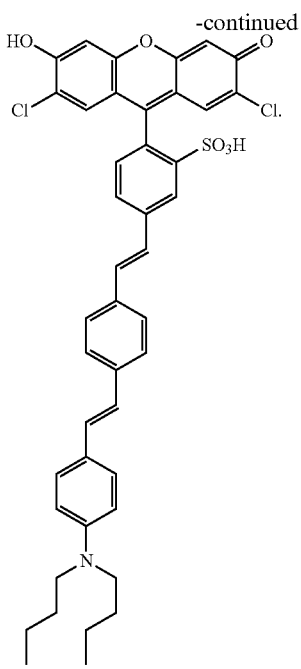

In some embodiments, the compound is substituted with a targeting moiety. In some embodiments, the targeting moiety is selected from a nucleic acid, a peptide, a saccharide, a lipid and a combination thereof. In some embodiments, the targeting moiety is specific for an excitable cell type. In some embodiments, the excitable cell type is selected from a neuron, a nerve cell, a lymphocyte, an endocrine secretory cell, a neuroendocrine secretory cell, a cardiac muscle cell, a smooth muscle cell, a skeletal muscle cell, and a mast cell.

In another aspect, the invention provides an amphipathic compound having the structure:

E-M-A wherein A is a charged fluorophore selected from the group consisting of xanthenes, coumarins, cyanines, and bimanes. M is a molecular wire. E is an electron-rich, hydrophobic moiety capable of a photo-induced electron transfer to A through the molecular wire, which quenches the fluorescence of A in response to a voltage condition.

In some embodiments, the compound is not:

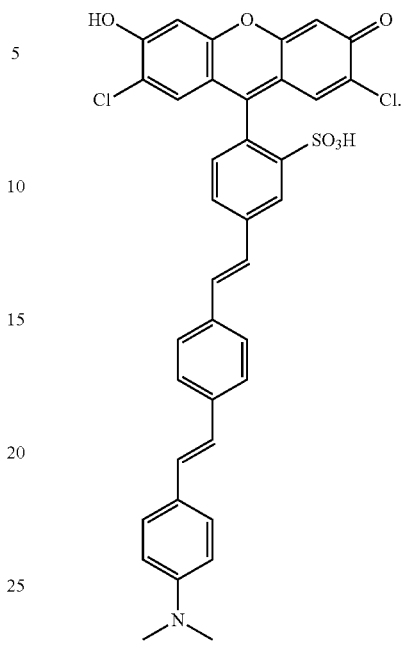

In some embodiments, A is a positively charged fluorophore.

In some embodiments, A is a negatively charged fluorophore.

In some embodiments, A is selected from xanthenes.

In some embodiments, A has a structure according to the formula:

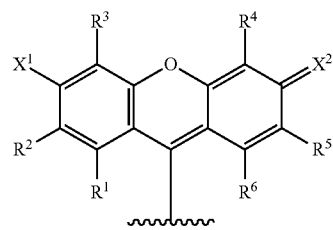

wherein $R^1$, $R^2$, $R^3$, $R^4$, $R^5$, and $R^6$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $X^1$ is selected from $Z^2R^{12}$ and $NR^{11}R^{12}$. $X^2$ is selected from $NR^{13}R^{14}$ and O. $R^{12}$ is selected from H, alkyl, substituted alkyl, heteroalkyl, substituted heteroalkyl, and $C(Z^3)R^{15}$. $R^{13}$ and $R^{15}$ are independently selected from alkyl, substituted alkyl, heteroalkyl, substituted heteroalkyl, $OR^{16}$ and $NR^{17}R^{18}$. $R^{16}$ is selected from H, alkyl, substituted alkyl, heteroalkyl, substituted heteroalkyl, aryl, substituted aryl, heteroaryl, substituted heteroaryl and $C(O)R^{19}$. $R^{19}$ is selected from alkyl, substituted alkyl, heteroalkyl and substituted heteroalkyl. $R^{11}$, $R^{13}$, $R^{14}$, $R^{17}$ and $R^{18}$ are independently selected from H, alkyl, substituted alkyl, heteroalkyl and substituted heteroalkyl. $Z^1$ and $Z^3$ are independently selected from O, S and NH. $Z^2$ is selected from O and S.

In some embodiments, A has a structure according to the formula:

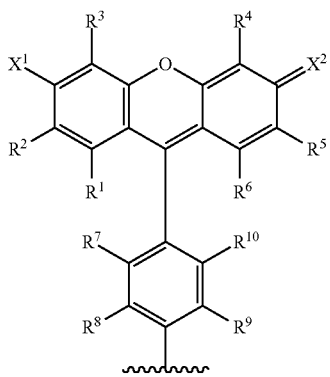

wherein $R^7$, $R^8$, $R^9$, and $R^{10}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$. $R^{11}$, $R^{12}$, $R^{13}$, $Z^1$, and $Z^2$ are as defined herein.

In some embodiments, $X^1$ is OH, $X^2$ is O, $R^2$ is Cl, $R^5$ is Cl and $R^{10}$ is $SO_3H$.

In some embodiments, $R^1$, $R^3$, $R^4$, and $R^6$ are H.

In some embodiments, $R^7$, $R^8$ and $R^9$ are H.

In some embodiments, E is selected from a substituted aryl and substituted heteroaryl.

In some embodiments, E is phenyl substituted with an amine.

In some embodiments, E has the structure according to the formula:

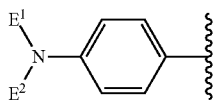

wherein $E^1$ and $E^2$ are independently alkyl. In some embodiments, $E^1$ and $E^2$ are independently selected from unsubstituted $C_1$-$C_6$ alkyl. In some embodiments, $E^1$ and $E^2$ are independently selected from methyl and butyl. In some embodiments, $E_1$ and $E_2$ are butyl. In some embodiments, butyl is n-butyl.

In some embodiments, M is selected from alkylene, substituted alkylene, heteroalkylene, substituted heteroalkylene, arylene, substituted arylene, heteroarylene and substituted heteroarylene.

In some embodiments, M has a structure according to the formula:

$(-M^1-M^2-)_m-(M^1)_n$ wherein $M^1$ is alkylene; $M^2$ is arylene; m is an integer selected from 0, 1, 2, 3, 4, 5, 6, 7, 8, 9, 10, 11, 12, 13, 14, 15, 16, 17, 18, 19 and 20; n is an integer selected from 0 and 1; and at least one of m and n is greater than 0.

In some embodiments, M has a structure according to the formula:

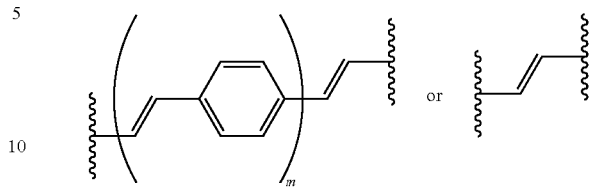

wherein m is an integer selected from 0, 1, 2, 3, 4, 5, 6, 7, 8, 9, 10, 11, 12, 13, 14, 15, 16, 17, 18, 19 and 20.

In some embodiments, M is a conjugated system.

In some embodiments, M is hydrophobic.

In some embodiments, the amphipathic compound has a structure selected from:

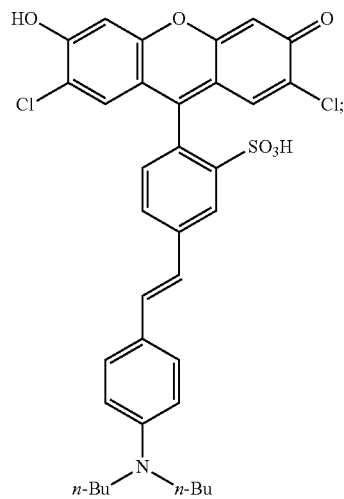

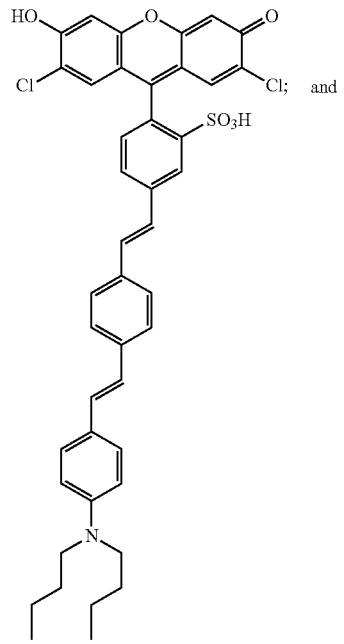

-continued

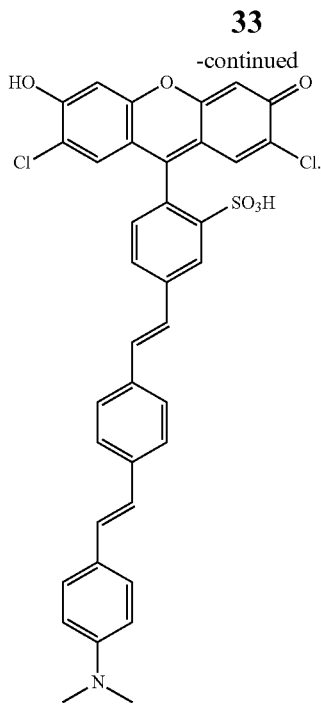

In some embodiments, the amphipathic compound has a structure selected from:

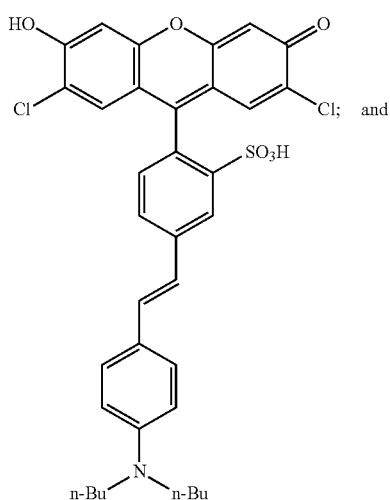

and

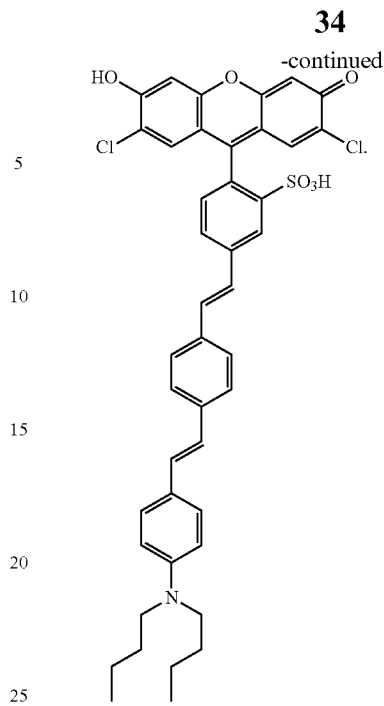

In some embodiments, the amphipathic compound is substituted with a targeting moiety.

In some embodiments, the targeting moiety is selected from a nucleic acid, a peptide, a saccharide, a lipid and a combination thereof. In some embodiments, the targeting moiety is specific for an excitable cell type. In some embodiments, the excitable cell type is selected from a neuron, a nerve cell, an endocrine secretory cell, a neuroendocrine secretory cell, a cardiac muscle cell, a smooth muscle cell, a skeletal muscle cell.

In another aspect, the invention provides a composition comprising a living cell, wherein the cell has a membrane comprising a compound disclosed herein.

In some embodiments, the living cell is a mammalian cell. In some embodiments, the living cell is an excitable cell type. In some embodiments, the excitable cell type is selected from a neuron, a nerve cell, an endocrine secretory cell, a neuroendocrine secretory cell, a cardiac muscle cell, a smooth muscle cell, a skeletal muscle cell. In some embodiments, the cell is selected from a HEK293 cell and a neuron.

In some embodiments, the membrane is the plasma membrane of the cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

In another aspect, the invention provides a method for monitoring transmembrane potential of a living cell, comprising:
a. introducing a plurality of a compound disclosed herein into a sample comprising a living cell under conditions that permit the interaction of said plurality of compound with a plasma membrane of said cell;

b. exciting the compound with light of a wavelength sufficient to excite the fluorophore portion of the compound described herein;
c. detecting fluorescence emission from the plurality of the compound; and
d. correlating said fluorescence emission to the transmembrane potential of the living cell,
e. wherein the quenching of fluorescence emitted by the plurality of the compound is altered in response to a change in the membrane potential.

In some embodiments, the living cell is a mammalian cell.

In some embodiments, the living cell is an excitable cell type.

In some embodiments, the excitable cell type is selected from a neuron, a nerve cell, an endocrine secretory cell, a neuroendocrine secretory cell, a cardiac muscle cell, a smooth muscle cell, a skeletal muscle cell.

In some embodiments, the cell is selected from a HEK293 cell and a neuron.

In some embodiments, the membrane is the plasma membrane of said cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

In another aspect, the invention provides a method of identifying a test chemical that modulates transmembrane potential in at least one cell, said method comprising the steps:
a. contacting said at least one cell with a plurality of a compound disclosed herein, wherein said cell has a membrane;
b. exposing the membrane to said test chemical;
c. exciting the compound with light of a wavelength sufficient to excite the fluorophore portion of the compound disclosed herein;
d. detecting fluorescence emission of said plurality of the compound;
e. correlating said fluorescence emission to transmembrane potential of the cell; and
f. comparing said transmembrane potential to a control value, wherein a difference between said transmembrane potential and the control value is indicative of the test chemical's ability to modulate transmembrane potential of said cell.

In some embodiments, the cell is a living cell.

In some embodiments, the living cell is a mammalian cell.

In some embodiments, the living cell is an excitable cell type.

In some embodiments, the excitable cell type is selected from a neuron, a nerve cell, an endocrine secretory cell, a neuroendocrine secretory cell, a cardiac muscle cell, a smooth muscle cell, a skeletal muscle cell.

In some embodiments, the cell is selected from a HEK293 cell and a neuron.

In some embodiments, the membrane is the plasma membrane of said cell.

In some embodiments, the cell is voltage clamped.

In some embodiments, the membrane comprises at least one ion channel, ion transporter, ion pump, or ion exchanger.

In some embodiments, the membrane of the living cell comprises an inner layer and an outer layer, wherein the A moiety of the compound disclosed herein localizes at the outer layer of said membrane, and the E moiety of the compound disclosed herein localizes at a region between the inner layer and outer layer.

II. DRUG SCREENING

The invention also provides methods for screening candidate agents such as potential therapeutic drugs which affect membrane potentials in biological cells. These methods involve measuring membrane potentials as described above in the presence and absence (control measurement) of the test sample. Control measurements are usually performed with a sample containing all components of the test sample except for the putative drug. Detection of a change in membrane potential in the presence of the test agent relative to the control indicates that the test agent is active. Membrane potentials can be also be determined in the presence or absence of a pharmacologic agent of known activity (i.e., a standard agent) or putative activity (i.e., a candidate agent). A difference in membrane potentials as detected by the methods disclosed herein allows one to compare the activity of the test agent to that of the standard agent. It will be recognized that many combinations and permutations of drug screening protocols are known to one of skill in the art and they may be readily adapted to use with the method of membrane potential measurement disclosed herein to identify compounds which affect membrane potentials. Use of the membrane potential determination technique disclosed herein in combination with all such methods are contemplated by this invention. In a particular embodiment, the invention offers a method of identifying a compound which modulates activity of an ion channel, pump, or exchanger in a membrane, comprising:
a. loading the cells with a plurality of the compound described herein
b. exposing the cell membrane to the candidate agent;
c. exciting the plurality of compound with light of a wavelength sufficient to excite the fluorophore;
d. detecting fluorescence emission of said plurality of the compound;
e. correlating said fluorescence emission to transmembrane potential of the cell; and
f. comparing said transmembrane potential to a control value, wherein a difference between said transmembrane potential and the control value is indicative of the agent's ability to modulate transmembrane potential of said cell.

In another embodiment, the invention offers a method of screening test samples to identify a compound which modulates the activity of an ion channel, pump or exchanger in a membrane, comprising:
a. loading a first set and a second set of cells with a plurality of the compound described herein;
b. optionally, exposing both the first and second set of cells to a stimulus which modulates the ion channel, pump or exchanger;
c. exposing the first set of cells to the candidate agent;
d. exciting the plurality of compound in both the first and second set of cells with light of a wavelength sufficient to excite the fluorophore;
e. detecting fluorescence emission of said plurality of the compound in both the first and second set of cells;
f. correlating said fluorescence emission to transmembrane potential of the cell for both the first and second set of cells; and g. relating the difference in membrane potentials between the first and second sets of cells to the ability of the candidate agent to modulate the activity of an ion channel, pump or exchanger in a membrane.

Ion channels of interest include, but are not limited to, sodium, calcium, potassium, nonspecific cation, and chloride ion channels, each of which may be constitutively open, voltage-gated, ligand-gated, or controlled by intracellular signaling pathways.

Biological cells which can be screened include, but are not limited to primary cultures of mammalian cells, cells dissociated from mammalian tissue, either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like. The invention also includes the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel) and methods for their expression in cell lines of interest is within the knowledge of one of skill in the art (see, U.S. Pat. No. 5,436,128). Representative cultured cell lines derived from humans and other mammals include LM (TK.sup.-) cells, HEK293 (human embryonic kidney cells), 3T3 fibroblasts, COS cells, CHO cells, RAT1 and HLHepG2 cells.

The screening methods described herein can be made on cells growing in or deposited on solid surfaces. A common technique is to use a microtiter plate well wherein the fluorescence measurements are made by commercially available fluorescent plate readers. The invention includes high throughput screening in both automated and semiautomated systems. One such method is to use cells in Costar 96 well microtiter plates (flat with a clear bottom) and measure fluorescent signal with CytoFluor multiwell plate reader (Perseptive Biosystems, Inc., MA) using two emission wavelengths to record fluorescent emission ratios.

Suitable equipment, software, and methods for conducting the screening, including detection of fluorescence emission and correlation of fluorescence emissions to transmembrane potential of the cell, are described in the examples or as contemplated by those of skill in the art based on guidance from the disclosure provided herein.

EXAMPLES

Examples are provided below to illustrate the present invention. These examples are not meant to constrain the present invention to any particular application or theory of operation.

Example 1

Design and Synthesis of VF Sensors

Our initial voltage sensors incorporate dichlorosulfofluorescein as a membrane-impermeant fluorophore, a p-phenylenevinylene (PPV) molecular wire, and N,N-dimethyl- or dibutylaniline as an electron-rich quencher (Scheme 1). VF1.4.Cl comprises 2,7-dichlorosulfofluorescein connected via one vinylene unit to dibutylaniline (hence VF1.4.Cl). VF2.4.Cl adds a second PPV unit, and VF2.1.Cl features the same configuration, with methyl substituted in place of butyl groups.

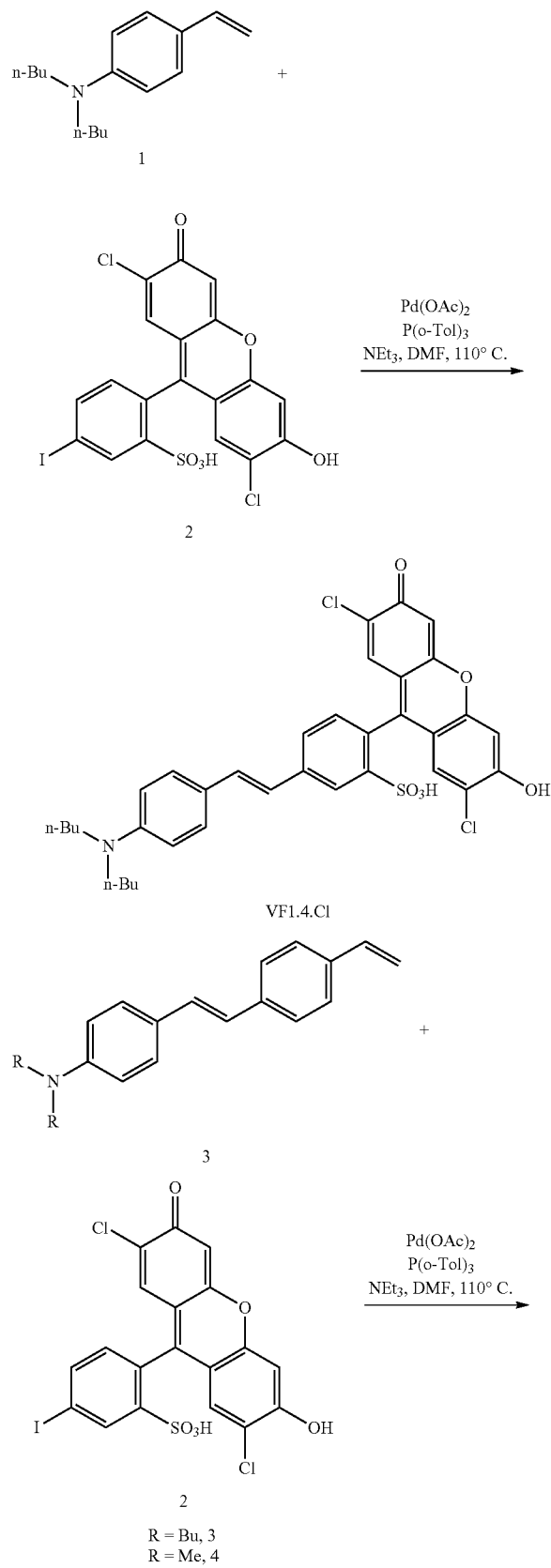

Scheme 1. Synthesis of VF probes.

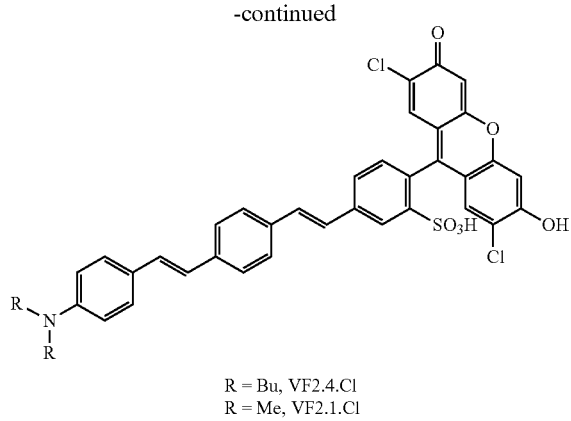

R = Bu, VF2.4.Cl
R = Me, VF2.1.Cl

Correct positioning of the fluorophore-wire donor within the membrane is vital to take advantage of the vectoral nature of the transmembrane electric field and electron transfer. First, the longitudinal axis of the molecular wire must be normal to the plane of the plasma membrane, to sample the full electric field. Second, dye molecules must all align in the same direction to avoid canceling out the electron transfer effect. Positioning the fluorophore at the extracellular leaflet of the membrane ensures fluorescence brightening upon depolarization; the opposite orientation of PeT would give fluorescence quenching upon depolarization.

The negatively charged sulfofluorescein will preclude dye internalization and force an orientation in which the fluorophore adsorbs to the outer leaflet of the plasma membrane, with the lipophilic molecular wire and alkyl aniline dangling into the lipid bilayer. As an intervening spacer, PPV molecular wires are an ideal choice because of their low attenuation values (26), synthetic tractability, and demonstrated ability to conduct current through lipid bilayers (31). Anilines are common PeT donors and the di-alkyl groups should enhance uptake into the plasma membrane.

A modular synthetic design both allows for rapid generation of the voltage sensors and enables future derivatization (Scheme 1 and chemical synthesis detailed herein). Coupling of the molecular wire styrene unit 1, available in one step from 4-di-butylaminobenzaldehyde, with iodo-functionalized dichlorosulfofluorescein 2 via a Pd-catalyzed Heck reaction gives VF1.4.Cl in good yield. An analogous reaction with molecular wire 3, available in two steps from 1, gives VF2.4.Cl in 70% yield. A parallel reaction beginning from styrene 4 furnishes VF2.1.Cl in good yield.

Figure 8:
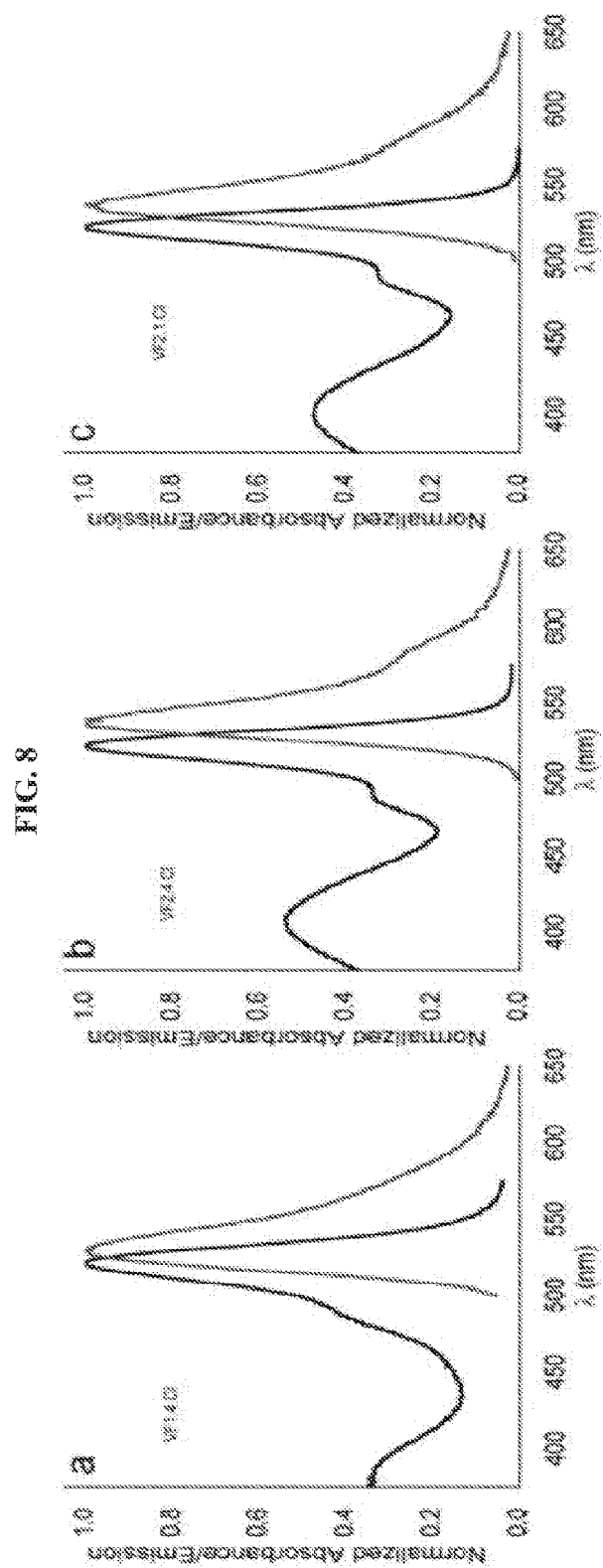
FIG. 8 shows the normalized absorbance and emission spectra for exemplary compounds of the invention in 5 mM sodium phosphate, pH 9 with 0.1% Triton X-100. Black lines are absorbance spectra; grey lines are emission spectra. a) VF1.4.Cl, b) VF2.4.Cl, and c) VF2.1.Cl.

All dyes feature emission and excitation profiles typical of dichlorofluoresceins (VF1.4.Cl: $\lambda_{max}$=521 nm, $\in$=93,000 $M^{-1} \cdot cm^{-1}$, $\lambda_{em}$=534 nm, $\Phi$=0.24; VF2.4.Cl: $\lambda_{max}$=522 nm, $\in$=97,000 $M^{-1} \cdot cm^{-1}$, $\lambda_{em}$=536 nm, $\Phi$=0.054; VF2.1.Cl: $\lambda_{max}$=522 nm, $\in$=98 000 $M^{-1} \cdot cm^{-1}$, $\lambda_{em}$=535 nm, $\Phi$=0.057, 5 mM sodium phosphate, pH 9, 0.1% Triton X-100) (FIG. 8).

Figure 3:
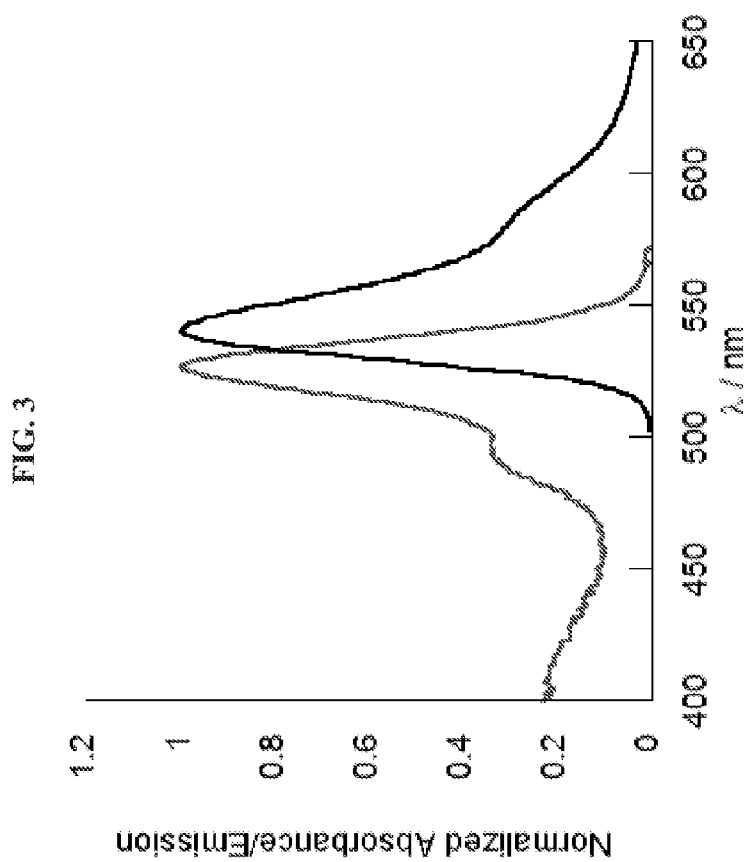
FIG. 3 shows the normalized absorbance and emission spectra of VF2.4.Cl in n-octanol.

VF2.4.Cl features an absorbance spectrum with a $\lambda_{max}$ in octanol (to simulate cellular membranes) centered at 527 nm ($\in_{527}$=4×10$^4$ $M^{-1}cm^{-1}$). Excitation of VF2.4.Cl at 527 nm results in emission centered at 540 nm ($\Phi$=0.23) (FIG. 3).

General Synthetic and Analytical Methods

Pd(OAc)$_2$ was from Strem Chemicals. All other chemicals were purchased from Sigma-Aldrich and used as received unless otherwise noted. 2',7'-dichloro-5-iodosulfofluorescein (2) was synthesized according to literature procedure. [Jiao, G. S., Han, J. W. & Burgess, K. Syntheses of regioisomerically pure 5- or 6-halogenated fluoresceins. *J. Org. Chem.* 68, 8264-8267 (2003).] Anhydrous solvents and reagents (THF, DMF, NEt$_3$) were obtained as SureSeal bottles from Sigma-Aldrich. Thin-layer chromatography and flash chromatography were performed using EMD pre-coated silica gel 60 F-254 plates and silica gel 60 (230-400 mesh). Alumina was activity 1, 70-230 mesh.

UV absorbance and fluorescence spectra were recorded on a Cary 3E (Varian) and Fluorolog 2 (Spex) fluorimeter, respectively. Analytical, semi-preparative, and preparative HPLCs were performed on Agilent HPLCs, with Luna C18(2) columns (Phenomenex) using water (solvent A) and acetonitrile (solvent B) with 0.05% TFA as an additive. Low resolution ESI mass spectrometry was performed on an Agilent LC/MSD Trap XCT coupled to an Agilent HPLC. High resolution mass spectra were acquired on a Thermo-Fisher Orbitrap XL hybrid mass spectrometer. $^1$H NMR spectra were collected in CDCl$_3$ or d$_6$-DMSO (Cambridge Isotope Laboratories, Cambridge, Mass.) at 25° C. on a 400 Varian Mercury Plus or Jeol ECA 500 spectrometer at the Department of Chemistry and Biochemistry NMR Facility at the University of California, San Diego. All chemical shifts are reported in the standard δ notation of parts per million using the peak of residual proton signals of CDCl$_3$ or d$_6$-DMSO as an internal reference.

Chemical Synthesis

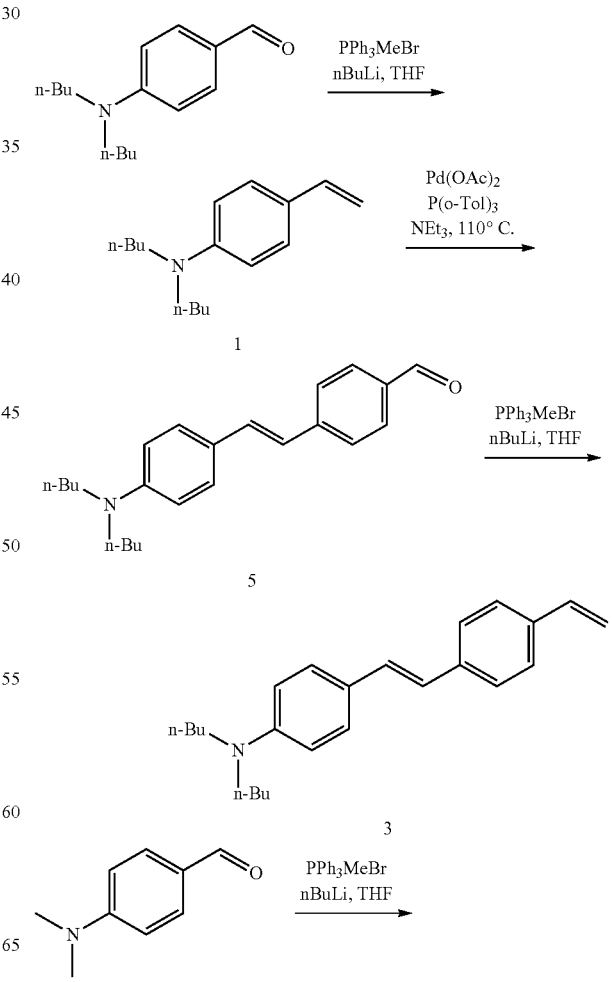

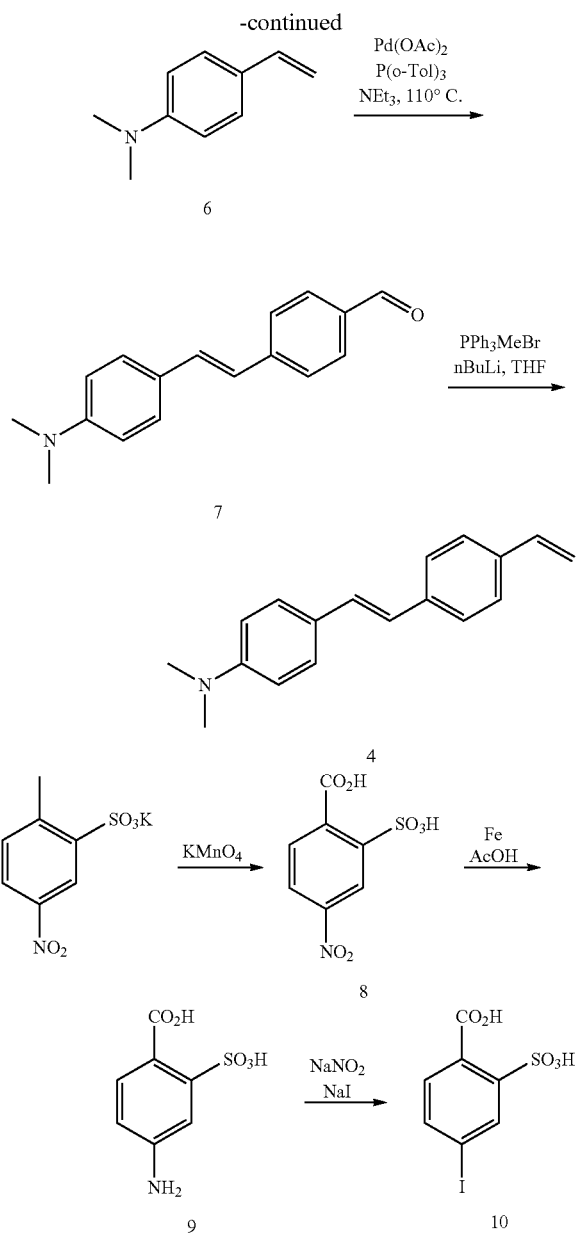

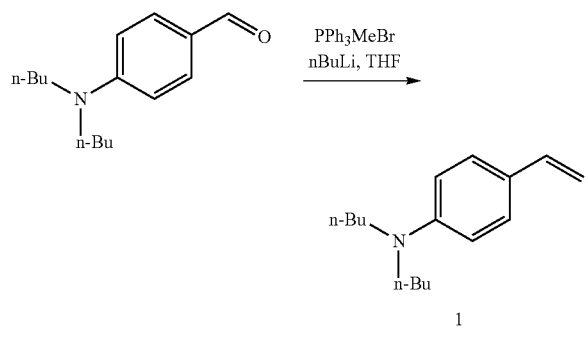

Synthesis of N,N-dibutyl-4-aminostyrene (1)

An oven-dried roundbottom flask was charged with methyltriphenylphosphonium bromide (1.4 g, 3.9 mmol, 1.8 equiv.) and 10 mL anhydrous THF and stirred under $N_2$. A 1.6 M solution of n-butyllithium in hexanes was added via syringe (2.2 mL, 3.5 mmol, 1.6 equiv.) at room temperature. After stirring for 15 min, 4-N,N-dimethylbenzaldehyde (508 mg, 2.2 mmol, 1.0 equiv.) was added. After stirring overnight, the reaction was poured into 100 mL of hexanes. The suspension was filtered through Celite and concentrated under reduced pressure. The residue was taken up in EtOAc and filtered through a thin pad (1-2 cm) of silica. Removal of solvents under reduced pressure provided 505 mg of a yellow oil (99%) which was judged to be pure by $^1$H NMR. δ(CDCl$_3$): 7.28 (2H, d, J=8.6 Hz); 6.60 (3H, m); 5.50 (1H, d, J=17.8 Hz); 4.98 (1H, d, J=10.3 Hz); 3.27 (4H, m); 1.57 (4H, q, J=7.4 Hz); 1.35 (4H, sextet, J=7.4 Hz); 0.96 (6H, t, J=7.4 Hz).

Synthesis of (E)-4-(4-(dibutylamino)styryl)benzaldehyde (5)

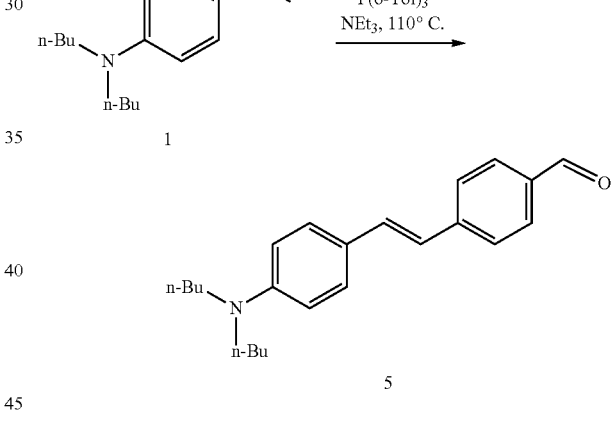

An oven-dried screw cap vial was equipped with a stir bar and charged with 4-bromobenzaldehyde (832 mg, 4.5 mmol, 1.0 equiv.), Pd(OAc)$_2$ (10 mg, 0.045 mmol, 0.01 equiv.), tri-o-tolylphosphine (27 mg, 0.09 mmol, 0.02 equiv.), and (1) (1.3 g, 5.6 mmol, 1.25 equiv.). The flask was evacuated and backfilled three times with $N_2$. Triethylamine (2.25 mL) was added, the vial sealed, and heated at 110° C. After stirring 20 hours, the reaction vessel was cooled to room temperature, dissolved in EtOAc and washed with saturated NaCl. The organic portions were dried over Na$_2$SO$_4$, filtered, and concentrated under reduced pressure. The orange residue was recrystallized from hexanes to give 5 as orange-yellow needles, 1.2 g (64%). $^1$H NMR. δ(CDCl$_3$): 9.94 (1H, s); 7.82 (2H, d, J=8.0 Hz); 7.58 (2H, d, J=8.6 Hz); 7.40 (2H, d, J=9.2 Hz); 7.19 (1H, d, J=16.6 Hz); 6.89 (1H, d, J=16.0 Hz); 6.62 (2H, d, J=8.6 Hz); 3.30 (4H, m); 1.58 (4H, m); 1.36 (4H, sextet, J=7.4 Hz); 0.96 (6H, t, J=7.4 Hz).

Synthesis of (E)-N,N-dibutyl-4-(4-vinylstyryl)aniline (3)

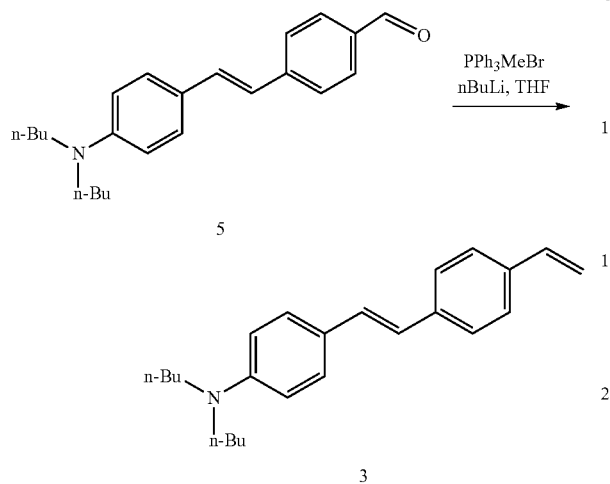

An oven-dried two-neck round bottom flask was cooled under N$_2$ and charged with methyltriphenylphosphonium bromide (2.1 g, 5.9 mmol, 1.8 equiv.) and anhydrous THF (15 mL). A 1.6 M solution of n-butyllithium in hexanes was added via syringe (3.3 mL, 5.3 mmol, 1.6 equiv.) and stirred for 15 minutes at ambient temperature. A solution of 5 (1.1 g, 3.3 mmol, 1.0 equiv.) in THF (5 mL) was added with stirring. After stirring 12 hours, the reaction mixture was dissolved in CH$_2$Cl$_2$, filtered through a thin plug of alumina (1-2 cm), eluting with CH$_2$Cl$_2$. The organics were removed under reduced pressure to give a yellow solid which was triturated with EtOH. The resulting pale yellow solid was filtered and washed with EtOH to give (3), 958 mg (87%). $^1$H NMR. δ (CDCl$_3$): 8.53 (2H, d, J=8.5 Hz); 7.36 (4H, d, J=7.0 Hz); 7.03 (1H, d, J=16.6 Hz); 6.85 (1H, d, J=16.6 Hz); 6.70 (1H, dd, J1=17.0 Hz, J2=10.8 Hz); 6.62 (2H, d, J=8.5 Hz); 5.73 (1H, d, J=17.6 Hz); 5.20 (1H, d, J=11.5 Hz); 3.28 (4H, t, J=7.5 Hz); 1.58 (4H, m); 1.36 (4H, sextet, J=7.5 Hz); 0.96 (6H, t, J=7.5 Hz).

Synthesis of N,N-dimethyl-4-vinylaniline (6)

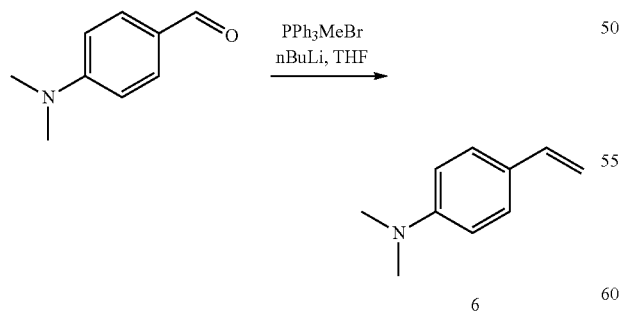

An oven-dried roundbottom flask was charged with methyltriphenylphosphonium bromide (4.3 g, 3.9 mmol, 1.8 equiv.) and 30 mL anhydrous THF and stirred under N$_2$. A 1.6 M solution of n-butyllithium in hexanes was added via syringe (6.7 mL, 10.7 mmol, 1.6 equiv.) at room temperature. After stirring for 15 min, 4-N,N-dimethylbenzaldehyde (1.0 g, 6.7 mmol, 1.0 equiv.) was added. After stirring overnight, the reaction was poured into 100 mL of hexanes. The suspension was filtered through Celite and concentrated under reduced pressure. The residue was taken up in EtOAc and filtered through a thin pad (1-2 cm) of alumina. Removal of solvents under reduced pressure provided 870 mg of 6 as a yellow oil (88%) which was judged to be pure by $^1$H NMR. δ(CDCl$_3$): 7.30 (2H, d, J=8.5 Hz); 6.68 (2H, d, J=9.0 Hz); 6.63 (1H, dd, J$_1$=17.6 Hz, J$_2$=11.0 Hz); 5.53 (1H, d, J=17.6 Hz); 5.01 (1H, d, J=10.5 Hz); 2.95 (6H, s).

Synthesis of (E)-4-(4-(dimethylamino)styryl)benzaldehyde (7)

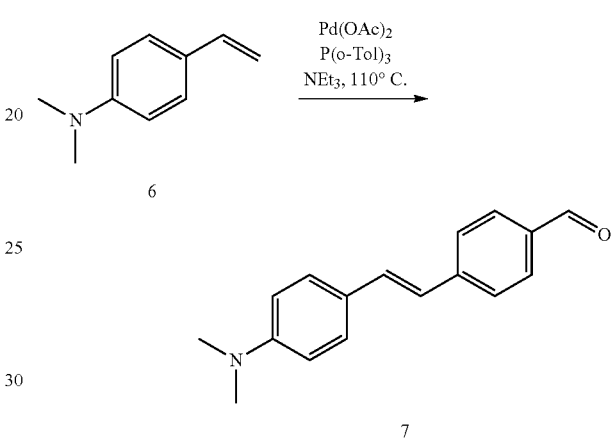

An oven-dried screw cap vial was equipped with a stir bar and charged with 4-bromobenzaldehyde (775 mg, 4.2 mmol, 1.0 equiv.), Pd(OAc)$_2$ (9.4 mg, 0.042 mmol, 0.01 equiv.), tri-o-tolylphosphine (25.5 mg, 0.084 mmol, 0.02 equiv.), and N,N-dimethyl-4-vinylaniline (770 mg, 5.2 mmol, 1.25 equiv.). The flask was evacuated and backfilled three times with N$_2$. Triethylamine (2.5 mL) was added, the vial sealed, and heated at 110° C. After stirring 20 hours, the reaction vessel was cooled to room temperature, dissolved in CH$_2$Cl$_2$ and washed with saturated NH$_4$Cl, followed by saturated NaCl. The organic portions were dried over Na$_2$SO$_4$, filtered, and concentrated under reduced pressure. The orange residue was taken up in a minimal amount of CH$_2$Cl$_2$ and crystallization was induced by addition of excess hexanes. Trituration with hexanes provided 970 mg of 7 (92%). $^1$H NMR. δ(CDCl$_3$): 9.95 (1H, s); 7.82 (2H, d, J=8.0 Hz); 7.59 (2H, d, J=8.6 Hz); 7.44 (2H, d, J=9.2 Hz); 7.20 (1H, d, J=16.0 Hz); 6.93 (1H, d, J=16.0 Hz); 6.71 (2H, d, 0.1=8.6 Hz); 3.0 (6H, s).

Synthesis of (E)-N,N-dimethyl-4-(4-vinylstyryl)aniline (4)

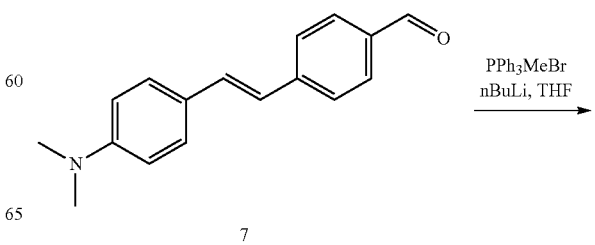

-continued

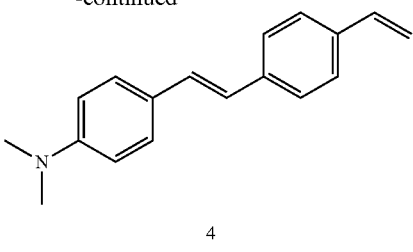

4

An oven-dried two-neck round bottom flask was cooled under $N_2$ and charged with methyltriphenylphosphonium bromide (950 mg, 6.8 mmol, 1.8 equiv.) and anhydrous THF (15 mL). A 1.6 M solution of n-butyllithium in hexanes was added via syringe (3.8 mL, 6.1 mmol, 1.6 equiv.) and stirred for 15 minutes at ambient temperature. A solution of 7 (950 mg, 3.8 mmol, 1.0 equiv.) in THF (5 mL) was added with stirring. After stirring 12 hours, the reaction mixture was dissolved in $CH_2Cl_2$, filtered through a thin plug of alumina (1-2 cm), eluting with $CH_2Cl_2$. The organics were removed under reduced pressure to give a yellow solid which was triturated with EtOH. The resulting pale yellow solid was filtered and washed with EtOH to give (4), 621 mg (66%). $^1$H NMR. δ ($CDCl_3$): 7.40 (6H, m); 7.04 (1H, d, J=16.6 Hz); 6.89 (1H, d, J=16.6 Hz); 6.70 (3H, m); 5.73 (1H, d, J=17.6 Hz); 5.21 (1H, d, J=11.0 Hz); 2.98 (6H, s).

Synthesis of 4-nitro-2-sulfobenzoic acid (8)

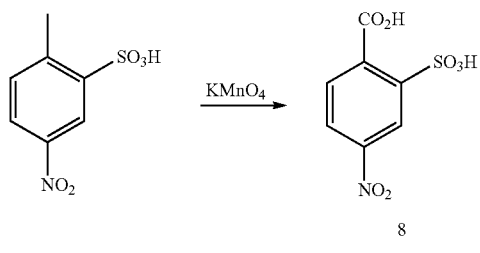

To a slurry of $KMnO_4$ (15 g, 96 mmol, 4 equiv.) in 120 mL water was added 30 mL of a solution of 4-nitrotoluene-2-sulfonic acid dihydrate (6.0 g, 24 mmol, 1.0 equiv.). The reaction vessel was fitted with a reflux condenser and the reaction heated at reflux for 4 hours. The reaction was cooled on ice and filtered to give a tan solution. The solid precipitate was washed with 200 mL of water, and the filtrate was then concentrated under reduced pressure to give about 100 mL. This was cooled on ice and acidified with concentrated HCl until the pH was less than 1. The mixture was heated to dissolve the white precipitate which formed, and cooled slowly to form white crystals. After storing overnight at 4° C., the off-white crystals were filtered, washed with 1-2 mL of cold water, and dried on a Büchner funnel to give 4.0 g (67%) of 8 as an off-white/peach solid that was judged to be 90% pure by $^1$H NMR. $^1$H NMR: δ ($d_6$-DMSO): 8.48 (1H, d, J=2.5 Hz); 8.24 (1H, dd, $J_1$=8.3 Hz, $J_2$=2.5 Hz); 7.70 (1H, d, J=8.0 Hz). ESI-MS, $[M-H]^-$=246.

Synthesis of 4-amino-2-sulfobenzoic acid, (9)

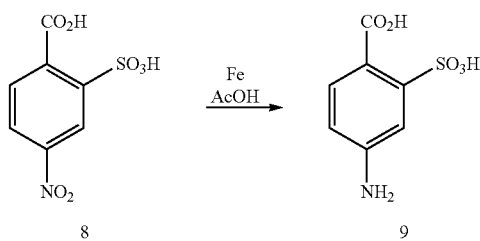 [SMILES: O=C(O)c1ccc([N+](=O)[O-])cc1S(=O)(=O)O ; Nc1ccc(C(=O)O)c(S(=O)(=O)O)c1 ; "FeAcOH"]

4-nitro-2-sulfobenzoic acid (4.0 g, 16.2 mmol, 1.0 equiv.) was dissolved in 12.5 mL of water and stirred in a 300 mL round bottom flask fitted with a reflux condenser. The reaction was heated to boiling, at which point all of 8 dissolved. 2.5 mL glacial acetic acid was added, followed by 6.35 g of Fe (113 mmol, 7.0 equiv.) in ~0.5 g portions every 15 minutes to avoid excessive bubbling. Upon completion of addition, the reaction was maintained at reflux for an additional 60 minutes. The reaction was cooled to room temperature, transferred to an Erlenmeyer flask, heated to boiling, and filtered while hot to remove unreacted iron. The solid was washed with several portions of boiling water (about 100 mL total). The pale green filtrate was again heated to boiling and filtered through a thin pad of Celite to get a pale orange solution. This was concentrated under reduced pressure, cooled on ice, and acidified with concentrated HCl until the pH was less than 1 and a yellow color/precipitate persisted. This was recrystallized from boiling water (about 100 mL total) and stored overnight at 4° C. The yellow solid was filtered to get 1.32 g of 9. The mother liquor was placed back in the cold room for two more days. A second crop of crystals was isolated, 230 mg. The crops were pooled to give 1.55 g of 9, which was pure by $^1$H NMR. $^1$H NMR: δ ($d_6$-DMSO): 7.65 (1H, d, J=8.5 Hz); 7.16 (1H, d, J=2.0 Hz); 6.62 (1H, d, J=8.0 Hz). ESI-MS, =216.

Synthesis of 4-iodo-2-sulfobenzoic acid (10)

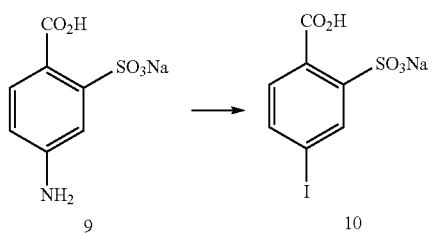

The hydrochloride salt of 4-amino-2-sulfobenzoic acid (9) was suspended in 10 mL $H_2O$. $Na_2CO_3$ was added (500 mg) and the reaction stirred until the solution was homogenous and the pH was about 8. After cooling on ice, $NaNO_2$ (355 mg, 5.2 mmol, 1.12 equiv.) dissolved in 1 mL $H_2O$ was added. This solution was cooled on ice. With stirring, HCl (1 mL concentrated HCl diluted in 5 g crushed ice) was added and stirring continued on ice for 30 minutes. A solution of NaI (828 mg, 5.5 mmol, 1.2 equiv.) in 1 mL $H_2O$ (cooled on ice) was added dropwise. The reaction went dark and produced gas. Stirring was maintained for 2 hours on ice, then 1 hour at room temperature and finally at 50° C. overnight. The following morning, 3 drops of conc. HCl were added and the reaction was concentrated on the rotovap to give a red/orange solid. This was recrystallized from boiling H$_2$O (<20 mL). Filtered the fluffy orange crystals to get 925 mg of 10. The mother liquor was concentrated to dryness and recrystallized again to get an additional 315 mg (76% yield, total). $^1$H NMR: δ (d$_6$-DMSO): 8.10 (1H, d, J=1.5 Hz); 7.86 (1H, dd, J=8.0 Hz, J$_2$=1.5 Hz); 7.42 (1H, d, J=8.0 Hz). ESI-MS, [M+H]$^+$=329, [M−H]$^−$=327.

Synthesis of 5-(4-(4-(dibutylamino)styryl)styryl)-2-(2,7-dichloro-6-hydroxy-3-oxo-3H-xanthen-9-yl)benzenesulfonic acid, Voltage Fluor 2.4.Cl (VF2.4.Cl)

dried to give 14.4 mg of a brick red solid. This crude product was taken up in 200 μL of DMSO. 200 μL of MeCN was added to induce precipitation, and the resulting orange/brown solid was filtered on a Büchner funnel to give 9.6 mg (70%) of VF2.4.Cl. Samples for analytical measurements were further purified by preparative HPLC. $^1$H NMR (500 MHz, d$_6$-DMSO) δ: 8.14 (1H, d, J=1.2 Hz); 7.76 (1H, dd, J$_1$=8.0 Hz, J$_2$=1.7 Hz); 7.64 (2.5H, d, J=8.0 Hz); 7.53 (2.5 Hz, d, J=8.0 Hz); 7.41 (2.5H, d, J=16.6 Hz); 7.36 (2.5H, d, J=16.6 Hz); 7.22 (1H, d, J=8.0 Hz); 7.15 (1H, m); 6.95 (3H, s); 6.72 (1H, bs); 6.61 (1H, bs); 3.26 (4H, t, J=6.9 Hz); 1.47 (4H, m); 1.29 (4H, sextet, J=7.4 Hz); 0.89 (6H, t, J=7.4 Hz). HR-ESI, calculated for C$_{43}$H$_{39}$Cl$_2$NO$_6$S, 767.1875. found [M$^+$]=767.1888.

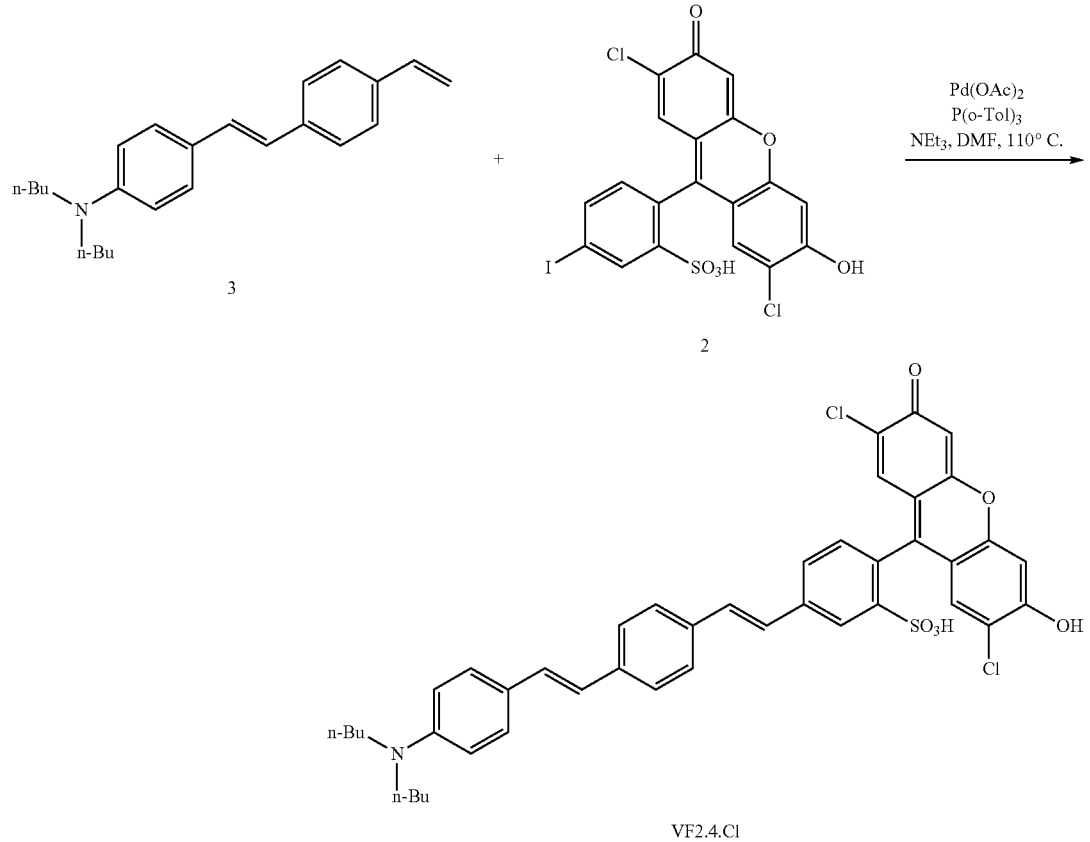

An oven-dried, N$_2$-cooled reaction tube was charged with 10 mg (17.8 μmol, 1.0 equiv.) of 2, 6.6 mg (19.6 μmol, 1.1 equiv.) of styrene 3, 1 mg (4.5 μmol, 0.25 equiv.) Pd(OAc)$_2$, 3 mg (9.0 μmol, 0.5 equiv.) of tri-o-tolylphosphine and a stirbar. The tube was fitted with a septum and evacuated and backfilled with N$_2$ three times. 100 μL of DMF and 50 μL of NEt$_3$ (0.36 mmol, 20 equiv.) were added via syringe, the septum replaced, and the reaction stirred at 110° C. overnight. After stirring 12 hours, the reaction was cooled to room temperature, concentrated under reduced pressure, and taken up in CH$_2$Cl$_2$ and dilute aqueous KOH. After extracting 3× with CH$_2$Cl$_2$, the combined organic layers were extracted twice with dilute aqueous KOH. The pooled aqueous fractions were cooled on ice, and then acidified with cold concentrated HCl. A fine red solid precipitated out and this was filtered on a Büchner funnel, washed with Et$_2$O, and Synthesis of 5-(4-(4-(dimethylamino)styryl)styryl)-2-(2,7-dichloro-6-hydroxy-3-oxo-3H-xanthen-9-yl)benzenesulfonic acid, Voltage Fluor 2.1.Cl (VF2.1.Cl)

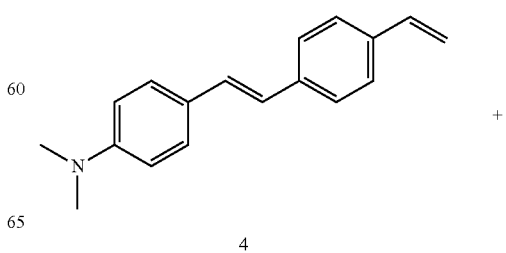

49

-continued

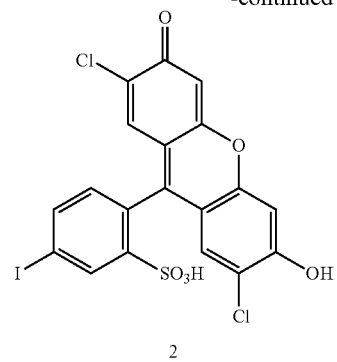

2

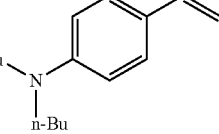

VF2.1.Cl

An oven-dried, N$_2$-cooled reaction tube was charged with 8 mg (14 µmol, 1.0 equiv.) of 4, 3.9 mg (16 µmol, 1.1 equiv.) of (E)-N,N-dimethyl-4-(4-vinylstyryl)aniline, 1 mg (4.5 µmol, 0.32 equiv.) Pd(OAc)$_2$, 3 mg (9.0 µmol, 0.7 equiv.) of tri-o-tolylphosphine and a stirbar. The tube was fitted with a septum and evacuated and backfilled with N$_2$ three times. 500 µL of DMF and 50 µL of NEt$_3$ (0.36 mmol, 25 equiv.) were added via syringe, the septum replaced, and the reaction stirred at 110° C. overnight. After stirring 12 hours, the reaction was cooled to room temperature, concentrated under reduced pressure, and concentrated down several times from CH$_2$Cl$_2$/hexanes to get a reddish brown solid. Took up in 1N NaOH to get a murky solution which was cooled on ice and acidified with concentrated HCl. The ensuing precipitate was filtered and dried on a Büchner funnel and washed with water and diethyl ether. This residue was dissolved in 400 µL 1:1 DMSO:MeCN and purified by preparative HPLC to give 5.6 mg of a tan/orange solid (51% yield).

$^1$H NMR (500 MHz, d$_6$-DMSO) δ: 8.14 (1H, d, J=1.7 Hz); 8.10 (1H, s); 7.76 (1H, dd, J$_1$=8.0 Hz, J$_2$=1.2 Hz); 7.64 (2H, d, J=8.0 Hz); 7.55 (2H, d, J=8.6 Hz); 7.45 (2H, d, J=8.6 Hz); 7.42 (1H, d, J=16.6 Hz); 7.36 (1H, d, J=16.6 Hz); 7.22 (1H, d, J=8.0 Hz); 7.18 (1H, d, J=16.6 Hz); 7.00 (1H, d, J=16.6 Hz); 6.95, (2H, s); 6.76 (1H, bs); 6.72 (2H, bs); 2.93 (6H, s). HR-ESI, calculated for C$_{37}$H$_{27}$Cl$_2$NO$_6$S, 683.0936. found [M$^+$]=683.0933.

50

Synthesis of (E)-5-(4-(dibutylamino)styryl)-2-(2,7-dichloro-6-hydroxy-3-oxo-3H-xanthen-9-yl)benzenesulfonic acid, Voltage Fluor 1.4.Cl (VF1.4.Cl)

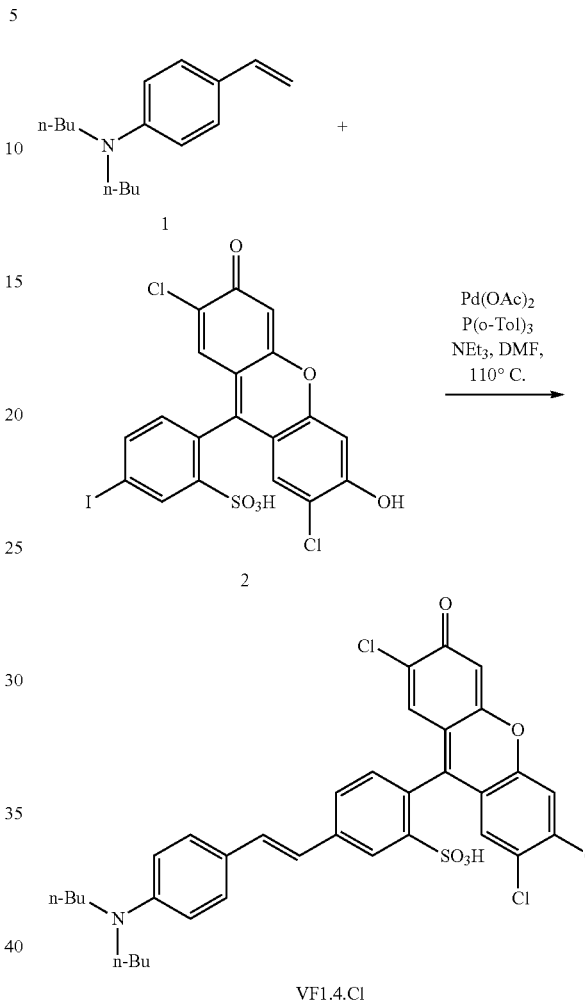

VF1.4.Cl

An oven-dried, N$_2$-cooled reaction tube was charged with 10 mg (17.8 µmol, 1.0 equiv.) of 2, 4.5 mg (19.6 µmol, 1.1 equiv.) of N,N-dibutyl-4-vinylaniline 1, 1 mg (4.5 µmol, 0.25 equiv.) Pd(OAc)$_2$, 3 mg (9.0 µmol, 0.5 equiv.) of tri-o-tolylphosphine and a stirbar. The tube was fitted with a septum and evacuated and backfilled with N$_2$ three times. 100 µL of DMF and 100 µL of NEt$_3$ (0.72 mmol, 40 equiv.) were added via syringe, the septum replaced, and the reaction stirred at 110° C. overnight. After stirring 12 hours, the reaction was cooled to room temperature, diluted a 1N solution of NaOH and washed 3× with CH$_2$Cl$_2$. The aqueous layer was concentrated to near dryness, acidified with 10% HCl, cooled on ice, and filtered. The crude residue was taken up in 1:1 DMSO:MeCN, filtered through a 0.22 µM nylon spin filter, and purified by preparative HPLC.

$^1$H NMR (500 MHz, d$_6$-DMSO) δ: 8.10 (1H, s); 8.04 (1H, d, J=1.7 Hz); 7.65 (1H, d, J=1.7 Hz); 7.64 (1H, d, J=1.7 Hz); 7.44 (2H, d, J=8.6 Hz); 7.22 (1H, d, J=16.0 Hz); 7.14 (1H, d, J=8.0 Hz); 7.05 (1H, d, J=16.0 Hz); 6.95 (2H, bs); 6.63 (2H, d, J=8.6 Hz); 1.49 (4H, quintet, J=7.4 Hz); 1.30 (4H, sextet, J=7.4 Hz); 0.90 (6H, t, J=7.4 Hz). HR-ESI, calculated for C$_{35}$H$_{33}$Cl$_2$NO$_6$S, 665.1406. found [M$^+$]=665.1382.

Example 2

Testing of VF1.4.Cl and VF2.4.Cl in HEK Cells

To test the efficacy of VF1.4.Cl and VF2.4.Cl as voltage sensors, the probes were loaded in HEK cells at a concentration of 2 µM. Passive staining for 15 minutes at 37° C. resulted in excellent membrane localization, as established by epifluorescence and confocal microscopy (FIG. 4). In contrast, when di-4-ANEPPS is loaded under identical conditions, significant internalization of the dye is observed. Optimal loading conditions for di-4-ANEPPS require loading for only 10 minutes at 4° C.

Figure 5B:
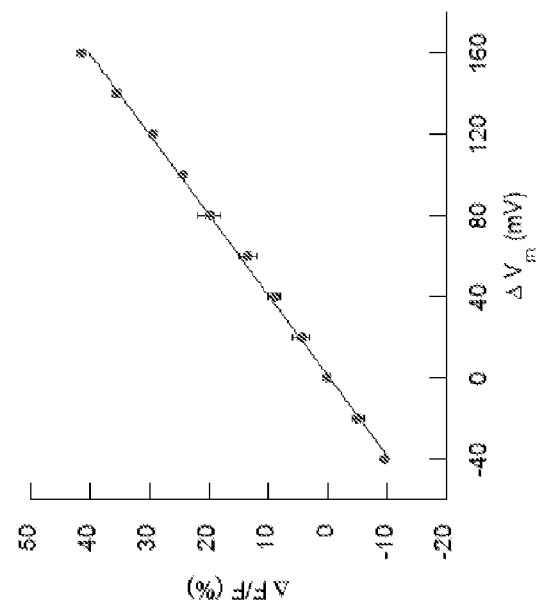
FIG. 5A shows the fluorescence response to voltage steps in neurons and FIG. 5B provides a graph of fractional fluorescence change vs. voltage change.
Figure 5A:
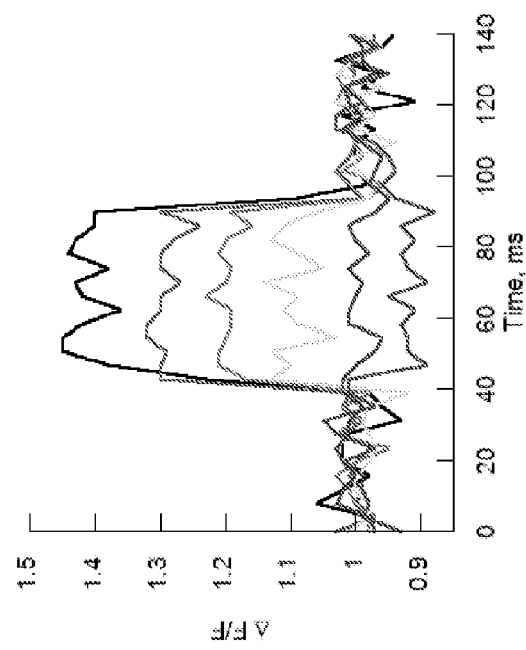

Membrane voltage of cells loaded with VF1.4.Cl or VF2.4.Cl were controlled by making tight-seal whole-cell recordings. Cells were maintained at a holding potential of −60 mV and stepped for 50 ms to various depolarizing and hyperpolarizing potentials (FIG. 5A), while simultaneously acquiring epifluorescence images. For both sensors, depolarizing steps result in fluorescence increases while hyperpolarizing steps decrease fluorescence intensity, in keeping with our proposed mechanism. Plotting the fractional fluorescence change (ΔF/F) versus change in membrane potential reveals sensitivities of 0.20±0.01% and 0.25±0.01% per mV for VF1.4.Cl and VF2.4.Cl respectively. See FIG. 5B. For di-4-ANEPPS, typical values are 0.08-0.12% per mV. The larger changes for VF1.4.Cl and VF2.4.Cl compared to di-4-ANEPPS are somewhat expected, since a PeT-based voltage sensor samples the entire emission spectrum, whereas electrochromic dyes are limited to the edge of the spectrum only. For both probes, the voltage responses are linear across the physiologically relevant ranges of −100 mV to +100 mV. To assess the speed of the optical response to voltage, VF2.4.Cl signals were monitored in response to voltage steps of 100 mV from a holding potential of −60 mV. Fitting the rise and decay transients to mono-exponentials gave values for optical $\tau_{on}$ and $\tau_{off}$ that were indistinguishable from the physiology trace ($\tau_{on,\ phys}$=139±0.2 µs, $\tau_{on\ optical}$=138±14 µs; $\tau_{off,\ phys}$=142±0.4 µs, $\tau_{off,\ optical}$=147±19 µs), suggesting VF2.4.Cl does not suffer from a lag in its response to voltage changes.

The ΔF/F for VF2.4.Cl is relatively insensitive to the excitation wavelength. As opposed to di-4-ANEPPS and other electrochromic dyes (ref the biochemistry paper and the ANINNE6 2004 Denk paper), which are highly sensitive to excitation wavelength, PeT-based sensors yield fluorescent responses which are invariant across their excitation spectra. To establish the invariant nature of the fluorescence response, HEK cells were loaded, as before, with VF2.4.Cl and subjected to depolarizing steps of 100 mV, each time varying the excitation wavelength. Scanning across the excitation spectrum from 500 to 445 nm in 5 nm increments revealed that the fractional response of VF2.4.Cl changes only by approximately 20%. In contrast, di-4-ANEPPS varies by nearly 100%. See FIG. 6B. Excitation at the red edge of the spectrum gives a maximal response whereas excitation at the blue edge gives a response that is some 10- to 20-fold less than the maximal response. By comparison, Calcium Green-1, a PeT-based sensor for $Ca^{2+}$, shows only about a 20% change in ΔF/F across its excitation spectrum. See FIG. 6A. The invariant response of VF2.4.Cl suggests a PeT mechanism is operating in its sensitivity to voltage (FIG. 6C).

Figure 7B:
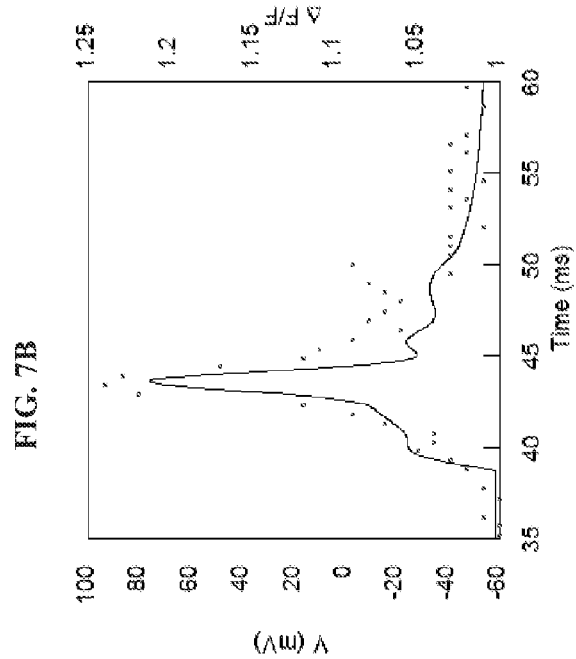
FIG. 7B is a zoomed-in region of the action potential from the graph in FIG. 7A.
Figure 7A:
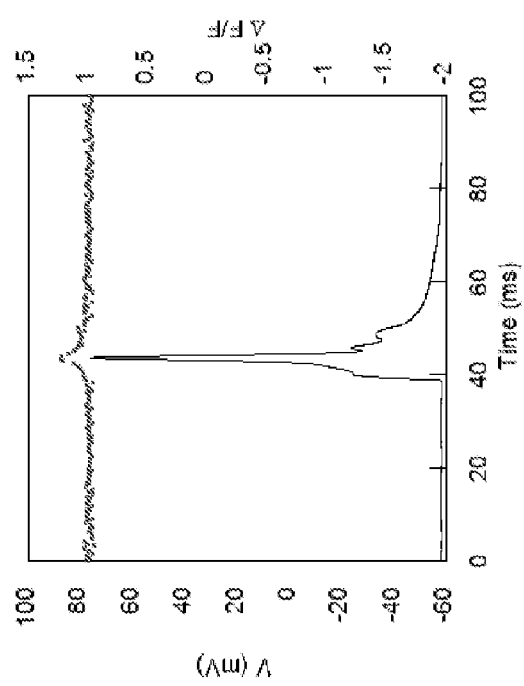
FIG. 7 shows the fluorescence response to current injection in rat hippocampal neurons. Solid black line is recorded electrophysiology trace, dots are optical traces. Traces are single trials.

To assay VF2.4.Cl's utility for monitoring neuronal activity, hippocampal neurons isolated from rats neonates were loaded with 2 µM VF2.4.Cl for 15 minutes, washed twice and imaged. VF2.4.Cl shows membrane localization, but the inhomogeneity of primary culture results in increased background staining when compared against HEK cells. Neurons were patched, current clamped, and injected with a small pulse (250-400 pA, 1-5 ms) to induce action potential firing. By using a high speed EMCCD camera, capable of sampling small regions of interest (ROI) at rates of approximately 2 kHz, enabled single trial optical detection of action potentials. See FIGS. 7A-7B. An action potential with a total voltage change of ~130 mV was well resolved optically and gave a ΔF/F of 24% with a signal-to-noise ratio of 16. Smaller spikes were detectable as well, a 100 mV change gave a ΔF/F of 15% with an SNR of 15. The slightly diminished sensitivity in neurons (0.15% per mV in neurons vs 0.25% per mV in HEK cells) can be explained primarily by the heterogeneous nature of the preparation; overlapping, non-excitable membranes loaded with VF2.4.Cl contribute to a non-responsive fluorescent signal which dilutes the responsive fraction.

Example 3

Characterization of VF Sensors in HEK Cells

Figure 9:
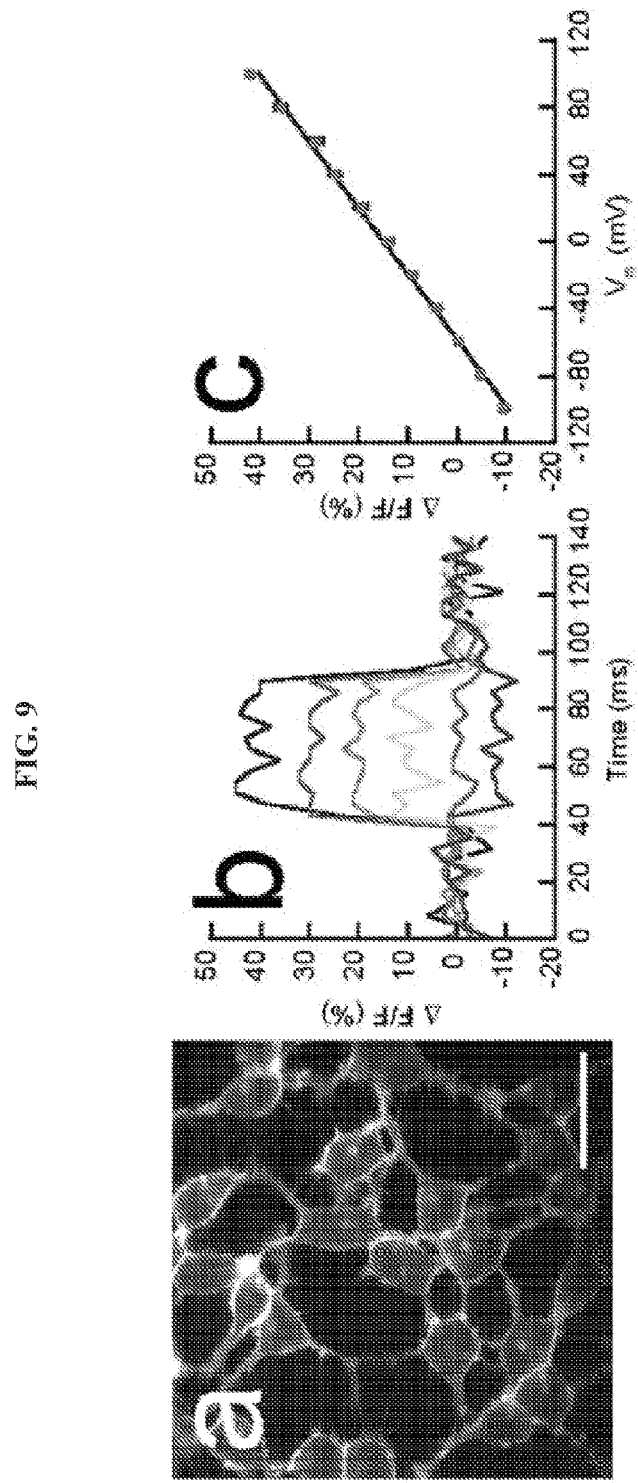
FIG. 9 provides the characterization of exemplary compounds of the invention in HEK cells. (A) Confocal image of HEK 293 cells stained with 2 μM VF2.4.Cl. (Scale bar, 20 μm.) (B) Fractional changes in VF2.4.Cl fluorescence during a series of voltage steps to +100 or −100 from a holding potential of −60 mV (40-mV increments). (C) Fractional changes in VF2.4.Cl fluorescence from B plotted against membrane potential for voltage changes from a holding potential of −60 mV. Each datapoint represents three to four separate measurements. Error bars are SEM.
Figure 10:
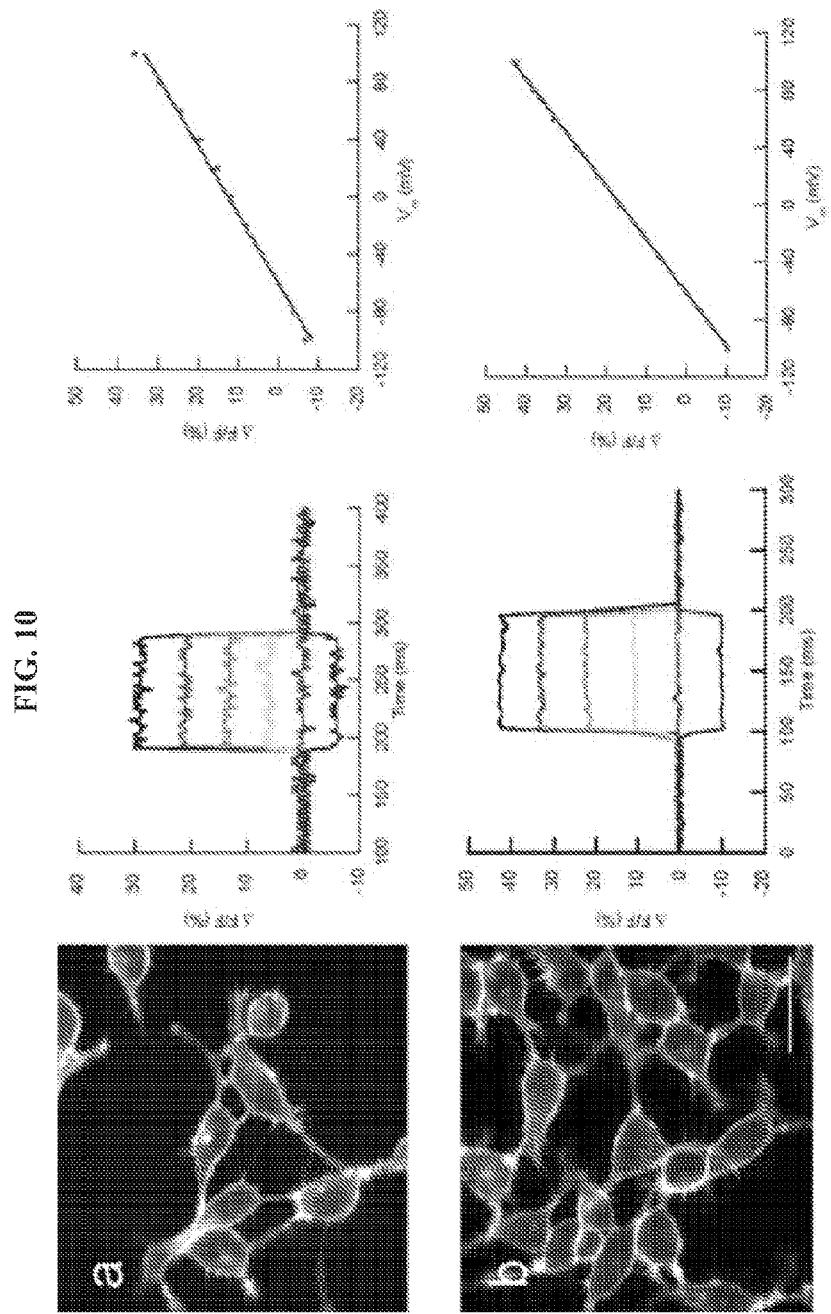
FIG. 10 provides the characterization of exemplary compounds of the invention in HEK cells. Confocal images of HEK 293 cells stained with a) 2 μM VF1.4.Cl or b) 100 nM VF2.1.Cl. (middle) Fractional changes in VF1.4.Cl (upper) or VF2.1.Cl (upper) fluorescence during a series of voltage steps to +100 or −100 from a holding potential of −60 mV (40 mV increments). (right) Fractional changes in VF1.4.Cl (upper) or VF2.1.Cl (lower) fluorescence plotted against membrane potential for voltage changes from a holding potential of −60 mV. Each data point represents 3-4 separate measurements. Error bars are S.E.M. Scale bar=20 μm.

The dibutyl (VFx.4.Cl) dyes stain the cell membranes of HEK293 cells when loaded at a concentration of 2 µM for 15 min at 37° C. in buffer with 0.1% DMSO as cosolvent (FIG. 9A, and FIG. 10). VF2.1.Cl requires even lower dye concentrations (100 nM) and gives bright staining of HEK cell membranes, which is likely to be because of the greater aqueous solubility of VF2.1.Cl compared with VF2.4.Cl in aqueous solution (FIG. 10). The membrane retention of the second generation dyes (VF2.x.Cl) is in contrast to di-4-ANEPPS, which at the same loading conditions, shows significant uptake into internal membranes. The bleach rates of the probes were tested in HEK cells and compared with di-4-ANEPPS. The bleach rates for VF1.4.Cl, VF2.4.Cl, and VF2.1.Cl at 7 W/cm² were measured to be 3.9±0.1×10⁻² 1.8±0.1×10⁻² s⁻¹, and 8.0±0.1×10⁻³ s⁻¹, respectively. These results are two-, four-, and ninefold smaller than di-4-ANEPPS, which has a bleach rate, under identical illumination conditions, of 6.9±0.1×10⁻² s⁻¹.

Example 4

Characterization of the Voltage Response of VF Sensors

Figure 11:
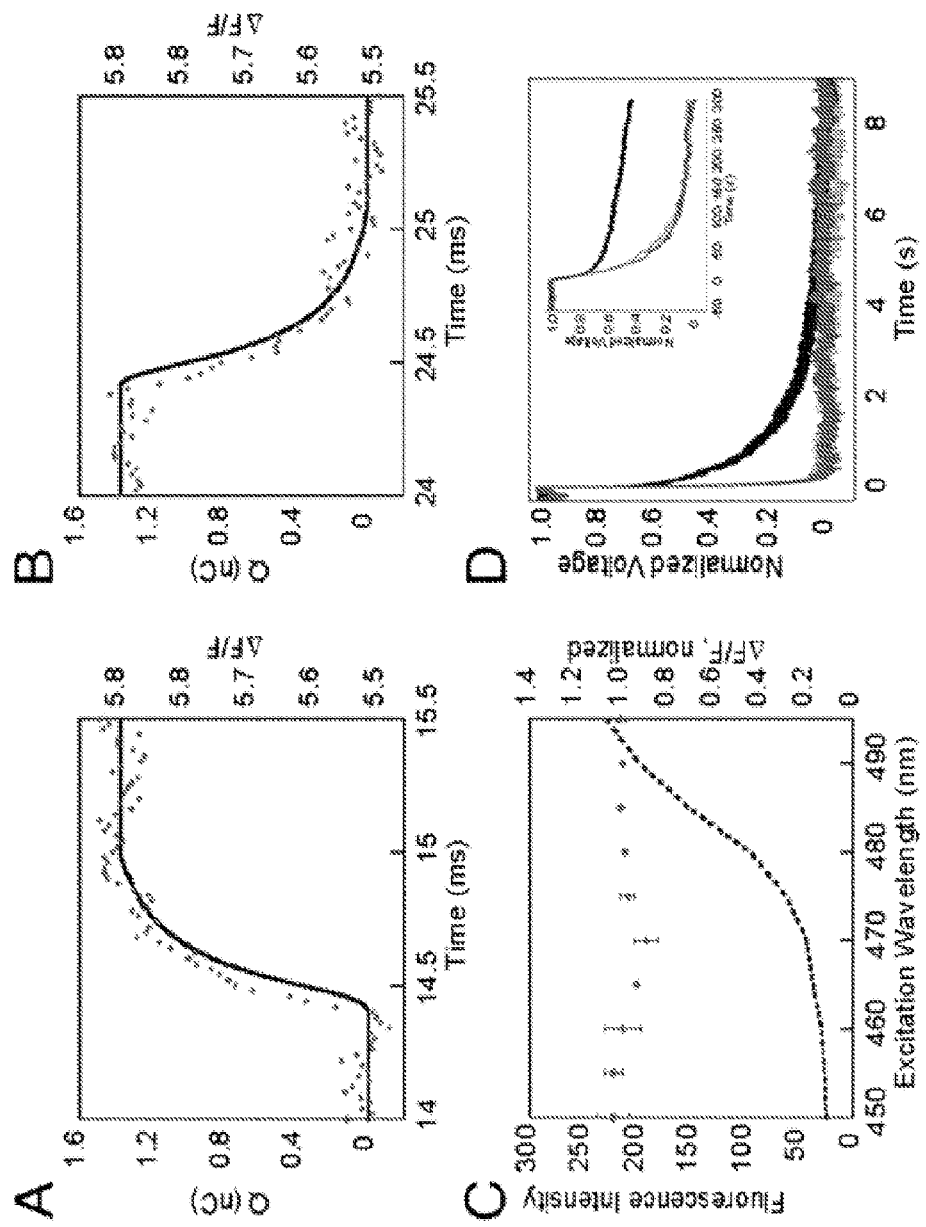
FIG. 11 provides the characterization of the speed, wavelength sensitivity, and capacitance of the VF2 fluorescence response. (A) Rising edge of a 100-mV depolarizing step from −60 mV in HEK cells stained with VF2.4.Cl. (B) Falling edge of the same step. Black, solid trace is the integrated current measured electrophysiologically; red points are the optical recording. Time constants are calculated by fitting a monoexponential equation to each side of the step. Traces are the average of 100 sequential trials. (C) Voltage sensitivity vs. excitation wavelength. The normalized response of VF2.4.Cl to a 100 mV depolarization from −60 mV in HEK cells is plotted in red, and the excitation spectrum in HEK cells is the dotted black line. Error bars are SEM for n=3 experiments. (D) Measurement of capacitative loading in leech Retzius cells. Traces show the normalized voltage decay following hyperpolarizing current injection into Retzius cell stained with 3×VF2.1.Cl (red trace), 3× oxonol 413 (black trace), or nothing (gray trace). (Inset) An expanded time scale revealing no difference between cells stained with VF2.1.Cl and control cells.

We characterized the voltage sensitivity of all three indicators by making tight-seal whole-cell recordings of HEK293 cells stained with the VF sensors. Cells were voltage-clamped at −60 mV holding potential and sequentially stepped to depolarizing and hyperpolarizing potentials at 20-mV increments (FIG. 9B). For all three dyes, depolarizing steps produced fluorescence increases, whereas hyperpolarizing steps produced fluorescence decreases, in keeping with the proposed PeT mechanism. The fluorescence response is linear over the range of −100 mV to +100 mV (FIG. 96), with voltage sensitivities ΔF/F per 100 mV of 20±1% for VF1.4.Cl and 25±1% for VF2.4.Cl. This statistically significant increase in voltage sensitivity (P<0.05, two-tailed Student t test) is expected upon increasing the length of the molecular wire, and is 2.5- to 4-times more sensitive than di-4-ANEPPS, which, in our hands, gives sensitivities of between 6% and 10% ΔF/F per 100 mV. VF2.1.Cl shows fluorescence increases upon depolarization similar to VF2.4.Cl, with a voltage sensitivity of 27±1% per 100 mV. This value is not significantly different from the sensitivity of VF2.4.Cl, suggesting that voltage sensitivity is largely determined by the length of the molecular wire and that the small increase in electron donating ability of the butyl relative to the methyl groups makes only a relatively small contribution to the increased voltage sensitivity of VF2.1.Cl. To investigate the speed of response of VF probes, we again made whole-cell recordings of cells stained with VF2.4.Cl, applied 100-mV depolarizing steps from a holding potential of −60 mV, and recorded both the electrophysiological signals and the optical signals. Fitting the electrophysiological and optical recordings gave identical time constants for both beginning and end of the pulse ($\tau_{ON,\ phys}$=139±0.2 μs, $\tau_{ON,\ optical}$=138±14 μs, $\tau_{OFF,\ phys}$=142±0.4 μs, $\tau_{OFF,\ optical}$=147±19 μs), showing that VF2.4.Cl and related sensors do not introduce any detectable lag in their fluorescence response to voltage, consistent with a PeT-based mechanism for voltage sensing (FIGS. 11A and B).

Figure 12:
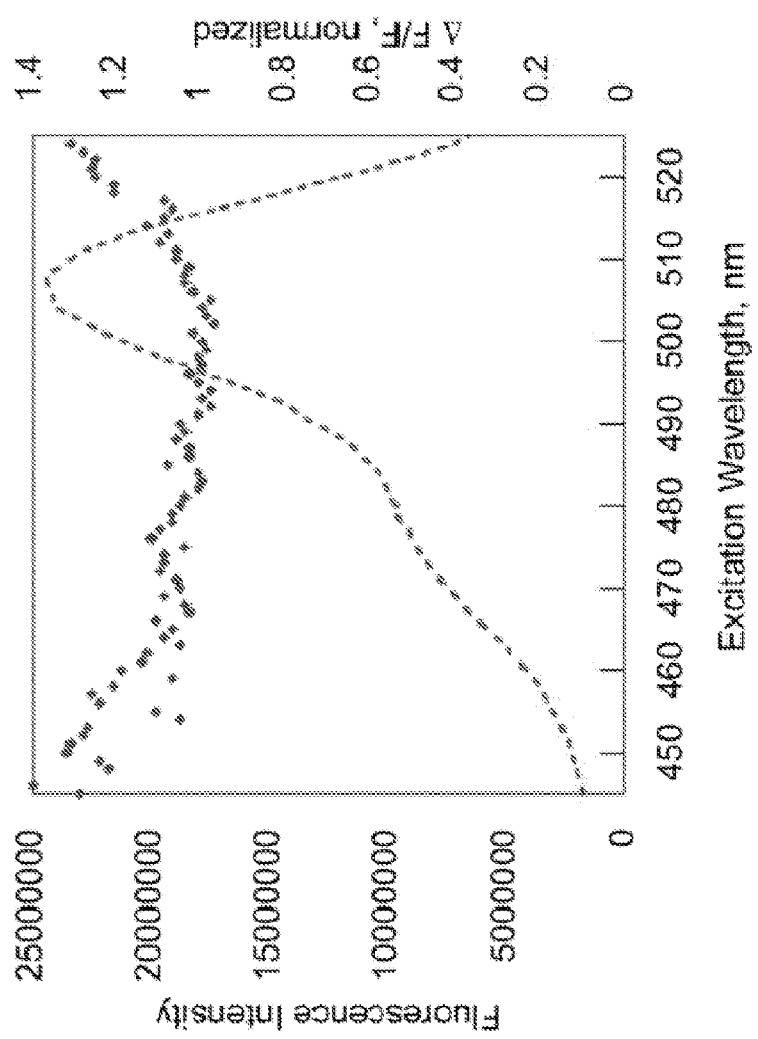
FIG. 12 shows the wavelength sensitivity of CaGreen. Dotted grey spectrum shows an excitation scan of CaGreen in 100 mM Na MOPS with 1 mM EDTA. Red dots depict the normalized fluorescent response to the addition of excess (4 mM Ca2+) vs. the excitation wavelength. The relatively invariant fluorescent response is characteristic of PeT-based fluorescent sensors.

The fluorescence response of VF2.4.Cl to voltage changes is insensitive to the excitation wavelength, as is true for PeT-based probes, such as fluo-3 and Calcium Green-1. We assayed the wavelength dependence of VF2.4.Cl by changing the excitation wavelength in 5-nm steps and determined that the fluorescence response of VF2.4.Cl to a 100-mV depolarization from a holding potential of −60 mV varied only about 15% when testing wavelengths from 445 to 500 nm (FIG. 11C). In comparison, di-4-ANEPPS varies by nearly 100% over its excitation spectrum (32), and the PeT-based $Ca^{2+}$ sensor, Calcium Green-1, varies by ~20% (FIG. 12). These comparisons show that the wavelength independence of the voltage sensitivity is more consistent with PeT than a wavelength-shifting mechanism, such as electrochromism or solvatochromism (a wavelength shift because of alteration in local solvation).

PeT-based molecular wire sensors do not affect neuronal excitability by capacitive loading. We injected hyperpolarizing current into the Retzius cells of leech ganglia preparations and compared the time constants for these voltage steps in ganglia under different dye loading conditions. The ganglia were stained with dye at three times the working concentration [either VF2.1.Cl or diSBA-$C_4$-(3) (14)] and compared with unloaded cells. The presence of the translocating dye oxonol 413 substantially increases the capacitive load on the membrane, as measured by the increase in the RC time constant for the hyperpolarizing injection (FIG. 11D). On the other hand, ganglia loaded with VF2.1.Cl show no difference from control cells, demonstrating that molecular wire sensors place negligible capacitive load on the cell (FIG. 11D), confirming the predictions of the Theoretical Considerations.

Example 5

Detection of Action Potentials by VF2.4.Cl in Mammalian Neurons

Figure 13:
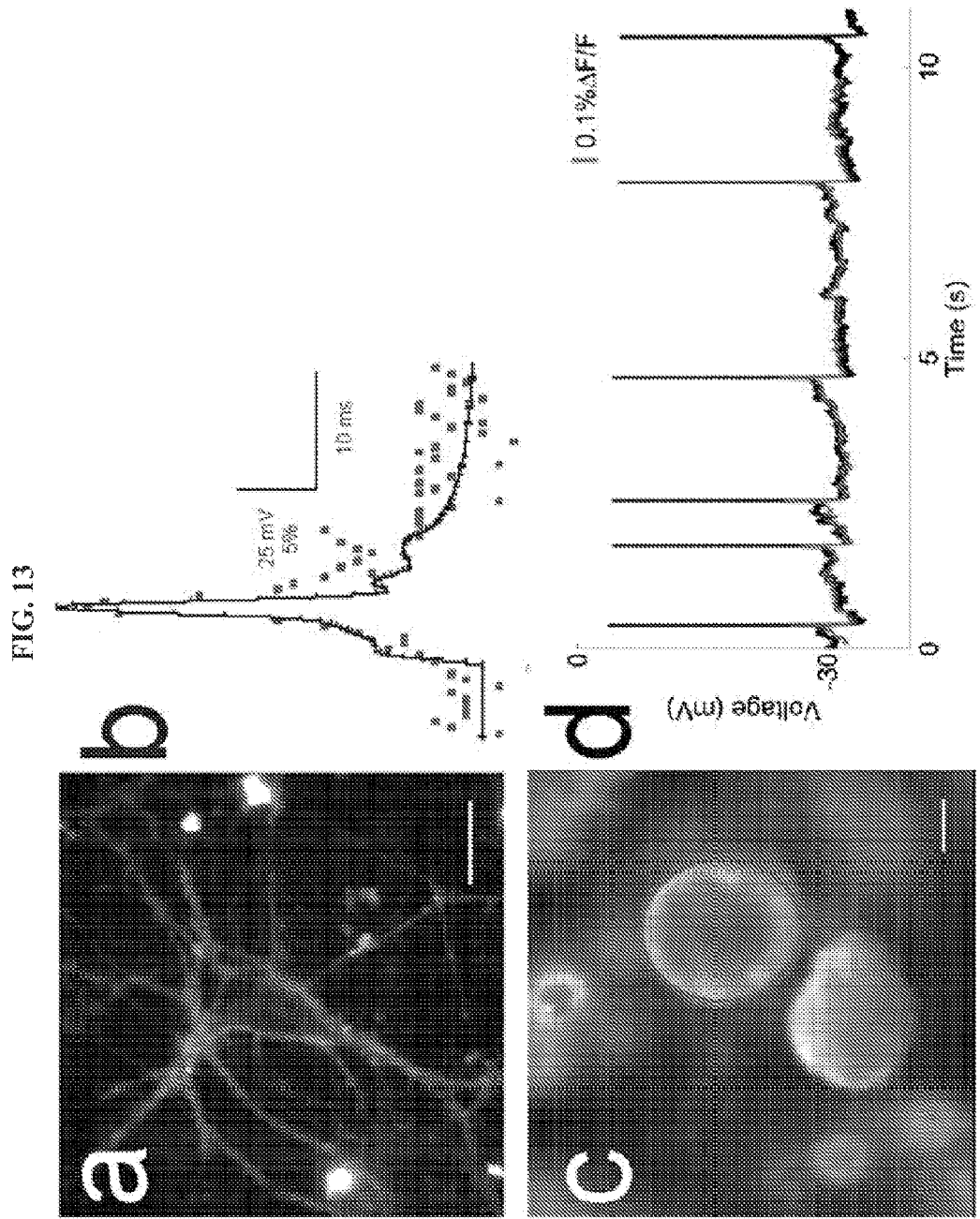
FIG. 13 shows VF2 dyes resolve action potentials in neurons. (A) Rat hippocampal neurons stained with 2 μM VF2.4.Cl for 15 min show strong membrane staining. (Scale bar, 20 μm.) (B) VF2.4.Cl can detected evoked action potentials in rat hippocampal neurons in single trials. The black trace is the recorded electrophysiology signal. Individual points represent the optical signal from VF2.4.Cl captured with a high speed EMCCD camera at a rate of 2 kHz. (C) Optical imaging of spontaneous activity in leech Retzius cells using the dye VF2.1.Cl. Desheathed midbody leech ganglion stained with 200 nM VF2.1.Cl for 15 min. Pixels within the region of interest (red circle around a single Retzius cell body) were averaged in each frame to produce the optical trace. (Scale bar, 25 (D) Simultaneous optical and electrophysiological recording of spontaneous activity in cell from C. The red trace is the hi-pass filtered VF2.1.Cl signal, sampled at 50 Hz. The black trace is the electrophysiological recording, sampled at 10 kHz. The optical trace shows near-perfect matching of the subthreshold membrane potential and a clear detectable signal indicating action potentials. Action potentials have variable amplitudes in the optical traces because of the relatively slow optical sampling rate.

To assess whether VF probes can detect action potentials in single trials, we used cultured rat hippocampal neurons. Bath application of 2 μM VF2.4.Cl showed bright cell staining limited to the cell membranes of neurons and their support cells (FIG. 13A). We then injected current into a neuron under whole-cell patch-clamp mode to trigger single action potentials and used a high-speed, back-illuminated EMCCD camera to track fast optical signals from VF2.4.Cl, enabling us to resolve action potentials in neurons in single sweeps (FIG. 13B). The optical trace matched the physiology trace and gave about a 20% ΔF/F increase in fluorescence and a 16:1 signal-to-noise ratio (SNR) in a single trial. The fact that VF2.4.Cl detected action potentials without spike-timed averaging suggests the possibility of measuring spontaneous action potentials in neurons at sites away from the recording pipette.

Example 6

Monitoring Spontaneous Activity in Leech Ganglia with VF2.1.Cl

Figure 14:
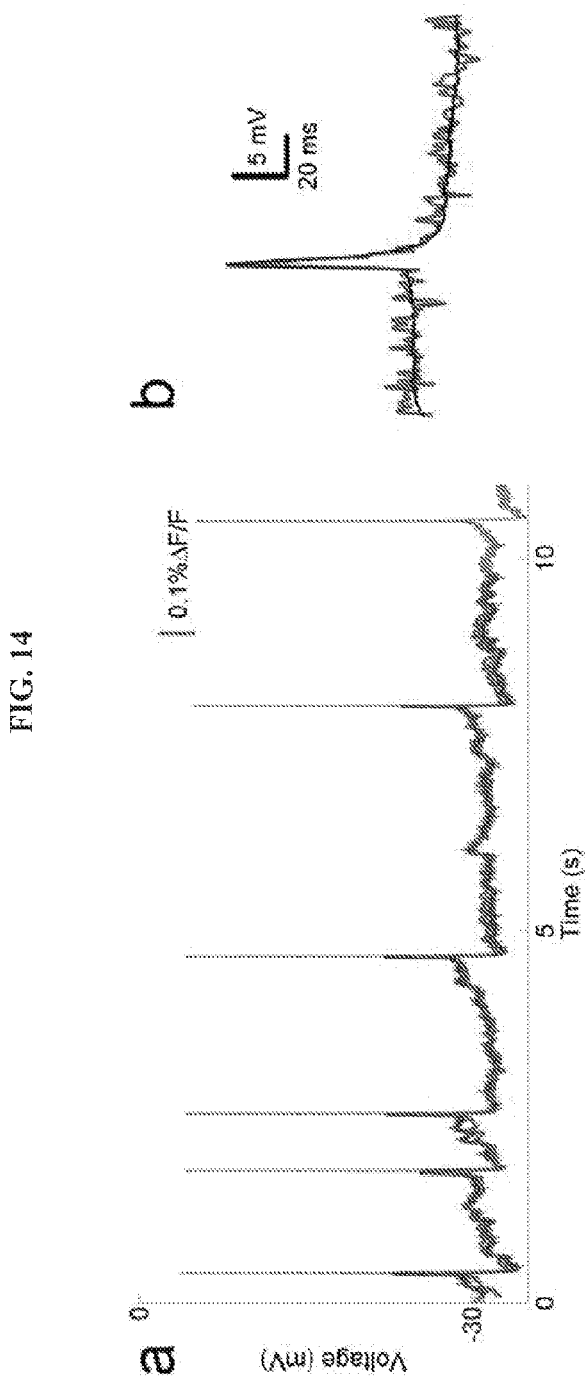
FIG. 14 provides sampling action potentials at slow and fast rates. a) The red trace is a hi-pass filtered VF2.1.Cl optical signal sampled at 50 Hz. The electrophysiological trace has been faded to gray for clarity. The blue trace is the electrophysiological trace sampled at 50 Hz, which shows a similar variability in amplitudes of the action potentials due to the lower sampling rate. b) High-frequency sampling of VF2.1.Cl. The sampling rate of the optical data was increased to 722 Hz by binning pixels in the CCD camera. The optical trace (red) fully follows the Retzius cell action potential (black). However, increased electronic noise decreases the signal-to-noise ratio of the optical signal, making imaging at this rate suboptimal for accurate measurements of the slower, subthreshold signals.

A more stringent test of the usefulness of the PeT-based VSD is to determine whether it can accurately measure subthreshold activity in heterogeneous preparations. For this test we used leech ganglia, because their neurons have been well studied using both electrophysiological and other VSD recordings (14, 33-35). We isolated a midbody ganglion and stained it with VF2.1.Cl for 15 min at 22° C. (FIG. 13C). Insertion of a sharp electrode (25 MΩ) into a Retzius cell to enabled recording of its spontaneous activity while simultaneously recording the fluorescence signals from the same cell. When sampling at a rate of 50 Hz, the optical recording (FIG. 13D, red trace) faithfully followed the subthreshold fluctuations in the electrical recording (black trace). The optically recorded spikes are truncated as a result of undersampling the optical signal; sampling at a higher rate (722 Hz) fully resolved the action potentials, but introduced a significant amount of sampling noise (FIG. 14). Although the action potential was subsampled at just 50 Hz, there is still a reliable transient in the optical trace that indicates the time when an action potential occurs, which is often what is needed.

The PeT-based VSDs show significant improvement in speed and accuracy compared with FRET-based VSDs previously used for leech recordings (33, 36-38), which in turn had superseded electrochromic dyes (14). The improvement in the recording of membrane potential fluctuations is not the result of a greater sensitivity (the ΔF/F for both the FRET and PeT dyes is about 10% per 100 mV in leech recordings), but to a greater SNR. The PeT-based VSD produces a much brighter signal, one that is well above the photon noise levels of the dye and the dark noise level of the camera. Increasing the concentration of the FRET-based dye does increase its SNR, but the consequent increase in the cell's capacitance (FIG. 11D) makes the dye useless for recording either action potentials or synaptic potentials. Tests of the toxicity and bleaching of the PeT-based VSD similar to those performed on the FRET-based dyes (14) show that the PeT-based VSD has a slower rate of bleaching and is less toxic than the FRET-based dyes. Hence, considering all measures, the PeT-based VSD performs better than the FRET-based dyes (39).

Discussion

Optimal VSDs would have large, fast responses to changes in voltage, place little or no capacitive load on the membrane, photobleach slowly with minimal photodynamic damage, and would be synthetically tractable for rational chemical modification and genetic targetability. We believe that the VF family of PeT-based probes surpass previous VSD classes by these criteria. The three PPV molecular wire, PeT-based molecules we tested (VF1.4.Cl, VF2.4.Cl, and VF2.1.Cl) exhibit good membrane staining and 20-27% ΔF/F per 100-mV increases in fluorescence upon depolarization in HEK cells. These molecules possess the fast kinetics ($\tau_{ON/OFF}$<<140 μs) and wavelength-independent voltage sensitivity consistent with a PeT mechanism for sensing voltage. Measurements of capacitance in leech neurons show that an insignificant amount of capacitive load is placed on the membrane. The advantages of PeT-based dyes over both electrochromic and FRET-based methods for optical voltage sensing are described below and summarized in Table 1. A fourth technique, making use of genetically encoded voltage sensors, offers a promising method for optically monitoring voltage changes because the fluorescent proteins can be targeted to cells of interest, thereby increasing the SNR of the fluorescence response. In practice, however, fluorescent protein voltage sensors suffer from low sensitivity [0.5% (40) to 10% ΔF/F per 100 mV (41)], nonlinear responses (42) and slow kinetics (tens to hundreds of milliseconds). Newer efforts have made use of proton translocation within bacterial rhodopsins (43), but although these show large voltage sensitivities, the response time is still in the millisecond range, quantum efficiencies are very low, and their expression limited to prokaryotic systems. Voltage-driven translocation of ions through the membrane will generally add much more capacitative load than electron translocation during transient excited states (44).

VSDs using a PeT-based molecular wire approach should be highly sensitive. Because a full electronic charge travels through a substantial fraction of the transmembrane voltage (11 Å for VF1.4.Cl, 17 Å for VF2.4.Cl and VF2.1.Cl, or 37% and 57% of the 30 Å low-dielectric constant core of the plasma membrane) the change in driving force for PeT is large. For example, a 100-mV depolarization changes the PeT driving force by 0.05 eV (one electron×half of 100-mV potential, or 0.05 V). Because PeT is a thermally controlled process, the value of 0.05 eV is large relative to the value of kT at 300 K (0.026 eV), yielding a large dynamic range between the rates of PeT at resting and depolarized potentials. FRET-based VSDs will have similar sensitivities; lipid-soluble mobile anions transverse distances calculated to be between 0.4 (16) and 0.6 (45) of the total membrane width, resulting in ΔG of ~0.05 eV for 100-mV depolarization, compared with a kT of 0.026 eV for the thermally activated process.

In contrast, electrochromic dyes have smaller ΔG values, 0.003 (46) to 0.02 (47) eV, and larger comparison energies. Because the interaction is a photochemically controlled process, the energy of the exciting photon is the comparison energy, which is 1.5-2 eV for dyes in the blue-to-green region of the spectrum. Therefore, PeT and FRET dyes have large changes in energy versus their comparison energy (0.05 eV vs. 0.026 eV), giving high sensitivities; electrochromic dyes have small changes compared with the excitation photon (0.003-0.02 eV vs. 2 eV), producing low voltage sensitivity.

The nature of the PeT mechanism also predicts that the kinetics of voltage sensing will be fast; forward electron transfer occurs on the nanosecond timescale as fluorescence is quenched, and back-electron transfer completes the cycle and occurs on a microsecond timescale or faster, meaning that the slow step, electron-hole recombination, finishes a full three orders-of-magnitude faster than an action potential. Electrochromic dyes display even faster kinetics, as forward charge shift occurs with absorbance, on the femtosecond time scale, and resolves itself upon emission of a photon, enabling these dyes to keep time with the fastest spiking neurons. FRET pair VSDs depend upon the migration of a lipophilic anion through an unstirred lipid bilayer and display kinetics in the millisecond-to-second time regime, limiting their application to monitoring only slow transients.

Because PeT shuttles an electron across the membrane and back on a microsecond or faster timescale, driven by photons rather than membrane potential changes, no capacitative loading should be observed. The same holds true for electrochromic dyes, which transfer electrons on even faster time scales. One disadvantage of electrochromic dyes is that they require the entire voltage-sensing chromophores to be rigid to enable π orbital overlap, quantum yield, efficient charge transfer, and maximization of voltage sensitivity (22). Such rigidity hinders synthesis and water solubility and may explain why electrochromic dyes are not improved by lengthening their chromophores. PeT probes do not require the entire molecular wire to be rigidly coplanar, and synthesis of longer wires is feasible.

PeT-sensing allows the entire emission spectrum to be used for monitoring voltage, because the quenching mechanism alters the $\Phi_{Fl}$, decreasing the brightness of the dye, and does not shift the wavelength as do electrochromic methods. Because photons are not wasted, this allows lower intensity light to be used in experiments, reducing phototoxicity and increasing the duration of experimental procedures. The performance of electrochromic dyes has plateaued over four decades of development. Excitation at the far-red edge of the spectrum gives voltage sensitivities ranging from −35% to −52% ΔF/F per 100 mV; however, at the edge of the spectrum, the intensity is far below the peak and the voltage response becomes nonlinear (48).

Several limitations of the VF dyes remain to be addressed. VF derivatives are not yet genetically targetable. The sensors are readily taken up by the cell membranes of all tissue, increasing nonresponsive background fluorescence and decreasing the SNR. For heterogeneous preparations, such as intact leech ganglia and brain slices, this becomes an increasingly important issue, and one method to address this concern is through the genetic targeting of VSDs. VF sensors lend themselves to chemical derivatization, and efforts are underway to modify VF probes for targeting to genetically defined circuits of neurons.

Another drawback is that VF PeT sensors are not as sensitive to voltage as hoped. Our first derivatives show sensitivities ranging from 20-27% ΔF/F per 100 mV, and the most sensitive of existing electrochromic dyes exhibit −28% ΔF/F per 100-mV sensitivities in the linear range (47). Although it is encouraging that the first derivatives display sensitivities on a level approaching the most sensitive electrochromic dyes, we believe ample chemical space exists for improving the voltage sensitivity of molecular wire platforms. Because the voltage sensitivity is controlled by PeT, the efficiency of PeT can be rationally tuned (49) by altering the electron affinities of the donor, wire, and acceptor to maximize the fluorescence turn-on in response to depolarizations. Additionally, extending the molecular wire to span an even greater distance across the plasma membrane should increase sensitivity as the transferred electron samples more of the electric field. The modular nature of the VF synthesis allows for rapid interchange of coupling partners to quickly assemble and assess the voltage sensitivity of an array of compounds.

In summary, we present a unique method for monitoring voltage in neurons based on the voltage-sensitive PeT from an electron-rich donor to fluorescent reporter attached via a membrane-spanning molecular wire. The VF family of sensors have large, linear, turn-on fluorescence responses to depolarizing steps (20-27% ΔF/F per 100 mV), fast kinetics (τ<<140 µs), and negligible capacitative loading. VF2.4.Cl can detect and resolve evoked action potentials in primary culture hippocampal neurons, and VF2.1.Cl can monitor spontaneous spiking and synaptic potentials in leech Retzius cells with sensitivity and time-course essentially identical to the recorded electrophysiology signal. VF sensors provide a practical alternative to currently available VSDs, and future derivatives of the molecular wire platform will increase our ability to optically monitor the temporal and spatial dynamics of neuronal activity in defined circuits of neurons.

Methods

Imaging, electrophysiology, cell culture, leech imaging and electrophysiology, and data analysis methods applied in Examples 3 to 6 are detailed below.

Imaging, Electrophysiology, and Cell Culture.

HEK293 cells were cultured in DMEM (CellGrow) supplemented with 10% FBS, 1% penicillin/streptomycin (Invitrogen) and plated on glassbottom culture dishes (35 mm dish, 14 mm microwell with No. 0 coverglass) (MatTek Corporation). Hippocampal neurons were dissected from postnatal day 0 or 1 rat pups and plated on poly-D-lysine-coated glassbottom culture dishes. Neuronal recordings were made 14-28 days in culture.

Electrophysiological recordings of HEK293 cells and cultured neurons were performed with an Axopatch 200A or 200B amplifier (Molecular Devices) at room temperature. The signals were digitized with Digidata 1332A and recorded with pCLAMP 9 software (Molecular Devices) on a PC. Analysis of electrophysiological data was done with AxoGraph X (AxoGraphX), pCLAMP 9, and/or ClampFit (Molecular Devices). For most experiments the extracellular solution consisted of (in mM) 145 NaCl, 20 glucose, 10 HEPES, 3 KCl, 2 $CaCl_2$, 1 $MgCl_2$ (pH 7.35, 310 mOsm). The intracellular solution contained (in mM) 115 potassium gluconate, 10 BAPTA tetrapotassium salt, 10 HEPES, 5 NaCl, 10 KCl, 2 ATP disodium salt, 0.3 GTP trisodium salt (pH 7.25, 290 mOsm).

For studies to determine excitation sensitivity of dyes, illumination was provided by a Polychrom IV light source (T.I.L.L. Photonics GMBH) with a mechanical shutter (Uniblitz VS25). For all other studies, light was provided by an Xenon arc lamp powered by an Optiquip Power supply (Optiquip) with a mechanical shutter controlled by a Lambda 10-2 controller (Sutter). Light from the Xenon arc lamp was filtered through a 480 nm filter (30 nm bandpass, Chroma), a 510 nm dichroic (Semrock), a 530 nm emission filter (50 nm bandpass, Semrock), and focused through a 40×/1.4 oil objective. For di-4-ANEPPS imaging, a 625 nm emission filter with a 50 nm bandpass was used. Bleaching studies used identical illumination conditions (480/30 nm excitation, 510 nm dichroic, 7 W/cm$^2$ output) and were corrected by normalizing for the extinction coefficient at the excitation wavelengths (465-495 nm).

Epifluorescence images were acquired with either a Cascade II 512, CoolSNAP cf2 or Evolve 128 (Photometrics) controlled with Slidebook software (Intelligent Imaging Innovations). Confocal images were acquired on a Zeiss LSM 5Live confocal microscope (Zeiss). For confocal imaging, a 40×/1.2 water objective was used, along with excitation provided at 488 nm by an argon laser. Emission was collected with a 505 nm longpass filter after passage through a 490 nm dichroic/beamsplitter.

To measure the speed of VF2.4.Cl response, the camera was replaced with a PMT (Hamamatsu). A diaphragm inserted into the light path allowed sampling of fluorescence from just the patch-clamped cell. A brief (10 ms) depolarization was delivered and both the optical and electrophysiological signals were recorded at a sampling rate of 50 kHz. 100 trials were averaged and the resulting rise and fall times were fit using Clampfit software (Molecular Devices).

Leech Imaging and Physiology.

Isolated midbody ganglia (Ganglia 8-16) were dissected from *Hirudo medicinalis* and the ventral side was desheathed using standard procedures. The voltage sensitive dye was combined with HEPES saline down to the desired concentration (100-300 nM), and 1.5 μL of a 20% (w/v) solution of Pluronic F-127 in DMSO. The dye was then continuously pumped over the ganglion to help with penetration into the cell membranes for 20-30 minutes. This follows similar procedure with the coumarin partner of the FRET voltage dye pair. [Briggman, K. L., Abarbanel, H. D. & Kristan, W. B., Jr. Optical imaging of neuronal populations during decision-making. *Science* 307, 896-901 (2005).]

Electrophysiological measurements were made with paired electrode recordings with resistances in the range of 20-40 MΩm. Electrode 1 acted as the recording electrode, which constantly monitored membrane potential, and electrode 2 acted as the current injecting electrode. Capacitance measurements were made by injecting 1 nA square wave of hyperpolarizing current into the cell. The resulting decaying exponential approach of the membrane potential towards a hyperpolarized steady state was normalized to its minimum and maximum values and compared across the different conditions (FIG. 11d). The capacitance C was calculated with the formula C=tau*I/ΔV, where I=1 nA and the hyperpolarization ΔV was 15-18 mV. Tau was measured two ways: 1) the time required for the normalized curve to reach (1−1/e); 2) the time constant of the best fit exponential or sum of exponentials. Neither measure changed the quality of the result showing that no capacitative load was added with the PeT-VSD, while significant load was added with the FRET dye. Spontaneous Retzius cell activity was measured with a single electrode.

Imaging was done with a Cascade 128+ EMCCD camera (Photometrics). The filter set was standard for FITC. The fluorescence illumination was from an LED that has its peak excitation wave-length in the excitation range for FITC. Image acquisition rates for the spontaneous imaging were made at 50 Hz at 128×128 pixel resolution under a 20×, 0.5 NA objective. The high-frequency imaging of the Retzius action potential was done at 722 Hz (the maximum rate achievable for this camera with 1 ms exposure time), with 4×4 pixel binning (32×32 pixel resolution), under a 40×, 0.8 NA objective. The binning and higher NA of the objective allowed for faster acquisition rates and for more light collection, bringing the light levels high enough to be above the dark noise of the camera. Acquisition and analysis were run with custom-made software. The data is stored in Matlab-readable files.

Data Analysis

For voltage sensitivity measurements, regions of interest were drawn around clamped cells and the mean fluorescence measured in ImageJ or Slidebook. For HEK cells, background fluorescence was subtracted by measuring the fluorescence where no cells grew. For experiments in neurons, the background fluorescence was not subtracted. In all cases, ΔF/F was calculated by dividing the fluorescence signal by the average fluorescence for a baseline of 10-20 frames prior to stimulation.

Theoretical Considerations

Theoretical considerations of capacitative load are detailed below.

To estimate the externally-detectable amount of charge transfer driven by light, we start by noting that each dye molecule of extinction coefficient ∈ (in units of $M^{-1}cm^{-1}$) has an optical cross-section σ (in cm$^2$) of ∈ (1000 cm$^3$/L)(ln 10)/$N_0$, where $N_0$ is Avogadro's number. For reasonably monochromatic light of intensity W (in watts/cm$^2$) at wavelength λ, the photon flux I (in photons□cm$^{-2}$ s$^{-1}$) is Wλ/hc, where h and c are Planck's constant and the speed of light respectively. Each dye molecule is excited at a rate of $I\sigma$ (units of $s^{-1}$), after which it has a probability p of undergoing photoinduced electron transfer (PeT), in which an electron of charge q (=$1.602 \times 10^{-19}$ coulombs) travels a fraction $\eta$ of the thickness of the insulating portion of the membrane. The mean charge displacement per unit time detectable outside the membrane is $I\sigma pq\eta$. Each charge pulse lasts for $\tau$ seconds before the electron returns to its original position by electron-hole recombination. At steady state in a population of dye molecules (at a surface density S in molecules/cm$^2$) asynchronously absorbing photons, the forward and backwards currents are both of magnitude $SI\sigma pq\eta$ and cancel each other out. However, after a sudden change of membrane potential has changed p to p', the rate of forward charge displacement due to PeT will be $SI\sigma p'q\eta$, whereas for a time $\tau$ the rate of backward charge displacement due to charge recombination will still be $SI\sigma pq\eta$. Therefore the net charge displacement will be $SI\sigma(\Delta p)q\eta\tau$. Note that the charge movement is strictly dependent on illumination, unlike the voltage-driven movement of a lipid soluble ion or a gating charge on an ion channel.

A crude upper limit on the surface density S is $10^5$ molecules/($\mu$m)$^2$=$10^{13}$ molecules/cm$^2$, corresponding to about 1 dye molecule per 10 phospholipid molecules in the outer leaflet. We know $\in$ at 480 nm=$2.5 \times 10^4 M^{-1} cm^{-1}$, from which $\sigma$=$9.55 \times 10^{-17}$ cm$^2$. Our typical excitation intensity W at 480 nm is 0.7 W/cm$^2$, from which the photon flux I is $1.76 \times 10^{18}$ photons/(cm$^2$ s) and $I\sigma$=162 s$^{-1}$. If we assume p=0.5, then $\Delta p$ would need to be 0.1 to explain a 20% change in fluorescence intensity for 100 mV depolarization. The distance from the aniline nitrogen to the highly hydrophilic sulfonate group, ~1.7 nm, is a reasonable upper limit for the distance that the electron could travel within the low-dielectric region of the membrane, whose overall thickness is ~3 nm [Andersen, O. S. & Koeppe, R. E., 2nd. Bilayer thickness and membrane protein function: an energetic perspective. *Ann. Rev. Biophys. Biomol. Struct.* 36, 107-30 (2007).], so an upper limit on $\eta$ is 0.57. The greatest uncertainty is in $\tau$, the lifetime of the PeT state before charge recombination back to the ground state. Rate constants for charge recombination in other donor-wire-acceptor examples [Davis, W. B., Svec, W. A., Ratner, M. A. & Wasielewski, M. R. Molecular-wire behaviour in p-phenylenevinylene oligomers. *Nature* 396, 60-63 (1998).] [de la Torre, G., Giacalone, F., Segura, J. L., Martin, N. & Guldi, D. M. Electronic communication through pi-conjugated wires in covalently linked porphyrin/C-60 ensembles. *Chem. Eur. J.* 11, 1267-1280 (2005).] range from $10^6$ to >$10^9$ s$^{-1}$, corresponding to $\tau$=1 $\mu$s to <1 ns. The shorter values of $\tau$ come from molecular wires similar in length to ours, whereas the higher $\tau$ values are from much longer wires. Nevertheless, if we take 1 $\mu$s as a conservative upper limit, the net charge displacement $SI\sigma(\Delta p)q\eta\tau$ is $1.5 \times 10^{-11}$ coul/cm$^2$. For comparison, when a typical biological membrane of 1 $\mu$F/cm$^2$ is depolarized by 100 mV, the ordinary capacitative charge is $10^{-7}$ coul/cm$^2$. Therefore the voltage sensor will add at most 0.015% to the capacitative load. The key reason this is so negligible is that each molecule spends only $I\sigma\tau$ (<<0.1%) of its time in the PeT state. If lipid-soluble ions could be loaded at the same density S, and if their probability for residing on either surface were to change by $\Delta p$=0.1, and if their $\eta$ were 0.63 as measured for dipicrylamine in squid axon membranes [Fernandez, J. M., Taylor, R. E. & Bezanilla, F. Induced capacitance in the squid giant axon. *J. Gen. Physiol.* 82, 331-346 (1983).], their charge displacement $S(\Delta p)q\eta$ would be $1.0 \times 10^{-7}$ coul/cm$^2$, which would double the total capacitative load.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

1. Scanziani M, Häusser M (2009) Electrophysiology in the age of light. Nature 461: 930-939.
2. Peterka D S, Takahashi H, Yuste R (2011) Imaging voltage in neurons. Neuron 69:9-21.
3. Poenie M, Alderton J, Tsien R Y, Steinhardt R A (1985) Changes of free calcium levels with stages of the cell division cycle. Nature 315:147-149.
4. Tsien R Y, Rink T J, Poenie M (1985) Measurement of cytosolic free Ca2+ in individual small cells using fluorescence microscopy with dual excitation wavelengths. Cell Calcium 6:145-157.
5. Grynkiewicz G, Poenie M, Tsien R Y (1985) A new generation of Ca2+ indicators with greatly improved fluorescence properties. J Biol Chem 260:3440-3450.
6. Minta A, Kao J P, Tsien R Y (1989) Fluorescent indicators for cytosolic calcium based on rhodamine and fluorescein chromophores. J Biol Chem 264:8171-8178.
7. Nagai T, Sawano A, Park E S, Miyawaki A (2001) Circularly permuted green fluorescent proteins engineered to sense Ca2+. Proc Natl Acad Sci USA 98:3197-3202.
8. Miyawaki A, et al. (1997) Fluorescent indicators for Ca2+ based on green fluorescent proteins and calmodulin. Nature 388:882-887.
9. Tian L, et al. (2009) Imaging neural activity in worms, flies and mice with improved GCaMP calcium indicators. Nat Methods 6:875-881.
10. Mank M, et al. (2008) A genetically encoded calcium indicator for chronic in vivo two photon imaging. Nat Methods 5:805-811.
11. Heim N, Griesbeck O (2004) Genetically encoded indicators of cellular calcium dynamics based on troponin C and green fluorescent protein. J Biol Chem 279: 14280-14286.
12. Palmer A E, et al. (2006) Ca2+ indicators based on computationally redesigned calmodulin-peptide pairs. Chem Biol 13:521-530.
13. Horikawa K, et al. (2010) Spontaneous network activity visualized by ultrasensitive Ca (2+) indicators, yellow Cameleon-Nano. Nat. Methods 7:729-732.
14. Cacciatore T W, et al. (1999) Identification of neural circuits by imaging coherent electrical activity with FRET-based dyes. Neuron 23:449-459.
15. González J E, Tsien R Y (1997) Improved indicators of cell membrane potential that use fluorescence resonance energy transfer. Chem Biol 4:269-277.
16. González J E, Tsien R Y (1995) Voltage sensing by fluorescence resonance energy transfer in single cells. Biophys J 69:1272-1280.
17. Sjulson L, Miesenbock G (2008) Rational optimization and imaging in vivo of a genetically encoded optical voltage reporter. J Neurosci 28:5582-5593.
18. Akemann W, Lundby A, Mutoh H, Knöpfel T (2009) Effect of voltage sensitive fluorescent proteins on neuronal excitability. Biophys J 96:3959-3976.

19. Wang D, Zhang Z, Chanda B, Jackson M B (2010) Improved probes for hybrid voltage sensor imaging. Biophys J 99:2355-2365.
20. Bradley J, Luo R, Otis T S, DiGregorio D A (2009) Submillisecond optical reporting of membrane potential in situ using a neuronal tracer dye. J Neurosci 29:9197-9209.
21. Chanda B, et al. (2005) A hybrid approach to measuring electrical activity in genetically specified neurons. Nat Neurosci 8:1619-1626.
22. Hubener G, Lambacher A, Fromherz P (2003) Anellated hemicyanine dyes with large symmetrical solvatochromism of absorption and fluorescence. J Phys Chem B 107: 7896-7902.
23. Grinvald A (1983) Fluorescence monitoring of electrical responses from small neurons and their processes. Biophys J 42:195-198.
24. Fluhler E, Burnham V G, Loew L M (1985) Spectra, membrane binding, and potentiometric responses of new charge shift probes. Biochemistry 24:5749-5755.
25. Jacobs J M, Meyer T (1997) Control of action potential-induced Ca2+ signaling in the soma of hippocampal neurons by Ca2+ release from intracellular stores. J Neurosci 17:4129-4135.
26. Davis W B, Svec W A, Ratner M A, Wasielewski M R (1998) Molecular-wire behaviour in p-phenylenevinylene oligomers. Nature 396:60-63.
27. de Silva A P, et al. (1995) New fluorescent model compounds for the study of photoinduced electron transfer: The influence of a molecular electric field in the excited state. Angew Chem Int Ed Engl 34:1728-1731.
28. Adams S R (2010) How calcium indicators work. Cold Spring Harbor Protocols 2010: pdb.top70.
29. de la Torre G, Giacalone F, Segura J L, Martin N, Guldi D M (2005) Electronic communication through pi-conjugated wires in covalently linked porphyrin/C60 ensembles. Chemistry 11:1267-1280.
30. Li L S (2007) Fluorescence probes for membrane potentials based on mesoscopic electron transfer. Nano Lett 7:2981-2986.
31. Garner L E, et al. (2010) Modification of the optoelectronic properties of membranes via insertion of amphiphilic phenylenevinylene oligoelectrolytes. J Am Chem Soc 132: 10042-10052.
32. Montana V, Farkas D L, Loew L M (1989) Dual-wavelength ratiometric fluorescence measurements of membrane potential. Biochemistry 28:4536-4539.
33. Briggman K L, Abarbanel H D, Kristan W B, Jr. (2005) Optical imaging of neuronal populations during decision-making. Science 307:896-901.
34. Salzberg B M, Grinvald A, Cohen L B, Davila H V, Ross W N (1977) Optical recording of neuronal activity in an invertebrate central nervous system: Simultaneous monitoring of several neurons. J Neurophysiol 40:1281-1291.
35. Ross W N, Arechiga H, Nicholls J G (1987) Optical recording of calcium and voltage transients following impulses in cell bodies and processes of identified leech neurons in culture. J Neurosci 7:3877-3887.
36. Taylor A L, Cottrell G W, Kleinfeld D, Kristan W B, Jr. (2003) Imaging reveals synaptic targets of a swim-terminating neuron in the leech CNS. J Neurosci 23:11402-11410.
37. Briggman K L, Kristan W B, Jr. (2006) Imaging dedicated and multifunctional neural circuits generating distinct behaviors. J Neurosci 26:10925-10933.
38. Baca S M, Marin-Burgin A, Wagenaar D A, Kristan W B, Jr. (2008) Widespread inhibition proportional to excitation controls the gain of a leech behavioral circuit. Neuron 57: 276-289.
39. Briggman K L, Kristan W B, Jr., Gonzalez J E, Kleinfeld D, Tsien R Y (2010) Monitoring integrated activity of individual neurons using FRET-based voltage-sensitive dyes. Membrane Potential Imaging in the Nervous System: Methods and Applications, eds Canepari M, Zecevic D (Springer, New York), pp 61-70.
40. Ataka K, Pieribone V A (2002) A genetically targetable fluorescent probe of channel gating with rapid kinetics. Biophys J 82:509-516.
41. Perron A, et al. (2009) Second and third generation voltage-sensitive fluorescent proteins for monitoring membrane potential. Front Mol Neurosci 2:5.
42. Siegel M S, Isacoff E Y (1997) A genetically encoded optical probe of membrane voltage. Neuron 19:735-741.
43. Kralj J M, Hochbaum D R, Douglass A D, Cohen A E (2011) Electrical spiking in *Escherichia coli* probed with a fluorescent voltage-indicating protein. Science 333:345-348.
44. Sjulson L, Miesenbock G (2007) Optical recording of action potentials and other discrete physiological events: A perspective from signal detection theory. Physiology (Bethesda) 22:47-55.
45. Fernandez J M, Taylor R E, Bezanilla F (1983) Induced capacitance in the squid giant axon. Lipophilic ion displacement currents. J Gen Physiol 82:331-346.
46. Loew L M, Bonneville G W, Surow J (1978) Charge shift optical probes of membrane potential. Theory. Biochemistry 17:4065-4071.
47. Kuhn B, Fromherz P (2003) Anellated hemicyanine dyes in a neuron membrane: Molecular Stark effect and optical voltage recording. J Phys Chem B 107:7903-7913.
48. Kuhn B, Fromherz P, Denk W (2004) High sensitivity of Stark-shift voltage-sensing dyes by one- or two-photon excitation near the red spectral edge. Biophys J 87: 631-639.
49. Ueno T, et al. (2004) Rational principles for modulating fluorescence properties of fluorescein. J Am Chem Soc 126:14079-14085.
50. Miller et al. (2012) Optically monitoring voltage in neurons by photo-induced electron transfer through molecular wires. PNAS 109(6):2114-2119.

What is claimed is:

1. A compound having a structure according to the formula:

E-M-A wherein
A is a fluorophore selected from the group consisting of xanthenes, coumarins, cyanines, and bimanes, wherein A is charged at physiological pH;
M is a molecular wire comprising a carbon containing ring and/or chain that permits a flow of electrons from one end to the other end of the wire; and
E is a hydrophobic moiety, wherein A and E are involved in a photo-induced electron transfer (PeT) through M that quenches the fluorescence of A via PeT in response to a voltage condition of a cellular membrane.

2. The compound of claim 1, wherein A is an electron acceptor and E is an electron donor in said photo-induced electron transfer.

3. The compound of claim 1, wherein A is an electron donor and E is an electron acceptor in said photo-induced electron transfer.

4. The compound of claim 1, wherein A is negatively charged at physiological pH.

5. The compound of claim 1, wherein A is a xanthene.

6. The compound of claim 1, wherein A has a structure according to the formula:

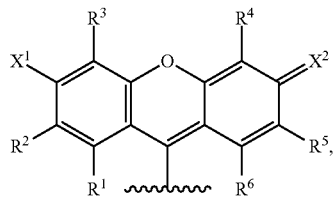

wherein $R^1$, $R^2$, $R^3$, $R^4$, $R^5$, and $R^6$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$;

$X^1$ is selected from $Z^2R^{12}$ and $NR^{11}R^{12}$;

$X^2$ is selected from $NR^{13}R^{14}$ and O;

$R^{12}$ is selected from H, alkyl, substituted alkyl, heteroalkyl, substituted heteroalkyl, and $C(Z^3)R^{15}$;

$R^{13}$ and $R^{15}$ are independently selected from alkyl, substituted alkyl, heteroalkyl, substituted heteroalkyl, $OR^{16}$ and $NR^{17}R^{18}$;

$R^{16}$ is selected from H, alkyl, substituted alkyl, heteroalkyl, substituted heteroalkyl, aryl, substituted aryl, heteroaryl, substituted heteroaryl and $C(O)R^{19}$;

$R^{19}$ is selected from alkyl, substituted alkyl, heteroalkyl and substituted heteroalkyl;

$R^{11}$, $R^{13}$, $R^{14}$, $R^{17}$ and $R^{18}$ are independently selected from H, alkyl, substituted alkyl, heteroalkyl and substituted heteroalkyl;

$Z^1$ and $Z^3$ are independently selected from O, S and NH; and $Z^2$ is selected from O and S.

7. The compound of claim 6, wherein A has a structure according to the formula:

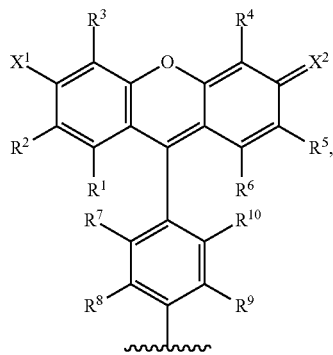

wherein $R^7$, $R^8$, $R^9$, and $R^{10}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$.

8. The compound of claim 6, wherein $X^1$ is OH, $X^2$ is O, $R^2$ is Cl, $R^5$ is Cl and $R^{10}$ is $SO_3H$.

9. The compound of claim 6, wherein $R^1$, $R^3$, $R^4$, and $R^6$ are H.

10. The compound of claim 6, wherein $R^7$, $R^8$ and $R^9$ are H.

11. The compound of claim 1, wherein E is selected from a substituted aryl and substituted heteroaryl.

12. The compound of claim 1, wherein E is phenyl substituted with an amine.

13. The compound of claim 1, wherein E has the structure according to the formula:

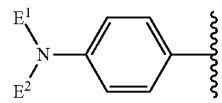

wherein $E^1$ and $E^2$ are independently alkyl.

14. The compound of claim 13, wherein $E^1$ and $E^2$ are independently selected from unsubstituted $C_1$-$C_6$ alkyl.

15. The compound of claim 14, wherein $E^1$ and $E^2$ are independently selected from methyl or butyl.

16. The compound of claim 15, wherein $E_1$ and $E_2$ are butyl.

17. The compound of claim 16, wherein said butyl is n-butyl.

18. The compound of claim 1, wherein M is selected from alkylene, substituted alkylene, heteroalkylene, substituted heteroalkylene, arylene, substituted arylene, heteroarylene and substituted heteroarylene.

19. The compound of claim 1, wherein M has a structure according to the formula:

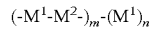

wherein $M^1$ is alkylene, $M^2$ is arylene, m is an integer selected from 0, 1, 2, 3, 4, 5, 6, 7, 8, 9, 10, 11, 12, 13, 14, 15, 16, 17, 18, 19 and 20, n is an integer selected from 0 and 1, and at least one of m and n is greater than 0.

20. The compound of claim 1, wherein M has a structure according to the formula:

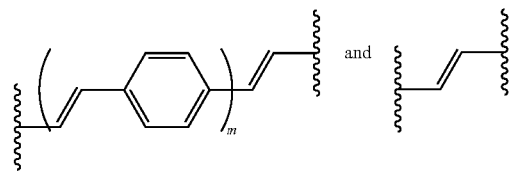

wherein m is an integer selected from 0, 1, 2, 3, 4, 5, 6, 7, 8, 9, 10, 11, 12, 13, 14, 15, 16, 17, 18, 19 and 20.

21. The compound of claim 1, wherein M is a conjugated system.

22. The compound of claim 1, wherein M is hydrophobic.

23. The compound of claim 1, having a structure selected from:

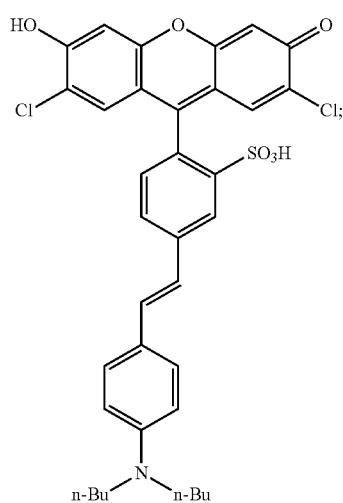
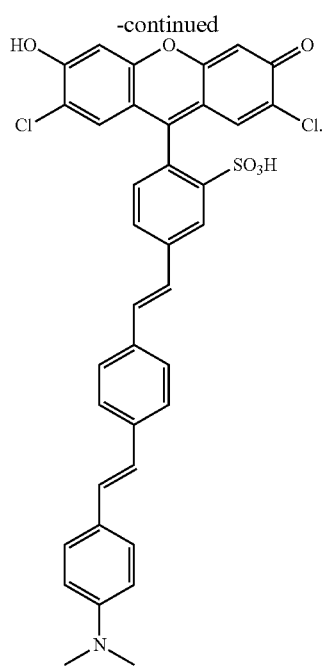
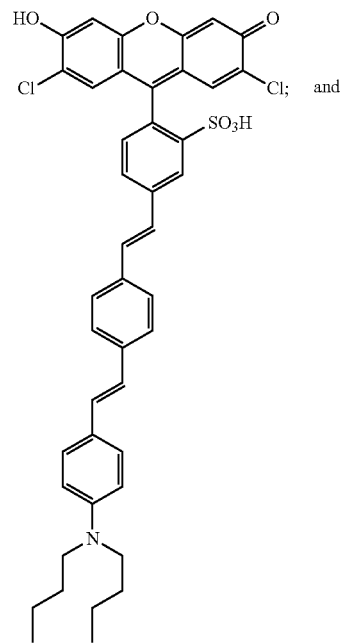
24. The compound of claim 1, having a structure selected from:
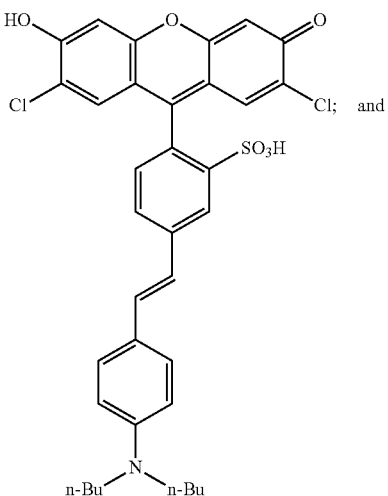

[Structure shown: a xanthene dye with HO, Cl, O, Cl substituents on xanthene, phenyl with SO₃H bearing a tri-stilbene chain ending in N(butyl)₂]

25. The compound of claim 1, substituted with a targeting moiety.

26. The compound of claim 25, wherein the targeting moiety is selected from a nucleic acid, a peptide, a saccharide, a lipid and a combination thereof.

27. The compound of claim 25, wherein the targeting moiety is specific for an excitable cell type.

28. The compound of claim 27, wherein said excitable cell type is selected from a neuron, a nerve cell, an endocrine secretory cell, a neuroendocrine secretory cell, a cardiac muscle cell, a smooth muscle cell, and a skeletal muscle cell.

29. An amphipathic compound having the structure:

E-M-A wherein
- A is a charged fluorophore selected from the group consisting of xanthenes, coumarins, cyanines, and bimanes;
- M is a molecular wire comprising a carbon containing ring and/or chain that permits a flow of electrons from one end to the other end of the wire; and
- E is an electron-rich, hydrophobic moiety involved in a photo-induced electron transfer to A through the molecular wire, which quenches the fluorescence of A in response to a voltage condition of a cellular membrane.

30. The compound of claim 29, wherein A is a positively charged fluorophore.

31. The compound of claim 29, wherein A is a negatively charged fluorophore.

32. The compound of claim 29, wherein A is a xanthene.

33. The compound of claim 29, wherein A has a structure according to the formula:

[Xanthene structure with substituents $X^1, R^3, R^4, X^2, R^2, R^5, R^1, R^6$]

wherein $R^1, R^2, R^3, R^4, R^5$, and $R^6$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$;

$X^1$ is selected from $Z^2R^{12}$ and $NR^{11}R^{12}$;

$X^2$ is selected from $NR^{13}R^{14}$ and O;

$R^{12}$ is selected from H, alkyl, substituted alkyl, heteroalkyl, substituted heteroalkyl, and $C(Z^3)R^{15}$;

$R^{13}$ and $R^{15}$ are independently selected from alkyl, substituted alkyl, heteroalkyl, substituted heteroalkyl, $OR^{16}$ and $NR^{17}R^{18}$;

$R^{16}$ is selected from H, alkyl, substituted alkyl, heteroalkyl, substituted heteroalkyl, aryl, substituted aryl, heteroaryl, substituted heteroaryl and $C(O)R^{19}$;

$R^{19}$ is selected from alkyl, substituted alkyl, heteroalkyl and substituted heteroalkyl;

$R^{11}, R^{13}, R^{14}, R^{17}$ and $R^{18}$ are independently selected from H, alkyl, substituted alkyl, heteroalkyl and substituted heteroalkyl;

$Z^1$ and $Z^3$ are independently selected from O, S and NH; and $Z^2$ is selected from O and S.

34. The compound of claim 33, wherein A has a structure according to the formula:

[Xanthene structure with additional phenyl bearing $R^7, R^8, R^9, R^{10}$]

wherein $R^7, R^8, R^9$, and $R^{10}$ are independently selected from alkyl, substituted alkyl, heteroalkyl, substituted heteroalkyl, cycloalkyl, substituted cycloalkyl, heterocycloalkyl, substituted heterocycloalkyl, aryl, substituted aryl, heteroaryl, substituted heteroaryl, halogen, H, $NO_2$, CN, $SO_3H$, $NR^{11}R^{12}$, $C(Z^1)R^{13}$ and $Z^2R^{12}$.

35. The compound of claim 32, wherein $X^1$ is OH, $X^2$ is O, $R^2$ is Cl, $R^5$ is Cl and $R^{10}$ is $SO_3H$.

36. The compound of claim 33, wherein $R^1, R^3, R^4$, and $R^6$ are H.

37. The compound of claim 36, wherein $R^7, R^8$ and $R^9$ are H.

38. The compound of claim 32, wherein E is selected from a substituted aryl and substituted heteroaryl.

39. The compound of claim 32, wherein E is phenyl substituted with an amine.

40. The compound of claim 32, wherein E has the structure according to the formula:

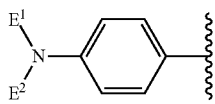

wherein $E^1$ and $E^2$ are independently alkyl.

41. The compound of claim 40, wherein $E^1$ and $E^2$ are independently selected from unsubstituted $C_1$-$C_6$ alkyl.

42. The compound of claim 41, wherein $E^1$ and $E^2$ are independently selected from methyl or butyl.

43. The compound of claim 42, wherein $E_1$ and $E_2$ are butyl.

44. The compound of claim 43, wherein said butyl is n-butyl.

45. The compound of claim 32, wherein M is selected from alkylene, substituted alkylene, heteroalkylene, substituted heteroalkylene, arylene, substituted arylene, heteroarylene and substituted heteroarylene.

46. The compound of claim 32, wherein M has a structure according to the formula:

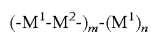

wherein $M^1$ is alkylene,
$M^2$ is arylene,
m is an integer selected from 0, 1, 2, 3, 4, 5, 6, 7, 8, 9, 10, 11, 12, 13, 14, 15, 16, 17, 18, 19 and 20,
n is an integer selected from 0 and 1, and
at least one of m and n is greater than 0.

47. The compound of claim 32, wherein M has a structure according to the formula:

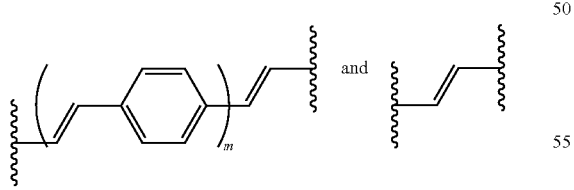

wherein m is an integer selected from 0, 1, 2, 3, 4, 5, 6, 7, 8, 9, 10, 11, 12, 13, 14, 15, 16, 17, 18, 19 and 20.

48. The compound of claim 32, wherein M is a conjugated system.

49. The compound of claim 32, wherein M is hydrophobic.

50. The compound of claim 29, having a structure selected from:

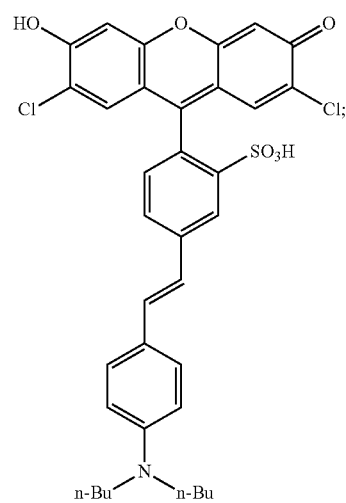

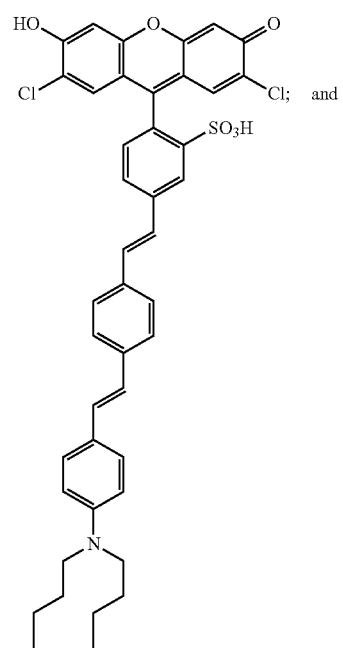

-continued

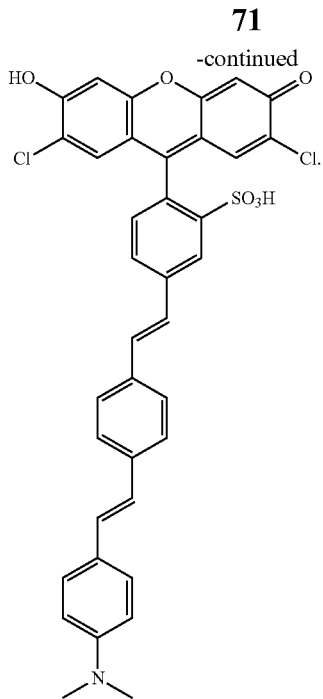

51. The compound of claim 29, having a structure selected from:

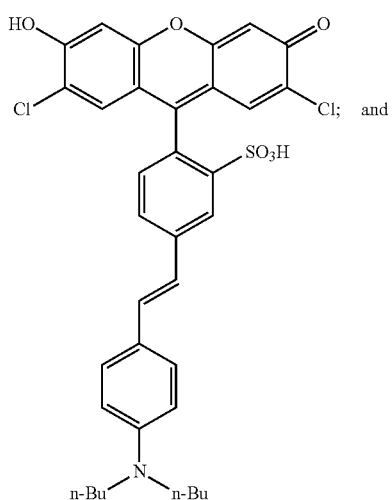

-continued

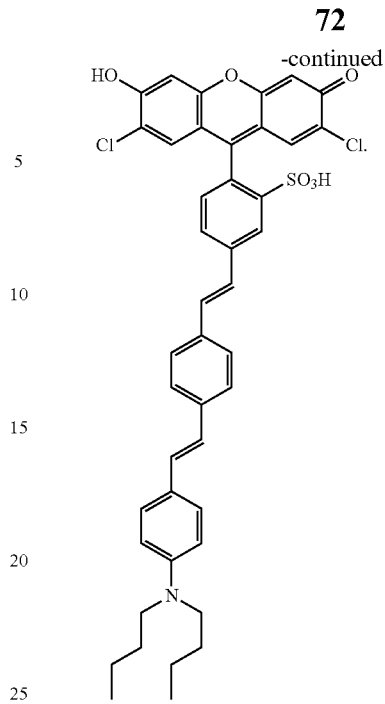

52. The compound of claim 32, substituted with a targeting moiety.

53. The compound of claim 52, wherein the targeting moiety is selected from a nucleic acid, a peptide, a saccharide, a lipid and a combination thereof.

54. The compound of claim 52, wherein the targeting moiety is specific for an excitable cell type.

55. The compound of claim 54, wherein said excitable cell type is selected from a neuron, a nerve cell, an endocrine secretory cell, a neuroendocrine secretory cell, a cardiac muscle cell, a smooth muscle cell, and a skeletal muscle cell.

56. A composition comprising a living cell, said cell having a membrane comprising the compound according to claim 1.

57. The composition of claim 56, wherein said living cell is a mammalian cell.

58. The composition of claim 56, wherein said living cell is an excitable cell type.

59. The composition of claim 58, wherein said excitable cell type is selected from a neuron, a nerve cell, an endocrine secretory cell, a neuroendocrine secretory cell, a cardiac muscle cell, a smooth muscle cell, and a skeletal muscle cell.

60. The composition of claim 56, wherein said cell is selected from a HEK293 cell and a neuron.

61. The composition of claim 56, wherein said membrane is the plasma membrane of said cell.

62. The composition of claim 56, wherein said cell is voltage clamped.

63. The composition of claim 56, wherein said membrane comprises at least one ion channel, ion transporter, ion pump, or ion exchanger.

64. The composition of claim 56, wherein the membrane of said living cell comprises an inner layer and an outer layer, A localizes at the outer layer of said membrane, and E localizes at a region between the inner layer and outer layer.

65. A method for monitoring transmembrane potential of a living cell, comprising:
  introducing a plurality of the compound according to claim 1 into a sample comprising a living cell under conditions that permit the interaction of said plurality of compound with a plasma membrane of said cell;

exciting the compound with light of a wavelength sufficient to excite the fluorophore;

detecting fluorescence emission from said plurality of the compound; and correlating said fluorescence emission to the transmembrane potential of the living cell, wherein the quenching of fluorescence emitted by said plurality of the compound is altered in response to a change in the membrane potential.

66. The method of claim 65, wherein said living cell is a mammalian cell.

67. The method of claim 65, wherein said living cell is an excitable cell type.

68. The method of claim 67, wherein said excitable cell type is selected from a neuron, a nerve cell, an endocrine secretory cell, a neuroendocrine secretory cell, a cardiac muscle cell, a smooth muscle cell, and a skeletal muscle cell.

69. The method of claim 65, wherein said cell is selected from a HEK293 cell and a neuron.

70. The method of claim 65, wherein said membrane is the plasma membrane of said cell.

71. The method of claim 65, wherein said cell is voltage clamped.

72. The method of claim 65, wherein said membrane comprises at least one ion channel, ion transporter, ion pump, or ion exchanger.

73. The method of claim 65, wherein the membrane of said living cell comprises an inner layer and an outer layer, A localizes at the outer layer of said membrane, and E localizes at a region between the inner layer and outer layer.

74. A method of identifying a candidate agent that modulates transmembrane potential in at least one living cell, said method comprising the steps:

contacting said at least one living cell with a plurality of the compound according to claim 1, wherein said cell has a membrane;

exposing the membrane to said agent;

exciting the plurality of compound with light of a wavelength sufficient to excite the fluorophore;

detecting fluorescence emission of said plurality of the compound;

correlating said fluorescence emission to transmembrane potential of the cell; and comparing said transmembrane potential to a control value, wherein a difference between said transmembrane potential and the control value is indicative of the agent's ability to modulate transmembrane potential of said cell.

75. The method of claim 74, wherein said living cell is a mammalian cell.

76. The method of claim 74, wherein said living cell is an excitable cell type.

77. The method of claim 76, wherein said excitable cell type is selected from a neuron, a nerve cell, an endocrine secretory cell, a neuroendocrine secretory cell, a cardiac muscle cell, a smooth muscle cell, and a skeletal muscle cell.

78. The method of claim 74, wherein said cell is selected from a HEK293 cell and a neuron.

79. The method of claim 74, wherein said membrane is the plasma membrane of said cell.

80. The method of claim 74, wherein said cell is voltage clamped.

81. The method of claim 74, wherein said membrane comprises at least one ion channel, ion transporter, ion pump, or ion exchanger.

82. The method of claim 74, wherein the membrane of said living cell comprises an inner layer and an outer layer, A localizes at the outer layer of said membrane, and E localizes at a region between the inner layer and outer layer.

* * * * *